(12) United States Patent
Gabellieri et al.

(10) Patent No.: US 8,748,418 B2
(45) Date of Patent: Jun. 10, 2014

(54) 1,4-OXAZEPINES AS BACE1 AND/OR BACE2 INHIBITORS

(75) Inventors: Emanuele Gabellieri, Siena (IT); Wolfgang Guba, Muellheim (DE); Hans Hilpert, Muenchenstein (CH); Harald Mauser, Riehen (CH); Alexander V. Mayweg, Shanghai (CN); Mark Rogers-Evans, Bottmingen (CH); Didier Rombach, Mulhouse (FR); Andrew Thomas, Binningen (CH); Thomas Woltering, Freiburg (DE); Wolfgang Wostl, Grenzach-Wyhlen (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 270 days.

(21) Appl. No.: 13/415,873

(22) Filed: Mar. 9, 2012

(65) Prior Publication Data
US 2012/0238548 A1 Sep. 20, 2012

(30) Foreign Application Priority Data

Mar. 18, 2011 (EP) .................................. 11158781

(51) Int. Cl.
*A61K 31/553* (2006.01)
*C07D 413/02* (2006.01)
*C07D 267/10* (2006.01)

(52) U.S. Cl.
USPC .................. 514/211.01; 514/211.15; 540/544

(58) Field of Classification Search
USPC ........................ 514/211.01, 211.15; 540/544
See application file for complete search history.

(56) References Cited

FOREIGN PATENT DOCUMENTS

| WO | 2010/128058 | 11/2010 |
|---|---|---|
| WO | 2011/009943 | 1/2011 |
| WO | 2011/020806 | 2/2011 |
| WO | 2011/138293 | 11/2011 |

OTHER PUBLICATIONS

Lagos et al., "Blood" 109(4):1550-1558 ( 2007).
Woodard-Grice et al., "J. Biol. Chem." 283(39):26364-26373 ( 2008).
Wild et al., "Diabetes Care" 27(5):1047-1053 ( 2004).
Kuhn et al., "J. Biol. Chem." 282(16):11982-11995 ( 2007).
Fukui et al., Cell Metab. 2:373-384 ( 2005).
Akpinar et al., Cell Metab. 2:385-397 ( 2005).
Koistinen et al., "Muscle & Nerve" 34(4):444-450 ( 2006).
Toegel et al., "Osteoarthritis & Cartilage" 18(2):240-248 ( 2010).
Hodges et al., Hum. Mol. Genet. 15:965-977 (2006).
Talantov et al., Clin. Cancer Res. 11:7234-7242 ( 2005).
"International Search Report PCT/EP2012/054510—mailed May 7, 2012".
Vassar et al., BACE, Science 286:735 ( 1999).
Greenberg et al., Ann. Neurol. 57:664-678 ( 2005).
Sugimoto et al., "J. Biol. Chem." 282(48):34896-34903 ( 2007).
Roberds et al., Hum. Mol. Genet. 10(12):1317-1324 ( 2001).
Hedlund et al., Cancer Research 68(2):388-394 ( 2008).
Desnues et al., Clin. Vaccine Immunol. 13:170-178 ( 2006).
Selkoe et al., "Annual Review Cell Biology" 10:373-403 ( 1994).
Basset et al., Scand. J. Immunol. 51:307-311 ( 2000).
Hardy et al., "Science" 297 (5580):353-356 ( 2002).
Prentki et al., J. Clin. Investig. 116(7):1802-1812 ( 2006).
Kiljanski et al., "Thyroid" 15(7):645-652 ( 2005).
Gatchel et al., Proc. Natl. Acad. Sci. USA 105:1291-1296 ( 2008).
McConlogue et al., "J. Biol. Chem." 282(36):26326-26334 ( 2007).
Kondoh et al., "Breast Cancer & Research Treatment" 78(1):37-44 ( 2003).
Zimmet et al., Nature 414:782-787 ( 2001).
Luo et al., "Nature Neuroscience" 3:231-232 ( 2001).
Kihara et al., Proc. Natl. Acad. Sci. USA 106:21807-21812 ( 2009).
Hussain et al., Mol. Cell Neurosci. 16:609-619 ( 2000).
Kim et al., "Neurobiology of Disease" 22(2):346-356 ( 2006).
Hoffmeister et al., "Journal of the Pancreas" 10(5):501-506 ( 2009).
Li et al., "Aging Cell" 5(2):153-165 ( 2006).
Finzi et al., "Ultrastruct. Pathol." 32(6):246-251 ( 2008).
Barbiero et al., Exp. Neurol. 182:335-345 ( 2003).
Baggio et al., Annu. Rev. Med. 57:265-281 ( 2006).
Maugeri et al., "Srp Arh Celok Lek—Abstract" 138:50-52 ( 2010).
Merten et al., "Zeitschrift fur Kardiologie" ((English language Summary is attached to the reference)), 93(11):855-863 ( 2004).
Grewal et al., Mol. Cell Biol. 26:4970-4981 ( 2006).
Vattemi et al., "Lancet" ((9297)), 358:1962-1964 ( 2001).
Lichtenthaler et al., "J. Biol. Chem." 278(49):48713-48719 ( 2003).

*Primary Examiner* — Brenda Coleman

(57) ABSTRACT

The present invention relates to 1,4-Oxazepines of formula I

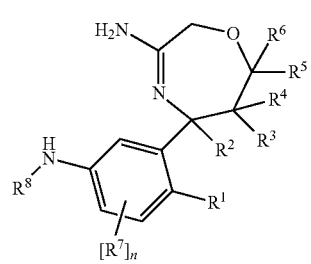

having BACE1 and/or BACE2 inhibitory activity, their manufacture, pharmaceutical compositions containing them and their use as therapeutically active substances. The active compounds of the present invention are useful in the therapeutic and/or prophylactic treatment of e.g. Alzheimer's disease and type 2 diabetes.

28 Claims, No Drawings

1,4-OXAZEPINES AS BACE1 AND/OR BACE2 INHIBITORS

PRIORITY TO RELATED APPLICATION(S)

This application claims the benefit of European Patent Application No. 11158781.2, filed Mar. 18, 2011, which is hereby incorporated by reference in its entirety.

BACKGROUND OF THE INVENTION

Alzheimer's disease (AD) is a neurodegenerative disorder of the central nervous system and the leading cause of a progressive dementia in the elderly population. Its clinical symptoms are impairment of memory, cognition, temporal and local orientation, judgment and reasoning but also severe emotional disturbances. There are currently no treatments available which can prevent the disease or its progression or stably reverse its clinical symptoms. AD has become a major health problem in all societies with high life expectancies and also a significant economic burden for their health systems.

AD is characterized by 2 major pathologies in the central nervous system (CNS), the occurrence of amyloid plaques and neurofibrillar tangles (Hardy et al., The amyloid hypothesis of Alzheimer's disease: progress and problems on the road to therapeutics, *Science.* 2002 Jul. 19; 297(5580:353-6, Selkoe, Cell biology of the amyloid beta-protein precursor and the mechanism of Alzheimer's disease, *Annu Rev Cell Biol.* 1994; 10:373-403). Both pathologies are also commonly observed in patients with Down's syndrome (trisomy 21), which also develop AD-like symptoms in early life. Neurofibrillar tangles are intracellular aggregates of the microtubule-associated protein tau (MAPT). Amyloid plaques occur in the extracellular space; their principal components are Aβ-peptides. The latter are a group of proteolytic fragments derived from the β-amyloid precursor protein (APP) by a series of proteolytic cleavage steps. Several forms of APP have been identified of which the most abundant are proteins of 695, 751 and 770 amino acids length. They all arise from a single gene through differential splicing. The Aβ-peptides are derived from the same domain of the APP but differ at their N- and C-termini, the main species are of 40 and 42 amino-acid length. There are several lines of evidence which strongly suggest that aggregated Aβ-peptides are the essential molecules in the pathogenesis of Aβ: 1) amyloid plaques formed of Aβ-peptides are invariably part of the AD pathology; 2) Aβ-peptides are toxic for neurons; 3) in Familial Alzheimer's Disease (FAD) the mutations in the disease genes APP, PSN1, PSN2 lead to increased levels of Aβ-peptides and early brain amyloidosis; 4) transgenic mice which express such FAD genes develop a pathology which bears many resemblances to the human disease. Aβ-peptides are produced from APP through the sequential action of 2 proteolytic enzymes termed β- and γ-secretase. β-Secretase cleaves first in the extracellular domain of APP approximately 28 amino acids outside of the trans-membrane domain (TM) to produce a C-terminal fragment of APP containing the TM- and the cytoplasmatic domain (CTFβ). CTFβ is the substrate for γ-secretase which cleaves at several adjacent positions within the TM to produce the Aβ peptides and the cytoplasmic fragment. The γ-secretase is a complex of at least 4 different proteins, its catalytic subunit is very likely a presenilin protein (PSEN1, PSEN2). The β-secretase (BACE1, Asp2; BACE stands for β-site APP-cleaving enzyme) is an aspartyl protease which is anchored into the membrane by a transmembrane domain (Vassar et al., Beta-secretase cleavage of Alzheimer's amyloid precursor protein by the transmembrane aspartic protease BACE, *Science.* 1999 Oct. 22; 286(5440):735). It is expressed in many tissues of the human organism but its level is especially high in the CNS. Genetic ablation of the BACE1 gene in mice has clearly shown that its activity is essential for the processing of APP which leads to the generation of Aβ-peptides, in the absence of BACE1 no Aβ-peptides are produced (Luo et al., Mice deficient in BACE1, the Alzheimer's beta-secretase, have normal phenotype and abolished beta-amyloid generation, *Nat. Neurosci.* 2001 March; 4(3):231-2, Roberds et al., BACE knockout mice are healthy despite lacking the primary beta-secretase activity in brain: implications for Alzheimer's disease therapeutics, *Hum Mol Genet.* 2001 Jun. 1; 10(12):1317-24). Mice which have been genetically engineered to express the human APP gene and which form extensive amyloid plaques and Alzheimer's disease like pathologies during aging fail to do so when β-secretase activity is reduced by genetic ablation of one of the BACE1 alleles (McConlogue et al., Partial reduction of BACE1 has dramatic effects on Alzheimer plaque and synaptic pathology in APP Transgenic Mice. *J Biol. Chem.* 2007 Sep. 7; 282(36):26326). It is thus presumed that inhibitors of BACE1 activity can be useful agents for therapeutic intervention in Alzheimer's disease (AD).

Type 2 diabetes (T2D) is caused by insulin resistance and inadequate insulin secretion from pancreatic β-cells leading to poor blood-glucose control and hyperglycemia (M Prentki & C J Nolan, "Islet beta-cell failure in type 2 diabetes." J. Clin. Investig. 2006, 116(7), 1802-1812). Patients with T2D have an increased risk of microvascular and macrovascular disease and a range of related complications including diabetic nephropathy, retinopathy and cardiovascular disease. In 2000, an estimated 171 million people had the condition with the expectation that this figure will double by 2030 (S Wild, G Roglic, A Green, R. Sicree & H King, "Global prevalence of diabetes", Diabetes Care 2004, 27(5), 1047-1053), making the disease a major healthcare problem. The rise in prevalence of T2D is associated with an increasingly sedentary lifestyle and high-energy food intake of the world's population (P Zimmet, KGMM Alberti & J Shaw, "Global and societal implications of the diabetes epidemic" Nature 2001, 414, 782-787).

β-Cell failure and consequent dramatic decline in insulin secretion and hyperglycemia marks the onset of T2D. Most current treatments do not prevent the loss of β-cell mass characterizing overt T2D. However, recent developments with GLP-1 analogues, gastrin and other agents show that preservation and proliferation of β-cells is possible to achieve, leading to an improved glucose tolerance and slower progression to overt T2D (L L Baggio & D J Drucker, "Therapeutic approaches to preserve islet mass in type 2 diabetes", Annu. Rev. Med. 2006, 57, 265-281).

Tmem27 has been identified as a protein promoting beta-cell proliferation (P Akpinar, S Kuwajima, J Krützfeldt, M Stoffel, "Tmem27: A cleaved and shed plasma membrane protein that stimulates pancreatic β cell proliferation", Cell Metab. 2005, 2, 385-397) and insulin secretion (K Fukui, Q Yang, Y Cao, N Takahashi et al., "The HNF-1 target Collectrin controls insulin exocytosis by SNARE complex formation", Cell Metab. 2005, 2, 373-384). Tmem27 is a 42 kDa membrane glycoprotein which is constitutively shed from the surface of β-cells, resulting from a degradation of the full-length cellular Tmem27. Overexpression of Tmem27 in a transgenic mouse increases β-cell mass and improves glucose tolerance in a diet-induced obesity DIO model of diabetes. Furthermore, siRNA knockout of Tmem27 in a rodent β-cell proliferation assay (e.g. using INS1e cells) reduces the proliferation rate, indicating a role for Tmem27 in control of β-cell mass.

In the same proliferation assay, BACE2 inhibitors also increase proliferation. However, BACE2 inhibition combined with Tmem27 siRNA knockdown results in low proliferation rates. Therefore, it is concluded that BACE2 is the protease responsible for the degradation of Tmem27. Furthermore, in vitro, BACE2 cleaves a peptide based on the sequence of Tmem27. The closely related protease BACE1 does not cleave this peptide and selective inhibition of BACE1 alone does not enhance proliferation of β-cells.

The close homolog BACE2 is a membrane-bound aspartyl protease and is co-localized with Tmem27 in human pancreatic β-cells (G Finzi, F Franzi, C Placidi, F Acquati et al., "BACE2 is stored in secretory granules of mouse and rat pancreatic beta cells", Ultrastruct Pathol. 2008, 32(6), 246-251). It is also known to be capable of degrading APP (I Hussain, D Powell, D Howlett, G Chapman et al., "ASP1 (BACE2) cleaves the amyloid precursor protein at the β-secretase site" Mol Cell Neurosci. 2000, 16, 609-619), IL-1R2 (P Kuhn, E Marjaux, A Imhof, B De Strooper et al., "Regulated intramembrane proteolysis of the interleukin-1 receptor II by alpha-, beta-, and gamma-secretase" J. Biol. Chem. 2007, 282(16), 11982-11995) and ACE2. The capability to degrade ACE2 indicates a possible role of BACE2 in the control of hypertension.

Inhibition of BACE2 is therefore proposed as a treatment for T2D with the potential to preserve and restore β-cell mass and stimulate insulin secretion in pre-diabetic and diabetic patients. It is therefore an object of the present invention to provide selective BACE2 inhibitors. Such compounds are useful as therapeutically active substances, particularly in the treatment and/or prevention of diseases which are associated with the inhibition of BACE2.

Furthermore, the formation, or formation and deposition, of β-amyloid peptides in, on or around neurological tissue (e.g., the brain) are inhibited by the present compounds, i.e. inhibition of the Aβ-production from APP or an APP fragment.

Inhibitors of BACE1 and/or BACE2 can in addition be used to treat the following diseases:
IBM (inclusion body myositis) (Vattemi G. et al., Lancet. 2001 Dec. 8; 358(9297):1962-4), Down's Syndrome (Barbiero L. et al, Exp Neurol. 2003 August; 182(2):335-45), Wilson's Disease (Sugimoto I. et al., J Biol. Chem. 2007 Nov. 30; 282(48):34896-903), Whipple's disease (Desnues B. et al., Clin Vaccine Immunol. 2006 February; 13(2):170-8), SpinoCerebellar Ataxia 1 and SpinoCerebellar Ataxia 7 (Gatchel J. R. et al., Proc Natl Acad Sci USA 2008 Jan. 29; 105(4):1291-6), Dermatomyositis (Greenberg S. A. et al., Ann Neurol. 2005 May; 57(5):664-78 and Greenberg S. A. et al., Neurol 2005 May; 57(5):664-78), Kaposi Sarcoma (Lagos D. et al, Blood, 2007 Feb. 15; 109(4):1550-8), Glioblastoma multiforme (E-MEXP-2576, http://www.ebi.ac.uk/microarray-as/aer/
result?queryFor=PhysicalArrayDesign&aAccession=A-MEXP-258), Rheumatoid arthritis (Ungethuem U. et al, GSE2053), Amyotrophic lateral sclerosis (Koistinen H. et al., Muscle Nerve. 2006 October; 34(4):444-50 and Li Q. X. et al, Aging Cell. 2006 April; 5(2):153-65), Huntington's Disease (Kim Y. J. et al., Neurobiol Dis. 2006 May; 22(2):346-56. Epub 2006 Jan. 19 and Hodges A. et al., Hum Mol. Genet. 2006 Mar. 15; 15(6):965-77. Epub 2006 Feb. 8), Multiple Mieloma (Kihara Y. et al, Proc Natl Acad Sci USA. 2009 Dec. 22; 106(51):21807-12), Malignant melanoma (Talantov D. et al, Clin Cancer Res. 2005 Oct. 15; 11(20):7234-42), Sjogren syndrome (Basset C. et al., Scand J Immunol 2000 March; 51(3):307-11), Lupus erythematosus (Grewal P. K. et al, Mol Cell Biol. 2006, July; 26(13):4970-81), Macrophagic myofasciitis, juvenile idiopathic arthritis, granulomatous arthritis, Breast cancer (Hedlund M. et al, Cancer Res. 2008 Jan. 15; 68(2):388-94 and Kondoh K. et al., Breast Cancer Res Treat. 2003 March; 78(1):37-44), Gastrointestinal diseases (Hoffmeister A. et al, JOP. 2009 Sep. 4; 10(5):501-6), Autoimmune/inflammatory diseases (Woodard-Grice A. V. et al., J Biol. Chem. 2008 Sep. 26; 283(39):26364-73. Epub 2008 Jul. 23), Rheumatoid Arthritis (Toegel S. et al, Osteoarthritis Cartilage. 2010 February; 18(2):240-8. Epub 2009 Sep. 22), Inflammatory reactions (Lichtenthaler S. F. et al., J Biol. Chem. 2003 Dec. 5; 278(49):48713-9. Epub 2003 Sep. 24), Arterial Thrombosis (Merten M. et al., Z Kardiol. 2004 November; 93(11):855-63), Cardiovascular diseases such as Myocardial infarction and stroke (Maugeri N. et al., Srp Arh Celok Lek. 2010 January; 138 Suppl 1:50-2) and Graves disease (Kiljański J. et al, Thyroid. 2005 July; 15(7):645-52).

FIELD OF THE INVENTION

The present invention relates to 1,4-Oxazepines having BACE1 and/or BACE2 inhibitory properties, their manufacture, pharmaceutical compositions containing them and their use as therapeutically active substances.

SUMMARY OF THE INVENTION

The present invention provides novel compounds of formula I, their manufacture, pharmaceutical compositions containint them, and their production as well as the use of compounds of formula I in the control or prevention of illnesses such as Alzheimer's disease and type 2 diabetes. Furthermore the invention provides the use of compounds of formula I in the treatment of amyotrophic lateral sclerosis (ALS), arterial thrombosis, autoimmune/inflammatory diseases, cancer such as breast cancer, cardiovascular diseases such as myocardial infarction and stroke, dermatomyositis, Down's Syndrome, gastrointestinal diseases, Glioblastoma multiforme, Graves Disease, Huntington's Disease, inclusion body myositis (IBM), inflammatory reactions, Kaposi Sarcoma, Kostmann Disease, lupus erythematosus, macrophagic myofasciitis, juvenile idiopathic arthritis, granulomatous arthritis, malignant melanoma, multiple mieloma, rheumatoid arthritis, Sjogren syndrome, SpinoCerebellar Ataxia 1, SpinoCerebellar Ataxia 7, Whipple's Disease and Wilson's Disease. The novel compounds of formula I have improved pharmacological properties.

The present invention provides 2,5,6,7-tetrahydro-[1,4]oxazepin-3-ylamines of formula I,

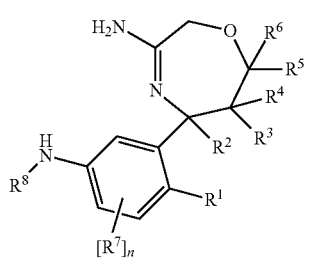

wherein the substituents and variables are as described below and in the claims, or a pharmaceutically acceptable salt thereof.

The present compounds have Asp2 (β-secretase, BACE1 or Memapsin-2) inhibitory activity and may therefore be used in the therapeutic and/or prophylactic treatment of diseases and disorders characterized by elevated β-amyloid levels and/or β-amyloid oligomers and/or β-amyloid plaques and further deposits or Alzheimer's disease. And/or the present compounds have BACE2 inhibitory activity and can therefore be used in the therapeutic and/or prophylactic treatment of diseases and disorders such as type 2 diabetes and other metabolic disorders.

DETAILED DESCRIPTION OF THE INVENTION

The present invention provides a compound of formula I and their pharmaceutically acceptable salts thereof, the preparation of the above mentioned compounds, pharmaceutical compositions containing them and their manufacture as well as the use of the above mentioned compounds in the therapeutic and/or prophylactic treatment of diseases and disorders which are associated with inhibition of BACE1 and/or BACE2 activity, such as Alzheimer's disease and type 2 diabetes. Furthermore, the formation, or formation and deposition, of β-amyloid plaques in, on or around neurological tissue (e.g., the brain) are inhibited by the present compounds by inhibiting the Aβ production from APP or an APP fragment.

The following definitions of the general terms used in the present description apply irrespective of whether the terms in question appear alone or in combination with other groups.

Unless otherwise stated, the following terms used in this Application, including the specification and claims, have the definitions given below. It must be noted that, as used in the specification and the appended claims, the singular forms "a", "an," and "the" include plural referents unless the context clearly dictates otherwise.

The term "$C_{1-6}$-alkyl", alone or in combination with other groups, stands for a hydrocarbon radical which can be linear or branched, with single or multiple branching, wherein the alkyl group contains 1 to 6 carbon atoms, for example, methyl (Me), ethyl (Et), propyl, isopropyl (i-propyl), n-butyl, i-butyl (isobutyl), 2-butyl (sec-butyl), t-butyl (tert-butyl), isopentyl, 2-ethyl-propyl, 1,2-dimethyl-propyl and the like. Particular "$C_{1-6}$-alkyl" are groups with 1 to 4 carbon atoms. Specific examples are methyl, ethyl and t-butyl—most specifically methyl.

The term "halogen-$C_{1-6}$-alkyl", alone or in combination with other groups, refers to $C_{1-6}$-alkyl as defined herein, which is substituted by one or multiple halogen atoms, in particular 1-5 halogen atoms, more particular 1-3 halogen atoms ("halogen-$C_{1-3}$-alkyl"), most particular 1 halogen atom or 2 halogen atoms. A particular halogen is fluoro. A particular "halogen-$C_{1-6}$-alkyl" is fluoro-$C_{1-6}$-alkyl. Examples are difluoromethyl, fluoromethyl and the like. A specific example is difluoromethyl.

The term "cyano-$C_{1-6}$-alkyl", alone or in combination with other groups, refers to $C_{1-6}$-alkyl as defined herein, which is substituted by one or multiple cyano groups, in particular 1 cyano group. A particular "cyano-$C_{1-6}$-alkyl" is cyano-methyl.

The term "halogen", alone or in combination with other groups, denotes chloro (Cl), iodo (I), fluoro (F) and bromo (Br). Particular "halogen" atoms are Cl and F—specifically F.

The term "cyano", alone or in combination with other groups, denotes the group —CN.

The term "heteroaryl", alone or in combination with other groups, refers to an aromatic group containing a single 4 to 8 membered ring or multiple condensed rings having 6 to 14, in particular 6 to 10, ring atoms and containing 1, 2 or 3 heteroatoms individually selected from N, O and S, in particular N and O, in which group at least one heterocyclic ring is aromatic. Examples of "heteroaryl" include benzofuryl, benzoimidazolyl, 1H-benzoimidazolyl, benzooxazinyl, benzoxazolyl, benzothiazinyl, benzothiazolyl, benzothienyl, benzotriazolyl, furyl, imidazolyl, indazolyl, 1H-indazolyl, indolyl, isoquinolinyl, isothiazolyl, isoxazolyl, oxazolyl, pyrazinyl, pyrazolyl (pyrazyl), 1H-pyrazolyl, pyrazolo[1,5-a]pyridinyl, pyridazinyl, pyridinyl, pyrimidinyl, pyrrolyl, quinolinyl, tetrazolyl, thiazolyl, thienyl, triazolyl, 6,7-dihydro-5H-[1]pyrindinyl and the like. Particular "heteroaryl" are 6,7-dihydro-5H-[1]pyrindyl, 1H-pyrazyl, 2,3-dihydro-benzofuryl, 2,3-dihydro-furo[3,2-b]pyridinyl, 5,6,7,8-tetrahydro-quinolinyl, 6,7-dihydro-5H-[1]pyrindinyl, pyridinyl. Specific examples are 6,7-dihydro-5H-[1]pyrindin-7-yl, 1H-pyrazol-3-yl, 2,3-dihydro-benzofuran-3-yl, 2,3-dihydro-furo[3,2-b]pyridin-3-yl, 5,6,7,8-tetrahydro-quinolin-8-yl, and 6,7-dihydro-5H-[1]pyrindin-7-yl, pyridin-3-yl.

The term "heteroaryl-$CH_2$-", alone or in combination with other groups, refers to a "heteroaryl" as described herein attached via a $CH_2$-group. A particular "heteroaryl-$CH_2$-" is 1H-pyrazolylmethyl, specifically 1H-pyrazol-3-ylmethyl.

The term "$C_{1-6}$-alkoxy", alone or in combination with other groups, stands for an —O—$C_{1-6}$-alkyl radical which can be linear or branched, with single or multiple branching, wherein the alkyl group contains 1 to 6 carbon atoms, for example, methoxy (OMe), ethoxy (OEt), propoxy, isopropoxy (i-propoxy), n-butoxy, i-butoxy (iso-butoxy), 2-butoxy (sec-butoxy), t-butoxy (tert-butoxy), isopentyloxy (i-pentyloxy) and the like. Particular "$C_{1-6}$-alkoxy" are groups with 1 to 4 carbon atoms. A specific example is methoxy.

The term "halogen-$C_{1-6}$-alkoxy", alone or in combination with other groups, refers to a "$C_{1-6}$-alkoxy" as described herein, which is substituted by one or multiple halogen, in particular 1-5 halogen, more particular 1-3 halogen, most particular 1 halogen or 2 halogen. Particular halogen is fluoro. Examples are fluoromethoxy, difluoromethoxy and trifluoromethyoxy.

The term "heterocyclyl", alone or in combination with other groups, denotes a monovalent saturated mono- or bicyclic ring system of 4 to 9 ring atoms, contain 1, 2, or 3 ring heteroatoms selected from N, O and S, the remaining ring atoms being carbon. Bicyclic means consisting of two rings having two ring atoms in common, i.e. the bridge separating the two rings is either a single bond or a chain of one or two ring atoms. Examples for monocyclic saturated heterocyclyl are azetidinyl, pyrrolidinyl, tetrahydrofuranyl, (tetrahydrofuryl) tetrahydro-thienyl, pyrazolidinyl, imidazolidinyl, oxazolidinyl, isoxazolidinyl, thiazolidinyl, piperidinyl, tetrahydropyranyl (tetrahydro-pyryl), tetrahydrothiopyranyl, piperazinyl, morpholinyl, thiomorpholinyl, 1,1-dioxo-thiomorpholin-4-yl, azepanyl, diazepanyl, homopiperazinyl, and oxazepanyl. Examples for bicyclic saturated heterocyclyl are 8-aza-bicyclo[3.2.1]octyl, quinuclidinyl, 8-oxa-3-aza-bicyclo[3.2.1]octyl, 9-aza-bicyclo[3.3.1]nonyl, 3-oxa-9-aza-bicyclo[3.3.1]nonyl, and 3-thia-9-aza-bicyclo[3.3.1]nonyl. Particular "heterocyclyl" are tetrahydro-furyl and tetrahydro-pyryl. Specific examples are tetrahydro-furan-3-yl, tetrahydro-pyran-3-yl and tetrahydro-pyran-4-yl.

The term "aryl", alone or in combination with other groups, refers to an aromatic carbocyclic group containing 6 to 14, in particular 6 to 10, carbon atoms and having at least one aromatic ring or multiple condensed rings in which at least one ring is aromatic. Examples of "aryl" include benzyl, biphenyl, indanyl, naphthyl, phenyl (Ph) and the like. A particular "aryl" is phenyl.

The term "pharmaceutically acceptable salts" refers to salts that are suitable for use in contact with the tissues of humans and animals. Examples of suitable salts with inorganic and organic acids are, but are not limited to, acetic acid, citric acid, formic acid, fumaric acid, hydrochloric acid, lactic acid, maleic acid, malic acid, methane-sulfonic acid, nitric acid, phosphoric acid, p-toluenesulphonic acid, succinic acid, sulfuric acid, sulphuric acid, tartaric acid, trifluoroacetic acid and the like. Particular are formic acid, trifluoroacetic acid and hydrochloric acid.

The terms "pharmaceutically acceptable carrier" and "pharmaceutically acceptable auxiliary substance" refer to carriers and auxiliary substances such as diluents or excipients that are compatible with the other ingredients of the formulation.

The term "pharmaceutical composition" encompasses a product comprising specified ingredients in pre-determined amounts or proportions, as well as any product that results, directly or indirectly, from combining specified ingredients in specified amounts. In particular it encompasses a product comprising one or more active ingredients, and an optional carrier comprising inert ingredients, as well as any product that results, directly or indirectly, from combination, complexation or aggregation of any two or more of the ingredients, or from dissociation of one or more of the ingredients, or from other types of reactions or interactions of one or more of the ingredients.

The term "inhibitor" denotes a compound which competes with, reduces or prevents the binding of a particular ligand to particular receptor or which reduces or prevents the inhibition of the function of a particular protein.

The term "half maximal inhibitory concentration" ($IC_{50}$) denotes the concentration of a particular compound required for obtaining 50% inhibition of a biological process in vitro. $IC_{50}$ values can be converted logarithmically to $pIC_{50}$ values ($-\log IC_{50}$), in which higher values indicate exponentially greater potency. The $IC_{50}$ value is not an absolute value but depends on experimental conditions e.g. concentrations employed. The $IC_{50}$ value can be converted to an absolute inhibition constant (Ki) using the Cheng-Prusoff equation (Biochem. Pharmacol. (1973) 22:3099). The term "inhibition constant" (Ki) denotes the absolute binding affinity of a particular inhibitor to a receptor. It is measured using competition binding assays and is equal to the concentration where the particular inhibitor would occupy 50% of the receptors if no competing ligand (e.g. a radioligand) was present. Ki values can be converted logarithmically to pKi values (–log Ki), in which higher values indicate exponentially greater potency.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgment of the attending medical or veterinary practitioner, and other factors.

The term "as defined herein" and "as described herein" when referring to a variable incorporates by reference the broad definition of the variable as well as preferred, more preferred and most preferred definitions, if any.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

The term "protecting group" denotes the group which selectively blocks a reactive site in a multifunctional compound such that a chemical reaction can be carried out selectively at another unprotected reactive site in the meaning conventionally associated with it in synthetic chemistry. Protecting groups can be removed at the appropriate point. Exemplary protecting groups are amino-protecting groups, carboxy-protecting groups or hydroxy-protecting groups. The term "amino-protecting group" denotes groups intended to protect an amino group and includes benzyl, benzyloxycarbonyl (carbobenzyloxy, CBZ), 9-Fluorenylmethyloxycarbonyl (FMOC), p-methoxybenzyloxycarbonyl, p-nitrobenzyloxycarbonyl, tert-butoxycarbonyl (BOC), and trifluoroacetyl. Further examples of these groups are found in T. W. Greene and P. G. M. Wuts, "Protective Groups in Organic Synthesis", 2nd ed., John Wiley & Sons, Inc., New York, N.Y., 1991, chapter 7; E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, N.Y., 1981. The term "protected amino group" refers to an amino group substituted by an amino-protecting groups. Particular amino-protecting groups are tert-butoxycarbonyl group, a bis(dimethoxyphenyl)-phenylmethyl and dimethoxytrityl.

The term "leaving group" denotes the group with the meaning conventionally associated with it in synthetic organic chemistry, i.e., an atom or group displaceable under substitution reaction conditions. Examples of leaving groups include halogen, in particular bromo, alkane- or arylenesulfonyloxy, such as methanesulfonyloxy, ethanesulfonyloxy, thiomethyl, benzenesulfonyloxy, tosyloxy, and thienyloxy, dihalophosphinoyloxy, optionally substituted benzyloxy, isopropyloxy, and acyloxy.

The term "aromatic" denotes the conventional idea of aromaticity as defined in the literature, in particular in IUPAC—Compendium of Chemical Terminology, 2nd, A. D. McNaught & A. Wilkinson (Eds). Blackwell Scientific Publications, Oxford (1997).

The term "pharmaceutically acceptable excipient" denotes any ingredient having no therapeutic activity and being non-toxic such as disintegrators, binders, fillers, solvents, buffers, tonicity agents, stabilizers, antioxidants, surfactants or lubricants used in formulating pharmaceutical products.

Whenever a chiral carbon is present in a chemical structure, it is intended that all stereoisomers associated with that chiral carbon are encompassed by the structure.

The invention also provides pharmaceutical compositions, methods of using, and methods of preparing the aforementioned compounds.

All separate embodiments can be combined.

One embodiment of the invention is a compound of formula I,

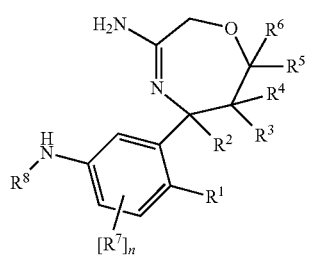

I wherein
R¹ is selected from the group consisting of
  hydrogen,
  halogen, and
  $C_{1-6}$-alkyl;
R² is selected from the group consisting of
  hydrogen,
  $C_{1-6}$-alkyl, and
  halogen-$C_{1-6}$-alkyl;
R³ is selected from the group consisting of
  halogen,
  hydrogen, and
  $C_{1-6}$-alkyl;
R⁴ is selected from the group consisting of
  hydrogen and
  halogen;
R⁵ is selected from the group consisting of
  hydrogen and
  $C_{1-6}$-alkyl;
R⁶ is selected from the group consisting of
  hydrogen and
  $C_{1-6}$-alkyl;
R⁷ is selected from the group consisting of
  halogen and
  $C_{1-6}$-alkyl;
n is 0 or 1; and
R⁸ is selected from the group consisting of
  heteroaryl,
  heteroaryl, substituted by 1-4 substituents individually selected from the group consisting of cyano, cyano-$C_{1-6}$-alkyl, halogen, halogen-$C_{1-6}$-alkyl, halogen-$C_{1-6}$-alkoxy, $C_{1-6}$-alkoxy and $C_{1-6}$-alkyl,
  heteroaryl-CH₂—,
  heteroaryl-CH₂—, substituted by 1-4 substituents individually selected from the group consisting of cyano, cyano-$C_{1-6}$-alkyl, halogen, halogen-$C_{1-6}$-alkyl, halogen-$C_{1-6}$-alkoxy, $C_{1-6}$-alkoxy and $C_{1-6}$-alkyl, aryl, aryl, substituted by 1-4 substituents individually selected from the group consisting of cyano, cyano-$C_{1-6}$-alkyl, halogen, halogen-$C_{1-6}$-alkyl, halogen-$C_{1-6}$-alkoxy, $C_{1-6}$-alkoxy and $C_{1-6}$-alkyl,
  heterocyclyl, and
  heterocyclyl, substituted by 1-4 substituents individually selected from the group consisting of cyano, cyano-$C_{1-6}$-alkyl, halogen, halogen-$C_{1-6}$-alkyl, halogen-$C_{1-6}$-alkoxy, $C_{1-6}$-alkoxy and $C_{1-6}$-alkyl; or pharmaceutically acceptable salts thereof.

One embodiment of the invention is a compound of formula Ia

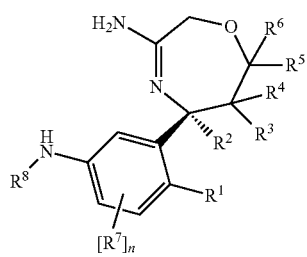

wherein
R¹ is selected from the group consisting of
  hydrogen,
  halogen, and
  $C_{1-6}$-alkyl;
R² is selected from the group consisting of
  hydrogen,
  $C_{1-6}$-alkyl, and
  halogen-$C_{1-6}$-alkyl;
R³ is selected from the group consisting of
  halogen,
  hydrogen, and
  $C_{1-6}$-alkyl;
R⁴ is selected from the group consisting of
  hydrogen and
  halogen;
R⁵ is selected from the group consisting of
  hydrogen and
  $C_{1-6}$-alkyl;
R⁶ is selected from the group consisting of
  hydrogen and
  $C_{1-6}$-alkyl;
R⁷ is selected from the group consisting of
  halogen and
  $C_{1-6}$-alkyl;
n is 0 or 1; and
R⁸ is selected from the group consisting of
  heteroaryl,
  heteroaryl, substituted by 1-4 substituents individually selected from the group consisting of cyano, cyano-$C_{1-6}$-alkyl, halogen, halogen-$C_{1-6}$-alkyl, halogen-$C_{1-6}$-alkoxy, $C_{1-6}$-alkoxy and $C_{1-6}$-alkyl, heteroaryl-CH₂—,
  heteroaryl-CH₂—, substituted by 1-4 substituents individually selected from the group consisting of cyano, cyano-$C_{1-6}$-alkyl, halogen, halogen-$C_{1-6}$-alkyl, halogen-$C_{1-6}$-alkoxy, $C_{1-6}$-alkoxy and $C_{1-6}$-alkyl, aryl, aryl, substituted by 1-4 substituents individually selected from the group consisting of cyano, cyano-$C_{1-6}$-alkyl, halogen, halogen-$C_{1-6}$-alkyl, halogen-$C_{1-6}$-alkoxy, $C_{1-6}$-alkoxy and $C_{1-6}$-alkyl, heterocyclyl, and heterocyclyl, substituted by 1-4 substituents individually selected from the group consisting of cyano, cyano-$C_{1-6}$-alkyl, halogen, halogen-$C_{1-6}$-alkyl, halogen-$C_{1-6}$-alkoxy, $C_{1-6}$-alkoxy and $C_{1-6}$-alkyl; or pharmaceutically acceptable salts thereof.

One embodiment of the invention is a compound of formula I, wherein R¹ is halogen.
One embodiment of the invention is a compound of formula I, wherein R¹ is F.
One embodiment of the invention is a compound of formula I, wherein R² is $C_{1-6}$-alkyl.
One embodiment of the invention is a compound of formula I, wherein R² is Me.
One embodiment of the invention is a compound of formula I, wherein R³ is halogen.
One embodiment of the invention is a compound of formula I, wherein R³ is F.
One embodiment of the invention is a compound of formula I, wherein R⁴ is halogen.
One embodiment of the invention is a compound of formula I, wherein R⁴ is F.
One embodiment of the invention is a compound of formula I, wherein R⁴ is hydrogen.
One embodiment of the invention is a compound of formula I, wherein R³ is F and R⁴ is F.
One embodiment of the invention is a compound of formula I, wherein R⁵ is $C_{1-6}$-alkyl.
One embodiment of the invention is a compound of formula I, wherein R⁵ is Me.
One embodiment of the invention is a compound of formula I, wherein R⁵ is hydrogen.

One embodiment of the invention is a compound of formula I, wherein $R^6$ is $C_{1-6}$-alkyl.

One embodiment of the invention is a compound of formula I, wherein $R^6$ is Me.

One embodiment of the invention is a compound of formula I, wherein $R^6$ is hydrogen.

One embodiment of the invention is a compound of formula I, wherein $R^5$ is hydrogen and $R^6$ is hydrogen.

One embodiment of the invention is a compound of formula I, wherein $R^3$ is F, $R^4$ is F, $R^5$ is hydrogen and $R^6$ is hydrogen.

One embodiment of the invention is a compound of formula I, wherein $R^1$ is F, $R^2$ is Me, $R^3$ is F, $R^4$ is F, $R^5$ is hydrogen and $R^6$ is hydrogen.

One embodiment of the invention is a compound of formula I, wherein $R^5$ is Me and $R^6$ is Me.

One embodiment of the invention is a compound of formula I, wherein $R^3$ is F, $R^4$ is F, $R^5$ is Me and $R^6$ is Me.

One embodiment of the invention is a compound of formula I, wherein $R^1$ is F, $R^2$ is Me, $R^3$ is F, $R^4$ is F, $R^5$ is Me and $R^6$ is Me.

One embodiment of the invention is a compound of formula I, wherein n is 0.

One embodiment of the invention is a compound of formula I, wherein n is 1.

One embodiment of the invention is a compound of formula I, wherein $R^7$ is halogen.

One embodiment of the invention is a compound of formula I, wherein $R^7$ is F.

One embodiment of the invention is a compound of formula Ix, wherein $R^1$-$R^8$ is as described herein.

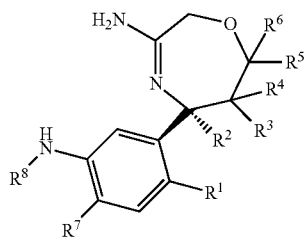

Ix

One embodiment of the invention is a compound of formula I, wherein $R^8$ is selected from the group consisting of heteroaryl, substituted by 1-2 substituents individually selected from the group consisting of cyano, halogen, $C_{1-6}$-alkoxy and $C_{1-6}$-alkyl;
heteroaryl-$CH_2$—, substituted by 1-2 substituents individually selected from the group consisting of halogen and halogen-$C_{1-6}$-alkyl;
aryl, substituted by 1-2 substituents individually selected from the group consisting of cyano, and halogen; and
heterocyclyl.

One embodiment of the invention is a compound of formula I, wherein $R^8$ is heteroaryl.

One embodiment of the invention is a compound of formula I, wherein $R^8$ is 6,7-dihydro-5H-[1]pyrindin-7-yl.

One embodiment of the invention is a compound of formula I, wherein $R^8$ is 2,3-dihydro-furo[3,2-b]pyridin-3-yl.

One embodiment of the invention is a compound of formula I, wherein $R^8$ is 5,6,7,8-tetrahydro-quinolin-8-yl.

One embodiment of the invention is a compound of formula I, wherein $R^8$ is 2,3-dihydro-benzofuran-3-yl.

One embodiment of the invention is a compound of formula I, wherein $R^8$ is 1H-pyrazol-3-yl.

One embodiment of the invention is a compound of formula I, wherein $R^8$ is pyridin-3-yl.

One embodiment of the invention is a compound of formula I, wherein $R^8$ is heteroaryl substituted by halogen.

One embodiment of the invention is a compound of formula I, wherein $R^8$ is 3-chloro-6,7-dihydro-5H-[1]pyrindin-7-yl.

One embodiment of the invention is a compound of formula I, wherein $R^8$ is 6-chloro-2,3-dihydro-furo[3,2-b]pyridin-3-yl.

One embodiment of the invention is a compound of formula I, wherein $R^8$ is 6-chloro-2,3-dihydro-benzofuran-3-yl.

One embodiment of the invention is a compound of formula I, wherein $R^8$ is 6-chloro-pyridin-3-yl.

One embodiment of the invention is a compound of formula I, wherein $R^8$ is 5-fluoro-pyridin-3-yl.

One embodiment of the invention is a compound of formula I, wherein $R^8$ is heteroaryl substituted by cyano.

One embodiment of the invention is a compound of formula I, wherein $R^8$ is 3-cyano-6,7-dihydro-5H-[1]pyrindin-7-yl.

One embodiment of the invention is a compound of formula I, wherein $R^8$ is 3-cyano-5,6,7,8-tetrahydro-quinolin-8-yl.

One embodiment of the invention is a compound of formula I, wherein $R^8$ is heteroaryl substituted by $C_{1-6}$-alkyl.

One embodiment of the invention is a compound of formula I, wherein $R^8$ is 1-methyl-1H-pyrazol-3-yl.

One embodiment of the invention is a compound of formula I, wherein $R^8$ is 6-methyl-pyridin-3-yl.

One embodiment of the invention is a compound of formula I, wherein $R^8$ is heteroaryl substituted by $C_{1-6}$-alkoxy.

One embodiment of the invention is a compound of formula I, wherein $R^8$ is 6-methoxy-pyridin-3-yl.

One embodiment of the invention is a compound of formula I, wherein $R^8$ is heteroaryl substituted by halogen-$C_{1-6}$-alkyl.

One embodiment of the invention is a compound of formula I, wherein $R^8$ is 5-trifluoromethyl-pyridin-3-yl.

One embodiment of the invention is a compound of formula I, wherein $R^8$ is heteroaryl substituted by halogen-$C_{1-6}$-alkoxy.

One embodiment of the invention is a compound of formula I, that is (R)-6,6-Difluoro-5-{2-fluoro-5-[6-(2,2,2-trifluoro-ethoxy)-pyridin-3-ylamino]-phenyl}-5,7,7-trimethyl-2,5,6,7-tetrahydro-[1,4]oxazepin-3-ylamine.

One embodiment of the invention is a compound of formula I, wherein $R^8$ is heteroaryl-$CH_2$—.

One embodiment of the invention is a compound of formula I, wherein $R^8$ is 1H-pyrazol-3-ylmethyl.

One embodiment of the invention is a compound of formula I, wherein $R^8$ is 1H-pyrazol-3-ylmethyl.

One embodiment of the invention is a compound of formula I, wherein $R^8$ is heteroaryl-$CH_2$-substituted by halogen.

One embodiment of the invention is a compound of formula I, wherein $R^8$ is 4-chloro-1-difluoromethyl-1H-pyrazol-3-ylmethyl.

One embodiment of the invention is a compound of formula I, wherein $R^8$ is heteroaryl-$CH_2$-substituted by halogen and halogen-$C_{1-6}$-alkyl.

One embodiment of the invention is a compound of formula I, wherein $R^8$ is 4-chloro-1-difluoromethyl-1H-pyrazol-3-ylmethyl.

One embodiment of the invention is a compound of formula I, wherein $R^8$ is heterocyclyl.

One embodiment of the invention is a compound of formula I, wherein $R^8$ is tetrahydro-furan-3-yl.

One embodiment of the invention is a compound of formula I, wherein $R^8$ is tetrahydro-pyran-3-yl.

One embodiment of the invention is a compound of formula I, wherein $R^8$ is tetrahydro-pyran-4-yl.

One embodiment of the invention is a compound of formula I, wherein $R^8$ is aryl.

One embodiment of the invention is a compound of formula I, wherein $R^8$ is phenyl.

One embodiment of the invention is a compound of formula I, wherein $R^8$ is aryl substituted by cyano.

One embodiment of the invention is a compound of formula I, wherein $R^8$ is 4-cyano-phenyl.

One embodiment of the invention is a compound of formula I, wherein $R^8$ is aryl substituted by halogen.

One embodiment of the invention is a compound of formula I, wherein $R^8$ is 4-fluoro-phenyl.

One embodiment of the invention is a compound of formula I, wherein $R^8$ is selected from the group consisting of heteroaryl substituted by halogen or $C_{1-6}$-alkyl and aryl substituted by halogen.

One embodiment of the invention is a compound of formula I, wherein $R^8$ is selected from the group consisting of 3-chloro-6,7-dihydro-5H-[1]pyrindin-7-yl, 1-methyl-1H-pyrazol-3-yl and 4-fluoro-phenyl.

One embodiment of the invention is a compound of formula I, selected from the group consisting of

[3-((5R,6R)-3-Amino-6-fluoro-5-methyl-2,5,6,7-tetrahydro-[1,4]oxazepin-5-yl)-4-fluoro-phenyl]-(3-chloro-6,7-dihydro-5H-[1]pyrindin-7-yl)-amine, (5R,6R)-5-{5-[(4-Chloro-1-difluoromethyl-1H-pyrazol-3-ylmethyl)-amino]-2-fluoro-phenyl}-6-fluoro-5-methyl-2,5,6,7-tetrahydro-[1,4]oxazepin-3-ylamine, (5R,6R)-6-Fluoro-5-[2-fluoro-5-(tetrahydro-furan-3-ylamino)-phenyl]-5-methyl-2,5,6,7-tetrahydro-[1,4]oxazepin-3-ylamine, (5R,6R)-6-Fluoro-5-[2-fluoro-5-(tetrahydro-pyran-3-ylamino)-phenyl]-5-methyl-2,5,6,7-tetrahydro-[1,4]oxazepin-3-ylamine, (5R,6R)-6-Fluoro-5-[2-fluoro-5-(tetrahydro-pyran-4-ylamino)-phenyl]-5-methyl-2,5,6,7-tetrahydro-[1,4]oxazepin-3-ylamine, (R)-5-[5-(6-Chloro-2,3-dihydro-benzofuran-3-ylamino)-2-fluoro-phenyl]-6,6-difluoro-5,7,7-trimethyl-2,5,6,7-tetrahydro-[1,4]oxazepin-3-ylamine, (R)-5-[5-(6-Chloro-pyridin-3-ylamino)-2-fluoro-phenyl]-6,6-difluoro-5,7,7-trimethyl-2,5,6,7-tetrahydro-[1,4]oxazepin-3-ylamine, (R)-5-{5-[(4-Chloro-1-difluoromethyl-1H-pyrazol-3-ylmethyl)-amino]-2-fluoro-phenyl}-6,6-difluoro-5-methyl-2,5,6,7-tetrahydro-[1,4]oxazepin-3-ylamine, (R)-5-{5-[(4-Chloro-1-difluoromethyl-1H-pyrazol-3-ylmethyl)-amino]-2-fluoro-phenyl}-5-ethyl-6,6-difluoro-2,5,6,7-tetrahydro-[1,4]oxazepin-3-ylamine, (R)-6,6-Difluoro-5-[2-fluoro-5-(1-methyl-1H-pyrazol-3-ylamino)-phenyl]-5,7,7-trimethyl-2,5,6,7-tetrahydro-[1,4]oxazepin-3-ylamine, (R)-6,6-Difluoro-5-[2-fluoro-5-(4-fluoro-phenylamino)-phenyl]-5,7,7-trimethyl-2,5,6,7-tetrahydro-[1,4]oxazepin-3-ylamine, (R)-6,6-Difluoro-5-[2-fluoro-5-(5-fluoro-pyridin-3-ylamino)-phenyl]-5,7,7-trimethyl-2,5,6,7-tetrahydro-[1,4]oxazepin-3-ylamine, (R)-6,6-Difluoro-5-[2-fluoro-5-(5-trifluoromethyl-pyridin-3-ylamino)-phenyl]-5,7,7-trimethyl-2,5,6,7-tetrahydro-[1,4]oxazepin-3-ylamine, (R)-6,6-Difluoro-5-[2-fluoro-5-(6-methoxy-pyridin-3-ylamino)-phenyl]-5,7,7-trimethyl-2,5,6,7-tetrahydro-[1,4]oxazepin-3-ylamine, (R)-6,6-Difluoro-5-[2-fluoro-5-(6-methyl-pyridin-3-ylamino)-phenyl]-5,7,7-trimethyl-2,5,6,7-tetrahydro-[1,4]oxazepin-3-ylamine, (R)-6,6-Difluoro-5-[2-fluoro-5-(pyridin-3-ylamino)-phenyl]-5,7,7-trimethyl-2,5,6,7-tetrahydro-[1,4]oxazepin-3-ylamine, (R)-7-[3-((R)-3-Amino-6,6-difluoro-5,7,7-trimethyl-2,5,6,7-tetrahydro-[1,4]oxazepin-5-yl)-4-fluoro-phenylamino]-6,7-dihydro-5H-[1]pyrindine-3-carbonitrile, (R)-7-[5-((R)-3-Amino-6,6-difluoro-5,7,7-trimethyl-2,5,6,7-tetrahydro-[1,4]oxazepin-5-yl)-2,4-difluoro-phenylamino]-6,7-dihydro-5H-[1]pyrindine-3-carbonitrile, (S)-7-[3-((R)-3-Amino-6,6-difluoro-5,7,7-trimethyl-2,5,6,7-tetrahydro-[1,4]oxazepin-5-yl)-4-fluoro-phenylamino]-6,7-dihydro-5H-[1]pyrindine-3-carbonitrile,

[3-((R)-3-Amino-6,6-difluoro-5,7,7-trimethyl-2,5,6,7-tetrahydro-[1,4]oxazepin-5-yl)-4-fluoro-phenyl]-(3-chloro-6,7-dihydro-5H-[1]pyrindin-7-yl)-amine,

[3-((R)-3-Amino-6,6-difluoro-5,7,7-trimethyl-2,5,6,7-tetrahydro-[1,4]oxazepin-5-yl)-4-fluoro-phenyl]-(6-chloro-2,3-dihydro-furo[3,2-b]pyridin-3-yl)-amine,

[3-((R)-3-Amino-6,6-difluoro-5-methyl-2,5,6,7-tetrahydro-[1,4]oxazepin-5-yl)-4-fluoro-phenyl]-((S)-3-chloro-6,7-dihydro-5H-[1]pyrindin-7-yl)-amine,

[3-((R)-3-Amino-6,6-difluoro-5-methyl-2,5,6,7-tetrahydro-[1,4]oxazepin-5-yl)-4-fluoro-phenyl]-((R)-3-chloro-6,7-dihydro-5H-[1]pyrindin-7-yl)-amine, 4-[3-((R)-3-Amino-6,6-difluoro-5-methyl-2,5,6,7-tetrahydro-[1,4]oxazepin-5-yl)-4-fluoro-phenylamino]-benzonitrile, 8-[3-((R)-3-Amino-6,6-difluoro-5,7,7-trimethyl-2,5,6,7-tetrahydro-[1,4]oxazepin-5-yl)-4-fluoro-phenylamino]-5,6,7,8-tetrahydro-quinoline-3-carbonitrile, (S)-7-[5-((R)-3-Amino-6,6-difluoro-5,7,7-trimethyl-2,5,6,7-tetrahydro-[1,4]oxazepin-5-yl)-2,4-difluoro-phenylamino]-6,7-dihydro-5H-[1]pyrindine-3-carbonitrile, and (R)-6,6-Difluoro-5-{2-fluoro-5-[6-(2,2,2-trifluoro-ethoxy)-pyridin-3-ylamino]-phenyl}-5,7,7-trimethyl-2,5,6,7-tetrahydro-[1,4]oxazepin-3-ylamine, or a pharmaceutical acceptable salt thereof.

One embodiment of the invention is a compound of formula I, selected from the group consisting of

[3-((5R,6R)-3-Amino-6-fluoro-5-methyl-2,5,6,7-tetrahydro-[1,4]oxazepin-5-yl)-4-fluoro-phenyl]-(3-chloro-6,7-dihydro-5H-[1]pyrindin-7-yl)-amine, (5R,6R)-5-{5-[(4-Chloro-1-difluoromethyl-1H-pyrazol-3-ylmethyl)-amino]-2-fluoro-phenyl}-6-fluoro-5-methyl-2,5,6,7-tetrahydro-[1,4]oxazepin-3-ylamine, (5R,6R)-6-Fluoro-5-[2-fluoro-5-(tetrahydro-furan-3-ylamino)-phenyl]-5-methyl-2,5,6,7-tetrahydro-[1,4]oxazepin-3-ylamine, (5R,6R)-6-Fluoro-5-[2-fluoro-5-(tetrahydro-pyran-3-ylamino)-phenyl]-5-methyl-2,5,6,7-tetrahydro-[1,4]oxazepin-3-ylamine, (5R,6R)-6-Fluoro-5-[2-fluoro-5-(tetrahydro-pyran-4-ylamino)-phenyl]-5-methyl-2,5,6,7-tetrahydro-[1,4]oxazepin-3-ylamine, (R)-5-[5-(6-Chloro-2,3-dihydro-benzofuran-3-ylamino)-2-fluoro-phenyl]-6,6-difluoro-5,7,7-trimethyl-2,5,6,7-tetrahydro-[1,4]oxazepin-3-ylamine, (R)-5-[5-(6-Chloro-pyridin-3-ylamino)-2-fluoro-phenyl]-6,6-difluoro-5,7,7-trimethyl-2,5,6,7-tetrahydro-[1,4]oxazepin-3-ylamine, (R)-5-{5-[(4-Chloro-1-difluoromethyl-1H-pyrazol-3-ylmethyl)-amino]-2-fluoro-phenyl}-6,6-difluoro-5-methyl-2,5,6,7-tetrahydro-[1,4]oxazepin-3-ylamine,
(R)-5-{5-[(4-Chloro-1-difluoromethyl-1H-pyrazol-3-ylmethyl)-amino]-2-fluoro-phenyl}-5-ethyl-6,6-difluoro-2,5,6,7-tetrahydro-[1,4]oxazepin-3-ylamine,
(R)-6,6-Difluoro-5-[2-fluoro-5-(1-methyl-1H-pyrazol-3-ylamino)-phenyl]-5,7,7-trimethyl-2,5,6,7-tetrahydro-[1,4]oxazepin-3-ylamine,
(R)-6,6-Difluoro-5-[2-fluoro-5-(4-fluoro-phenylamino)-phenyl]-5,7,7-trimethyl-2,5,6,7-tetrahydro-[1,4]oxazepin-3-ylamine,
(R)-6,6-Difluoro-5-[2-fluoro-5-(5-fluoro-pyridin-3-ylamino)-phenyl]-5,7,7-trimethyl-2,5,6,7-tetrahydro-[1,4]oxazepin-3-ylamine,
(R)-6,6-Difluoro-5-[2-fluoro-5-(5-trifluoromethyl-pyridin-3-ylamino)-phenyl]-5,7,7-trimethyl-2,5,6,7-tetrahydro-[1,4]oxazepin-3-ylamine,
(R)-6,6-Difluoro-5-[2-fluoro-5-(6-methoxy-pyridin-3-ylamino)-phenyl]-5,7,7-trimethyl-2,5,6,7-tetrahydro-[1,4]oxazepin-3-ylamine,
(R)-6,6-Difluoro-5-[2-fluoro-5-(6-methyl-pyridin-3-ylamino)-phenyl]-5,7,7-trimethyl-2,5,6,7-tetrahydro-[1,4]oxazepin-3-ylamine,
(R)-6,6-Difluoro-5-[2-fluoro-5-(pyridin-3-ylamino)-phenyl]-5,7,7-trimethyl-2,5,6,7-tetrahydro-[1,4]oxazepin-3-ylamine,
(R)-7-[3-((R)-3-Amino-6,6-difluoro-5,7,7-trimethyl-2,5,6,7-tetrahydro-[1,4]oxazepin-5-yl)-4-fluoro-phenylamino]-6,7-dihydro-5H-[1]pyrindine-3-carbonitrile,
(R)-7-[5-((R)-3-Amino-6,6-difluoro-5,7,7-trimethyl-2,5,6,7-tetrahydro-[1,4]oxazepin-5-yl)-2,4-difluoro-phenylamino]-6,7-dihydro-5H-[1]pyrindine-3-carbonitrile,
(S)-7-[3-((R)-3-Amino-6,6-difluoro-5,7,7-trimethyl-2,5,6,7-tetrahydro-[1,4]oxazepin-5-yl)-4-fluoro-phenylamino]-6,7-dihydro-5H-[1]pyrindine-3-carbonitrile,
[3-((R)-3-Amino-6,6-difluoro-5,7,7-trimethyl-2,5,6,7-tetrahydro-[1,4]oxazepin-5-yl)-4-fluoro-phenyl]-(3-chloro-6,7-dihydro-5H-[1]pyrindin-7-yl)-amine,
[3-((R)-3-Amino-6,6-difluoro-5,7,7-trimethyl-2,5,6,7-tetrahydro-[1,4]oxazepin-5-yl)-4-fluoro-phenyl]-(6-chloro-2,3-dihydro-furo[3,2-b]pyridin-3-yl)-amine,
[3-((R)-3-Amino-6,6-difluoro-5-methyl-2,5,6,7-tetrahydro-[1,4]oxazepin-5-yl)-4-fluoro-phenyl]-((S)-3-chloro-6,7-dihydro-5H-[1]pyrindin-7-yl)-amine,
[3-((R)-3-Amino-6,6-difluoro-5-methyl-2,5,6,7-tetrahydro-[1,4]oxazepin-5-yl)-4-fluoro-phenyl]-((R)-3-chloro-6,7-dihydro-5H-[1]pyrindin-7-yl)-amine,
4-[3-((R)-3-Amino-6,6-difluoro-5-methyl-2,5,6,7-tetrahydro-[1,4]oxazepin-5-yl)-4-fluoro-phenylamino]-benzonitrile,
8-[3-((R)-3-Amino-6,6-difluoro-5,7,7-trimethyl-2,5,6,7-tetrahydro-[1,4]oxazepin-5-yl)-4-fluoro-phenylamino]-5,6,7,8-tetrahydro-quinoline-3-carbonitrile, and
(S)-7-[5-((R)-3-Amino-6,6-difluoro-5,7,7-trimethyl-2,5,6,7-tetrahydro-[1,4]oxazepin-5-yl)-2,4-difluoro-phenylamino]-6,7-dihydro-5H-[1]pyrindine-3-carbonitrile,
or a pharmaceutical acceptable salt thereof.

One embodiment of the invention is a compound of formula I, selected from the group consisting of
[3-((5R,6R)-3-Amino-6-fluoro-5-methyl-2,5,6,7-tetrahydro-[1,4]oxazepin-5-yl)-4-fluoro-phenyl]-(3-chloro-6,7-dihydro-5H-[1]pyrindin-7-yl)-amine,
(R)-6,6-Difluoro-5-[2-fluoro-5-(1-methyl-1H-pyrazol-3-ylamino)-phenyl]-5,7,7-trimethyl-2,5,6,7-tetrahydro-[1,4]oxazepin-3-ylamine,
(R)-6,6-Difluoro-5-[2-fluoro-5-(4-fluoro-phenylamino)-phenyl]-5,7,7-trimethyl-2,5,6,7-tetrahydro-[1,4]oxazepin-3-ylamine, and
[3-((R)-3-Amino-6,6-difluoro-5-methyl-2,5,6,7-tetrahydro-[1,4]oxazepin-5-yl)-4-fluoro-phenyl]-((S)-3-chloro-6,7-dihydro-5H-[1]pyrindin-7-yl)-amine.

A certain embodiment of the invention provides a process for preparing a compound of formula I as defined herein, which process comprises reacting a compound of formula A20 to produce a compound of formula I

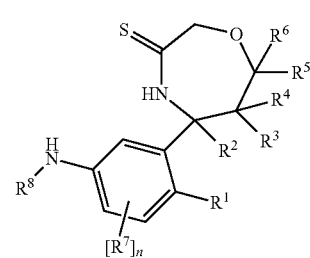

A20 wherein $R^1$, $R^2$, $R^3$, $R^4$, $R^5$, $R^6$, $R^7$, $R^8$ and n are as defined herein.

A certain embodiment of the invention provides a compound of formula I as described herein, whenever prepared by a process as defined above.

A certain embodiment of the invention provides a compound of formula I as described herein for use as therapeutically active substance.

A certain embodiment of the invention provides a compound of formula I as described herein for the use as inhibitor of BACE1 and/or BACE2 activity.

A certain embodiment of the invention provides a compound of formula I as described herein for the use as inhibitor of BACE1 activity.

A certain embodiment of the invention provides a compound of formula I as described herein for the use as inhibitor of BACE2 activity.

A certain embodiment of the invention provides a compound of formula I as described herein for the use as inhibitor of BACE1 and BACE2 activity.

A certain embodiment of the invention provides a compound of formula I as described herein for the use as therapeutically active substance for the therapeutic and/or prophylactic treatment of diseases and disorders characterized by elevated β-amyloid levels and/or β-amyloid oligomers and/or β-amyloid plaques and further deposits or Alzheimer's disease.

A certain embodiment of the invention provides a compound of formula I as described herein for the use as therapeutically active substance for the therapeutic and/or prophylactic treatment of Alzheimer's disease.

A certain embodiment of the invention provides a compound of formula I as described herein for the use as therapeutically active substance for the therapeutic and/or prophylactic treatment of diabetes or type 2 diabetes.

A certain embodiment of the invention provides a compound of formula I as described herein for the use as therapeutically active substance for the therapeutic and/or prophylactic treatment of diabetes.

A certain embodiment of the invention provides a compound of formula I as described herein for the use as therapeutically active substance for the therapeutic and/or prophylactic treatment of Alzheimer's disease, diabetes or type 2 diabetes.

A certain embodiment of the invention provides a compound of formula I as described herein for the use as therapeutically active substance for the therapeutic and/or prophylactic treatment of amyotrophic lateral sclerosis (ALS), arterial thrombosis, autoimmune/inflammatory diseases, cancer such as breast cancer, cardiovascular diseases such as myocardial infarction and stroke, dermatomyositis, Down's Syndrome, gastrointestinal diseases, Glioblastoma multiforme, Graves Disease, Huntington's Disease, inclusion body myositis (IBM), inflammatory reactions, Kaposi Sarcoma, Kostmann Disease, lupus erythematosus, macrophagic myofasciitis, juvenile idiopathic arthritis, granulomatous arthritis, malignant melanoma, multiple mieloma, rheumatoid arthritis, Sjogren syndrome, SpinoCerebellar Ataxia 1, SpinoCerebellar Ataxia 7, Whipple's Disease or Wilson's Disease.

A certain embodiment of the invention provides a pharmaceutical composition comprising a compound of formula I as described herein and a pharmaceutically acceptable carrier and/or a pharmaceutically acceptable auxiliary substance.

A certain embodiment of the invention provides the use of a compound of formula I as described herein for the manufacture of a medicament for the use in inhibition of BACE1 and/or BACE2 activity.

A certain embodiment of the invention provides the use of a compound of formula I as described herein for the manufacture of a medicament for the use in inhibition of BACE1 activity.

A certain embodiment of the invention provides the use of a compound of formula I as described herein for the manufacture of a medicament for the use in inhibition of BACE2 activity.

A certain embodiment of the invention provides the use of a compound of formula I as described herein for the manufacture of a medicament for the use in inhibition of BACE1 and BACE2 activity.

A certain embodiment of the invention provides the use of a compound of formula I as described herein for the manufacture of a medicament for the therapeutic and/or prophylactic treatment of diseases and disorders characterized by elevated β-amyloid levels and/or β-amyloid oligomers and/or β-amyloid plaques and further deposits or Alzheimer's disease.

A certain embodiment of the invention provides the use of a compound of formula I as described herein for the manufacture of a medicament for the therapeutic and/or prophylactic treatment of Alzheimer's disease.

A certain embodiment of the invention provides the use of a compound of formula I as described herein for the manufacture of a medicament for the therapeutic and/or prophylactic treatment of diabetes or type 2 diabetes.

A certain embodiment of the invention provides the use of a compound of formula I as described herein for the manufacture of a medicament for the therapeutic and/or prophylactic treatment of diabetes.

A certain embodiment of the invention provides the use of a compound of formula I as described herein for the manufacture of a medicament for the therapeutic and/or prophylactic treatment of Alzheimer's disease, diabetes or type 2 diabetes.

A certain embodiment of the invention provides a compound of formula I as described herein for the use in inhibition of BACE1 and/or BACE2 activity.

A certain embodiment of the invention provides a compound of formula I as described herein for the use in inhibition of BACE1 activity.

A certain embodiment of the invention provides a compound of formula I as described herein for the use in inhibition of BACE2 activity.

A certain embodiment of the invention provides a compound of formula I as described herein for the use in inhibition of BACE1 and BACE2 activity.

A certain embodiment of the invention provides a compound of formula I as described herein for the use in the therapeutic and/or prophylactic treatment of diseases and disorders characterized by elevated β-amyloid levels and/or β-amyloid oligomers and/or β-amyloid plaques and further deposits or Alzheimer's disease.

A certain embodiment of the invention provides a compound of formula I as described herein for the use in the therapeutic and/or prophylactic treatment of Alzheimer's disease.

A certain embodiment of the invention provides a compound of formula I as described herein for the use in the therapeutic and/or prophylactic treatment of diabetes or type 2 diabetes.

A certain embodiment of the invention provides a compound of formula I as described herein for the use in the therapeutic and/or prophylactic treatment of diabetes.

A certain embodiment of the invention provides a compound of formula I as described herein for the use in the therapeutic and/or prophylactic treatment of Alzheimer's disease, diabetes or type 2 diabetes.

A certain embodiment of the invention provides a method for the use in inhibition of BACE1 and/or BACE2 activity, particularly for the therapeutic and/or prophylactic treatment of diseases and disorders characterized by elevated β-amyloid levels and/or β-amyloid oligomers and/or β-amyloid plaques and further deposits, Alzheimer's disease, diabetes or type 2 diabetes, which method comprises administering compound of formula I as described herein to a human being or animal.

A certain embodiment of the invention provides a method for the use in inhibition of BACE1 and/or BACE2 activity, particularly for the therapeutic and/or prophylactic treatment of amyotrophic lateral sclerosis (ALS), arterial thrombosis, autoimmune/inflammatory diseases, cancer such as breast cancer, cardiovascular diseases such as myocardial infarction and stroke, dermatomyositis, Down's Syndrome, gastrointestinal diseases, Glioblastoma multiforme, Graves Disease, Huntington's Disease, inclusion body myositis (IBM), inflammatory reactions, Kaposi Sarcoma, Kostmann Disease, lupus erythematosus, macrophagic myofasciitis, juvenile idiopathic arthritis, granulomatous arthritis, malignant melanoma, multiple mieloma, rheumatoid arthritis, Sjogren syndrome, SpinoCerebellar Ataxia 1, SpinoCerebellar Ataxia 7, Whipple's Disease or Wilson's Disease, which method comprises administering compound of formula I as described herein to a human being or animal.

A certain embodiment of the invention provides a method for the use in the therapeutic and/or prophylactic treatment of Alzheimer's disease, diabetes or type 2 diabetes, which method comprises administering a compound of formula I as described herein to a human being or animal.

Furthermore, the invention includes all optical isomers, i.e. diastereoisomers, diastereomeric mixtures, racemic mixtures, all their corresponding enantiomers and/or tautomers as well as their solvates of the compounds of formula I.

The skilled person in the art will recognize that the compounds of formula I can exist in tautomeric forms, e.g. in the following tautomeric form:

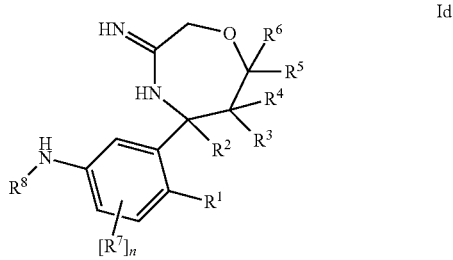

All tautomeric forms are encompassed in the present invention.

The compounds of formula I can contain one or more asymmetric centers and can therefore occur as racemates, racemic mixtures, single enantiomers, diastereomeric mixtures and individual diastereomers. Additional asymmetric centers can be present depending upon the nature of the various substituents on the molecule. Each such asymmetric center will independently produce two optical isomers and it is intended that all of the possible optical isomers and diastereomers in mixtures and as pure or partially purified compounds are included within this invention. The present invention is meant to encompass all such isomeric forms of these compounds. The independent syntheses of these diastereomers or their chromatographic separations can be achieved as known in the art by appropriate modification of the methodology disclosed herein. Their absolute stereochemistry can be determined by the x-ray crystallography of crystalline products or crystalline intermediates which are derivatized, if necessary, with a reagent containing an asymmetric center of known absolute configuration. If desired, racemic mixtures of the compounds can be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. Particular example of isomers of a compound of formula I is a compound of formula Ia, wherein the residues have the meaning as described in any of the embodiments.

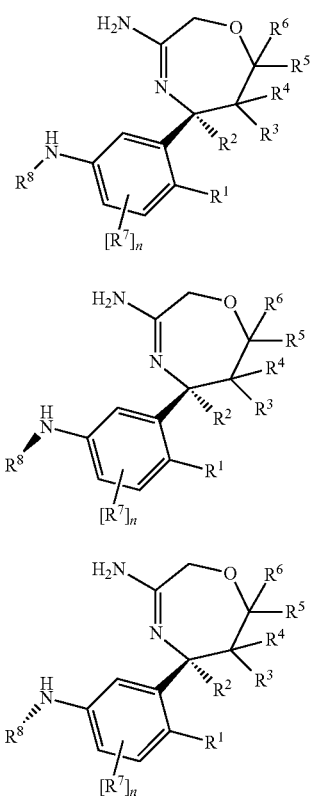

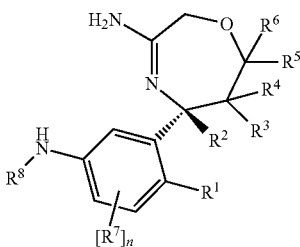

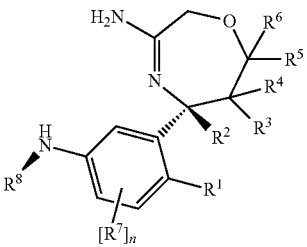

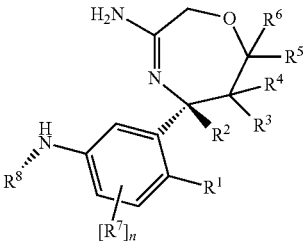

In the embodiments, where optically pure enantiomers are provided, optically pure enantiomer means that the compound contains >90% of the desired isomer by weight, in particular >95% of the desired isomer by weight, or more particular >99% of the desired isomer by weight, said weight percent based upon the total weight of the isomer(s) of the compound. Chirally pure or chirally enriched compounds can be prepared by chirally selective synthesis or by separation of enantiomers. The separation of enantiomers can be carried out on the final product or alternatively on a suitable intermediate.

The compounds of formula I can be prepared in accordance with the following schemes. The starting material is commercially available or can be prepared in accordance with known methods. Any previously defined residues and variables will continue to have the previously defined meaning unless otherwise indicated.

The compounds of formula I can be prepared through a number of synthetic routes for example as illustrated in below schemes. The preparation of compounds of formula I of the present invention can be carried out in sequential or convergent synthetic routes. Syntheses of the compounds of the invention are shown in the following schemes. The skills required for carrying out the reaction and purification of the resulting products are known to those skilled in the art. The substituents and indices used in the following description of the processes have the significance given herein before unless indicated to the contrary.

In more detail, the compounds of formula I can be manufactured by the methods given below, by the methods given in the examples or by analogous methods. Appropriate reaction conditions for the individual reaction steps are known to a person skilled in the art. The reaction sequence is not limited to the one displayed in schemes described below, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

In more detail, compounds of formula I according to the present invention can be prepared by the methods and procedures given below. Some typical procedures for the preparation of compounds of formula I are illustrated in Schemes A ($R^{12}$=H, Br or $NO_2$), A' & A":

Sulfinyl imines of formula A2 can be prepared in analogy to T. P. Tang & J. A. Ellman, J. Org. Chem. 1999, 64, 12, by condensation of an aryl ketone and a sulfinamide, e.g. an alkyl sulfinamide, most particular (R)-(+)-tert-butylsulfinamide in the presence of a Lewis acid such as e.g. a titanium(IV) alkoxide, more particular titanium(IV)ethoxide in a solvent such as an ether, e.g. diethyl ether or more particular THF.

The conversion of the sulfinyl imine A2 to the sulfinamide ester A3 proceeds stereoselectively by the chiral directing group as described by Tang & Ellman. The sulfinyl imine A2 can be reacted with a titanium enolate generated from e.g. an alkyl acetate, in particular ethyl acetate, LDA and chlorotri-isopropoxytitanium at low temperature, particular at −78° C. in a solvent such as an ether, e.g. diethyl ether or more particular THF. Alternatively sulfinamide ester A3 can be produced from sulfinyl imine A2 by Reformatsky reaction of a bromoacetic ester derivative and zinc dust, optionally in the presence of copper(I) chloride, in a solvent such as an ether, e.g. diethyl ether or more particular THF, at temperatures from 0 to 70° C., particular at 23° C.

Sulfinamide ester A3 can be reduced to the alcohol A4 by the reduction of the ethylester with an alkali hydride, particular lithium borohydride or lithium aluminium hydride in a solvent such as an ether, e.g. diethyl ether or more particular THF.

Alkylation of the alcohol A4 to the nitrile A5 can be accomplished with a suitable mild base particular silver(I) oxide in a solvent such as THF or $CH_2Cl_2$, more particular $CH_2Cl_2$ in the presence of an alkylating catalyst such as tetra butyl ammonium iodide.

Hydrolysis of the chiral directing group in the nitrile A5 to give the amino nitrile A6 can be accomplished with a mineral acid, e.g. sulfuric acid or particular hydrochloric acid in a solvent such as an ether, e.g. diethyl ether or more particular 1,4-dioxane.

Aminooxazepine A7 can be prepared by the reaction of amino nitrile A6 and trimethyl aluminium in a solvent such as a xylene, particular toluene.

The protection of the in amino oxazine A7 to give A8 can be accomplished with a triphenylmethyl protecting group, in particular 4,4'-dimethoxytrityl and a base, e.g an alkyl amine, particular triethyl amine in an inert solvent such as dichloromethane.

The conversion of the bromophenyl compound A8 to the diphenylmethyl imine A9 can be effected with an imine, e.g. benzophenone imine and a base, e.g. a metal alkoxide or more particular sodium t-butoxide and a palladium complex, e.g. 2-di-t-butylphosphino-2',4',6'-triisopropylbiphenyl and tris (dibenzylideneacetone)dipalladium chloroform adduct in a solvent such as a benzene derivative, e.g. toluene.

Global deprotection of the imine A9 to the aniline A10 can be accomplished in a two step procedure involving a strong carbonic acid, e.g. trifluoroacetic acid in a halogenated solvent, e.g. dichloromethane followed by addition of a mineral acid, e.g. hydrochloric acid in a water soluble solvent, e.g. dioxane.

Introduction of the nitro group in A7 ($R^{12}$=H) to give A11 was best performed according to the standard procedure involving sulfuric acid and nitric acid at low temperature, particular at 0° C.

Aminooxazepine A11 can be prepared by the reaction of amino nitrile A6 (for $R^{12}$=$NO_2$) and trimethyl aluminium in a solvent such as a xylene, particular toluene.

The reduction of the nitro group in aminooxazepine A11 to the aniline A10 can be accomplished by hydrogenation using a catalyst such as Pd/C in protic solvents, such as alcohols, in particular ethanol or methanol or by metal reduction such as iron or tin, more particular tin chloride in alcohol, more particular aqueous ethanol at elevated temperature, more particular 80° C.

Target amines Ia can be prepared via reductive amination of aniline A10 performed with a borohydride as the reducing agent, e.g. sodium borohydride, particular sodium triacetoxyborohydride and a weak acid, e.g. acetic acid in a solvent such as tetrahydrofuran or dichloromethane.

The benzophenone imine in compounds of formula A9 can be hydrolyzed to the aniline A12 by reacting it with diluted aqueous mineral acid, like e.g. hydrochloric acid, in a water soluble solvent such as tetrahydrofuran or dioxane.

The conversion of the aniline A12 to the N-arylated or N-heteroarylated aniline A13 can be effected with an aryl- or heteroaryl bromide, chloride or triflate and a base, e.g. a metal alkoxide or more particular sodium t-butoxide and a palladium complex, e.g. 2-di-t-butylphosphino-2',4',6'-triisopropylbiphenyl and tris(dibenzylideneacetone)dipalladium chloroform adduct in a solvent such as a benzene derivative, e.g. toluene. Alternatively the N-arylated or N-heteroarylated aniline A13 can be prepared by reacting a bromophenyl compound of formula A8 with an aryl- or heteroaryl-amine $R^7$—$NH_2$ under the same conditions as used for the conversion of A12 to A13.

Deprotection of the dimethoxytrityl protected amine A13 to the target amine Ia can be accomplished involving a strong carbonic acid, e.g. trifluoroacetic acid in a halogenated solvent, e.g. dichloromethane.

Scheme A

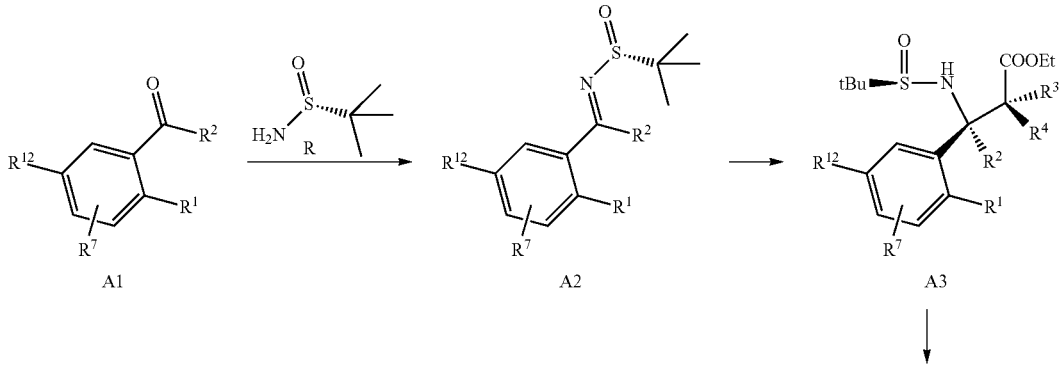

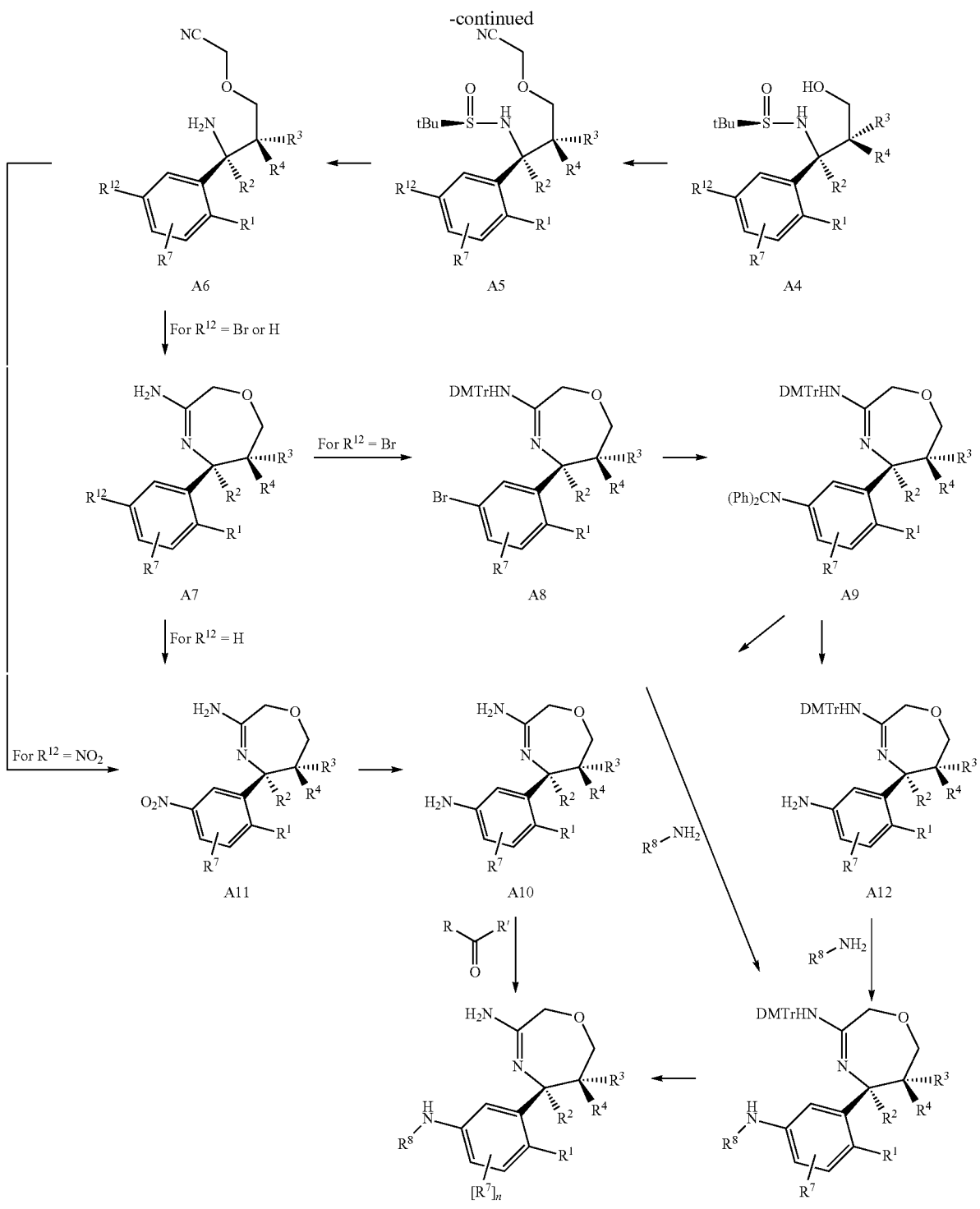

DMTr: 4,4'-dimethoxytrityl
R = C1-6-alkyl, aryl, heteroaryl
R' = C1-6-alkyl

Sulfinamide ester A3 can be transformed into alcohol A4 by the reaction of the ethylester with an excess of a Grignard or an organolithium reagent, e.g. methyl- or ethylmagnesium halide, methyllithium etc., in a solvent such as an ether, e.g. diethyl ether or more particular THF, at temperatures between −78 and 70° C., particular at 0 to 23° C.

Hydrolysis of the chiral directing group in the alcohol A4 to give the amino alcohol A14 can be accomplished with a mineral acid, e.g. sulfuric acid or particular hydrochloric acid in a solvent such as an ether, e.g. diethyl ether or THF, more particular 1,4-dioxane, at temperatures from 0 to 23° C.

Haloacetamide A15, where X is chlorine or bromine, can be prepared by selective acylation of the amino group in amino alcohol A14 with an acid chloride, such as chloro- or bromoacetyl chloride, under biphasic conditions with a suitable mild base, like e.g. saturated aqueous solutions of sodium or potassium hydrogencarbonate, in a solvent such as toluene, ethyl acetate or $CH_2Cl_2$, more particular $CH_2Cl_2$ at temperatures between 0 and 23° C.

Cyclization of the haloacetamide A15 to the lactam A16 can be accomplished by reacting it with a strong base, such as potassium tert-butoxide or potassium tert-amylate, in a solvent such as tert-butanol or tert-amylalcohol, toluene or THF, particular toluene, at temperatures between 0 and 70° C., particular at 23° C.

The conversion of the bromophenyl compounds A8 or A16 to the diphenylmethyl imines A9 or A17 can be effected with an imine, e.g benzophenone imine and a base, e.g a metal alkoxide or more particular sodium t-butoxide and a palladium complex, e.g. 2-di-t-butylphosphino-2',4',6'-triisopropylbiphenyl and tris(dibenzylideneacetone)dipalladium chloroform adduct in a solvent such as a benzene derivative, e.g. toluene, at temperatures between 80 and 120° C., particular between 90 and 110° C.

The lactam A17 or A22 can be converted into the thiolactam A18 or A20 by reaction with 2,4-bis-(4-methoxy-phenyl)-[1,3,2,4]dithiadiphosphetane 2,4-disulfide (Lawesson's reagent) or phosphorous pentasulfide in an ether solvent such as THF, 1,2-dimethoxyethane or 1,4-dioxane, particular 1,4-dioxane, at temperatures between 23 and 100° C., particular between 50 and 80° C.

The arylated benzophenone imine moiety in the thiolactam A18 can be hydrolyzed to the aniline A19 by aqueous mineral acid such as sulfuric or hydrochloric acid, particular hydrochloric acid, in an ether solvent such as THF, 1,2-dimethoxyethane or 1,4-dioxane, particular 1,4-dioxane, at temperatures between 0 and 23° C., particular at 23° C. The formation of the thiolactam A18 and the following hydrolysis can be conveniently performed in one reaction vessel to yield the aniline A19 directly.

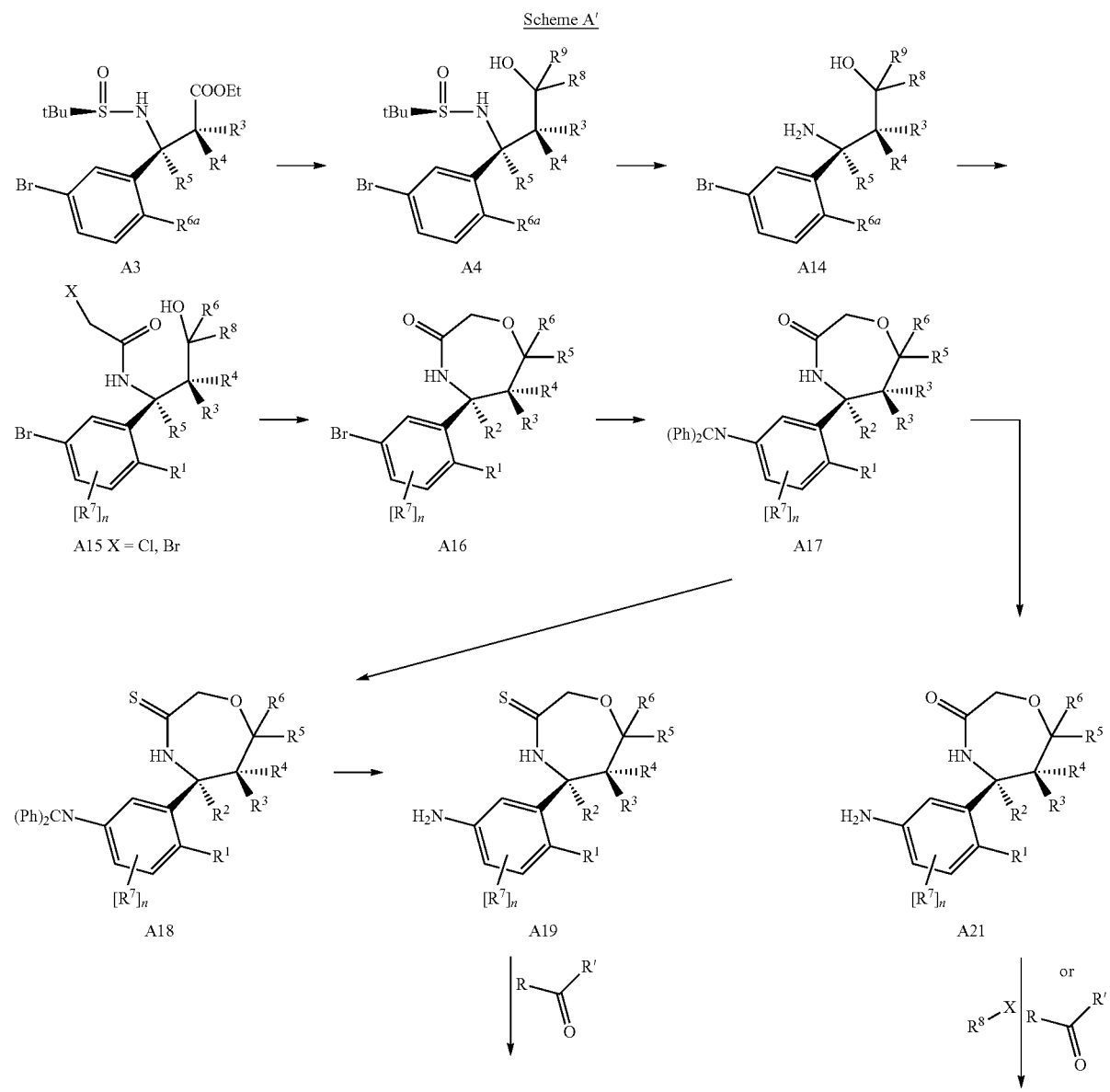

Scheme A'

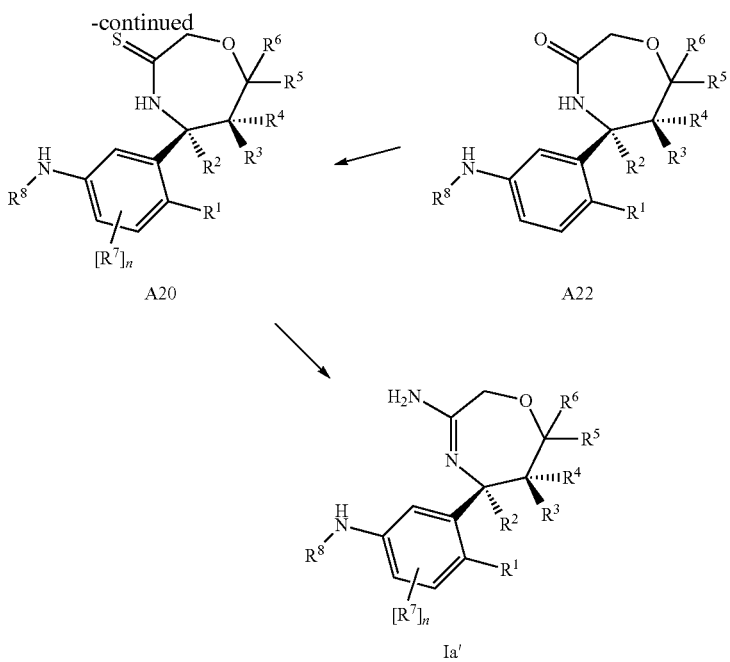

R = C1-6-alkyl, aryl, heteroaryl
R' = C1-6-alkyl

Alkylated anilines A20 or A22 can be prepared via reductive amination of anilines A19 or A21 performed with a borohydride as the reducing agent, e.g. sodium borohydride, particular sodium triacetoxyborohydride and a weak acid, e.g. acetic acid in a solvent such as tetrahydrofuran or dichloromethane. Alternatively, anilines A19 or A21 can be reductively aminated with decaborane in a solvent such as methanol to give the alkylated anilines A20 or A22.

The conversion of the aniline A21 to the N-arylated or N-heteroarylated aniline A22 can be effected with an aryl- or heteroaryl bromide, chloride or triflate and a base, e.g. a metal alkoxide or more particular sodium t-butoxide and a palladium complex, e.g. 2-di-t-butylphosphino-2',4',6'-triisopropylbiphenyl and tris(dibenzylideneacetone)dipalladium chloroform adduct in a solvent such as a benzene derivative, e.g. toluene.

The target amines Ia' can be prepared from the thiolactams A20 by reaction with an solution of ammonia in a protic solvent such as methanol, ethanol or water, particular methanol, with or without presence of a mild oxidant such as tert-butylhydroperoxide at temperatures between 0 and 60° C., particular at 23° C. in the presence of an oxidant or at 50 to 60° C. in the absence of an oxidant.

Compounds of formula A23 can be prepared by selective O-allylation by reacting the alcohol of the formula A4 with allyl tert-butyl carbonate [CAS no. 70122-89-3] in the presence of catalytic amounts of a palladium(II) salt, like e.g. palladium(II) acetate, and a phosphine ligand, like e.g. triphenylphosphine, or with a palladium(0) catalyst, like e.g. tetrakistriphenylphosphinepalladium(0), in a solvent such as e.g. tetrahydrofuran or dioxane at temperatures between 23 and 100° C., particular at 50 to 80° C. as described by Haight, A. R.; Stoner, E. J.; Peterson, M. J.; Grover, V. K.; in *J. Org. Chem.* 2003, 68 (21), 8092 (DOI: 10.1021/jo0301907).

The acids of formula A24 can be prepared by oxidation of the O-allyl ethers of formula A23 by reacting it with a periodate salt, such as sodium or potassium periodate, in the presence of a catalytic amount of a ruthenium salt, such as e.g. ruthenium(III) chloride, in a solvent mixture consisting of ethyl acetate or tetrachloromethane, acetonitrile and water at temperatures between 0 and 40° C., particular 20 to 30° C. These reaction conditions will cause concomitant oxidation of the tert-butylsulfinic acid amide into the corresponding tert-butylsulfonic acid amide.

The acids of formula A24 can be converted into the ethyl esters of formula A25 by treatment with thionyl chloride in ethanol at temperatures between 23 and 80° C.

The amino esters of formula A26 can be prepared by cleavage of the tert-butylsulfonic acid amide in compounds of formula A25 by treatment with a strong acid, particular trifluoromethanesulfonic acid, in a chlorinated solvent, such as e.g. dichloromethane, at temperatures between 0 and 30° C., particular at 23° C. This method has been described by Sun P., Weinreb S. M., Shang M. in *J. Org. Chem.* 1997, 62(24), 8604.

Cyclization of the amino esters of formula A26 to the lactams of formula A16 can be achieved by the reaction with trimethyl aluminium in a solvent such as a xylene, particular toluene, at temperatures between 0 and 100° C., in particular 23° C.

Scheme A''

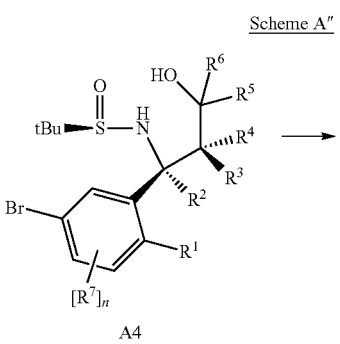

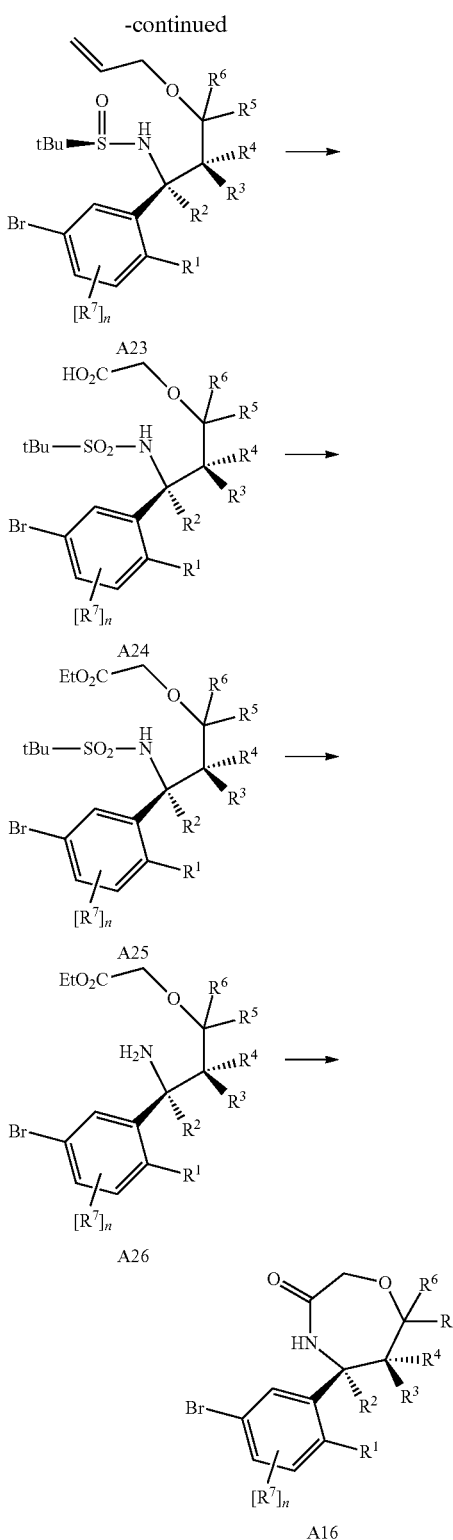

The corresponding pharmaceutically acceptable salts with acids can be obtained by standard methods known to the person skilled in the art, e.g. by dissolving the compound of formula I in a suitable solvent such as e.g. dioxane or tetrahydrofuran and adding an appropriate amount of the corresponding acid. The products can usually be isolated by filtration or by chromatography. The conversion of a compound of formula I into a pharmaceutically acceptable salt with a base can be carried out by treatment of such a compound with such a base. One possible method to form such a salt is e.g. by addition of 1/n equivalents of a basic salt such as e.g. $M(OH)_n$, wherein M=metal or ammonium cation and n=number of hydroxide anions, to a solution of the compound in a suitable solvent (e.g. ethanol, ethanol-water mixture, tetrahydrofuran-water mixture) and to remove the solvent by evaporation or lyophilization. Particular salts are hydrochloride, formate and trifluoroacetate.

Insofar as their preparation is not described in the examples, the compounds of formula I as well as all intermediate products can be prepared according to analogous methods or according to the methods set forth herein. Starting materials are commercially available, known in the art or can be prepared by methods known in the art or in analogy thereto.

It will be appreciated that the compounds of formula I in this invention can be derivatized at functional groups to provide derivatives which are capable of conversion back to the parent compound in vivo.

Pharmacological Tests

The compounds of formula I and their pharmaceutically acceptable salts possess valuable pharmacological properties. Compounds of the present invention are associated with inhibition of BACE1 and/or BACE2 activity. The compounds were investigated in accordance with the test given hereinafter.

Cellular Aβ-Lowering Assay:

Human HEK293 cells which are stably transfected with a vector expressing a cDNA of the human APP wt gene (APP695) were used to assess the potency of the compounds in a cellular assay. The cells were seeded in 96-well microtiter plates in cell culture medium (Iscove, plus 10% (v/v) fetal bovine serum, glutamine, penicillin/streptomycin) to about 80% confluence and the compounds were added at a 10× concentration in 1/10 volume of medium without FCS containing 8% DMSO (final concentration of DMSO was kept at 0.8% v/v). After 18-20 hrs incubation at 37° C. and 5% $CO_2$ in a humidified incubator the culture supernatant was harvested for the determination of Aβ40 concentrations. 96 well ELISA plates (e.g., Nunc MaxiSorb) were coated with monoclonal antibody which specifically recognize the C-terminal end of Aβ40 (Brockhaus et al., NeuroReport 9, 1481-1486; 1998). After blocking of non-specific binding sites with e.g. 1% BSA and washing, the culture supernatants were added in suitable dilutions together with a horseradish peroxidase-coupled Aβ detection antibody (e.g., antibody 4G8, Senetek, Maryland Heights, Mo.) and incubated for 5 to 7 hrs. Subsequently the wells of the microtiter plate were washed extensively with Tris-buffered saline containing 0.05% Tween 20 and the assay was developed with tetramethylbenzidine/ $H_2O_2$ in citric acid buffer. After stopping the reaction with one volume $1NH_2SO_4$ the reaction was measured in an ELISA reader at 450 nm wavelength. The concentrations of Aβ in the culture supernatants were calculated from a standard curve obtained with known amounts of pure Aβ peptide.

Immunofluorescence Resonance Energy Transfer (FRET) Assay for BACE2 Inhibition:

BACE2 enzyme ectodomain (derived from plasmid "pET17b-T7-hu proBACE2") was prepared as described in Ostermann et al., "Crystal Structure of Human BACE2 in Complex with a Hydroxyethylamine Transition-state Inhibitor", Journal of Molecular Biology 2006, 355, 249-261. The pro-enzyme was stored at 4° C. at a concentration of 70 μg/ml.

The FRET assay was performed essentially as described in Grüninger-Leitch et al., Journal of Biological Chemistry (2002) 277(7) 4687-93 ("Substrate and inhibitor profile of BACE (beta-secretase) and comparison with other mammalian aspartic proteases"). In summary, a peptide is designed that is cleaved by the protease. The peptide is labelled with dabcyl at the N terminus and Lucifer Yellow at the C-terminus, such that for an intact peptide the Lucifer Yellow fluorescence is quenched by the dabcyl. When the peptide is cut by BACE2, the quenching is removed and a fluorescent signal is generated.

The assay was performed as described in Grueninger et al. 2002 at pH 4.5 using a substrate concentration of 5 μM. A FRET peptide based on the TMEM27 sequence was devised. dabcyl-QTLEFLKIPS-LucY (SEQ ID NO: 1). BACE2 had a high activity against this sequence, which is unrelated to the known APP-based substrates. Conversely, BACE1 had insignificant activity against this peptide.

The assay readout is the initial rate of change of fluorescence intensity giving a relative measure of BACE2 activity. Small values correspond to high inhibition and larger values to low inhibition. To determine $IC_{50}$ values (i.e. the concentration inhibiting the enzyme activity by 50%) of the compound for BACE2, typically, 12 assays were made with a range of concentrations chosen empirically to give low, high and intermediate inhibition of the protease. $IC_{50}$ values were determined using these assay values generated for a range of inhibitor concentrations and the curve fitting software XLfit (IDBS) using the Sigmoidal Dose-Response Model.

The exemplified compounds according to formula I have an inhibitory activity in the above assay ($IC_{50}$) particular of 5 nM to 50 μM, more particular of 5 nM to 1 μM.

TABLE 1

$IC_{50}$ values of selected examples

| Ex. | Structure | BACE1 $IC_{50}$ [μM] | BACE2 $IC_{50}$ [μM] |
| --- | --- | --- | --- |
| 1 | 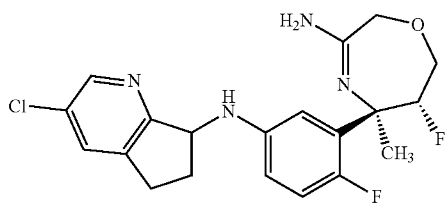 [SMILES: C[C@]1(c2cc(NC3CCc4cc(Cl)cnc43)ccc2F)N=C(N)COC[C@@H]1F] | 0.070 | 0.024 |
| 2 | 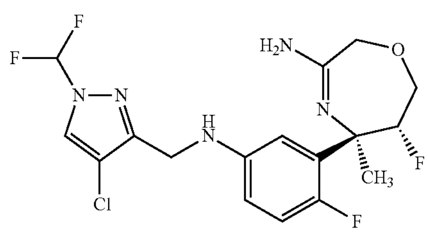 [SMILES: C[C@]1(c2cc(NCc3nn(C(F)F)cc3Cl)ccc2F)N=C(N)COC[C@@H]1F] | 0.040 | 0.035 |
| 3 | 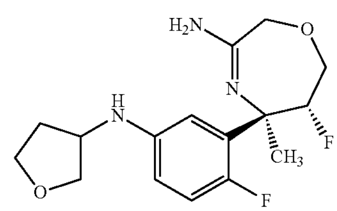 [SMILES: C[C@]1(c2cc(NC3CCOC3)ccc2F)N=C(N)COC[C@@H]1F] | 0.580 | 0.072 |
| 4 | 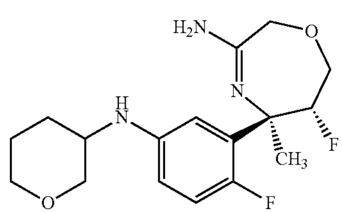 [SMILES: C[C@]1(c2cc(NC3CCCOC3)ccc2F)N=C(N)COC[C@@H]1F] | 0.400 | 0.073 |
| 5 | 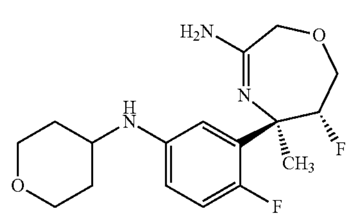 [SMILES: C[C@]1(c2cc(NC3CCOCC3)ccc2F)N=C(N)COC[C@@H]1F] | 2.400 | 1.480 |

TABLE 1-continued

IC₅₀ values of selected examples

| Ex. | Structure | BACE1 IC$_{50}$ [µM] | BACE2 IC$_{50}$ [µM] |
|---|---|---|---|
| 6 | 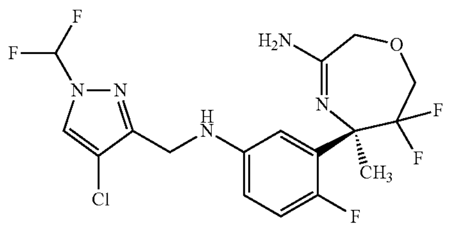 [SMILES: C[C@]1(c2cc(NCc3nn(C(F)F)cc3Cl)ccc2F)N=C(N)COCC1(F)F] | 0.030 | 0.011 |
| 7 | 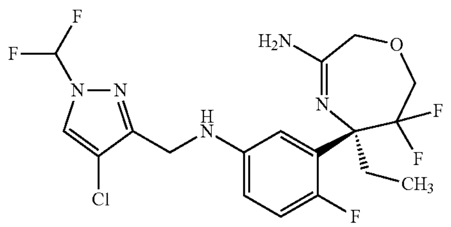 [SMILES: CC[C@]1(c2cc(NCc3nn(C(F)F)cc3Cl)ccc2F)N=C(N)COCC1(F)F] | 0.170 | 0.310 |
| 8 | 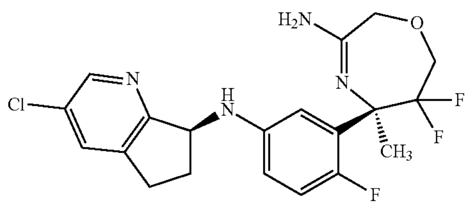 [SMILES: C[C@]1(c2cc(N[C@H]3CCc4cc(Cl)cnc43)ccc2F)N=C(N)COCC1(F)F] | 0.090 | 0.030 |
| 9 | 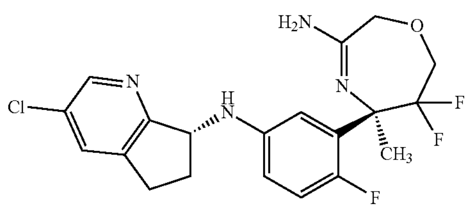 [SMILES: C[C@]1(c2cc(N[C@@H]3CCc4cc(Cl)cnc43)ccc2F)N=C(N)COCC1(F)F] | 2.100 | 0.650 |
| 10 | 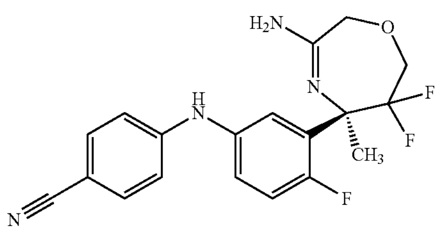 [SMILES: C[C@]1(c2cc(Nc3ccc(C#N)cc3)ccc2F)N=C(N)COCC1(F)F] | 0.700 | 0.910 |
| 12 | 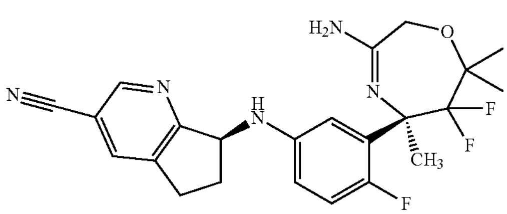 [SMILES: CC1(C)OCC(N)=N[C@](C)(c2cc(N[C@H]3CCc4cc(C#N)cnc43)ccc2F)C1(F)F] | 0.120 | 0.005 |
| 13 | 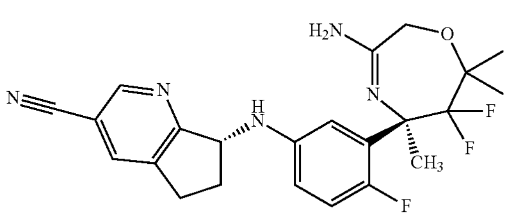 [SMILES: CC1(C)OCC(N)=N[C@](C)(c2cc(N[C@@H]3CCc4cc(C#N)cnc43)ccc2F)C1(F)F] | 0.310 | 0.095 |

TABLE 1-continued

IC$_{50}$ values of selected examples

| Ex. | Structure | BACE1 IC$_{50}$ [µM] | BACE2 IC$_{50}$ [µM] |
| --- | --- | --- | --- |
| 14 | 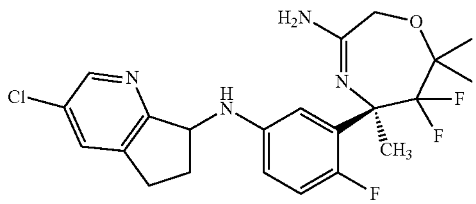 [SMILES: CC1(C)OCC(N)=N[C@](C)(c2cc(NC3CCc4cc(Cl)cnc43)ccc2F)C1(F)F] | 0.071 | 0.028 |
| 15 | 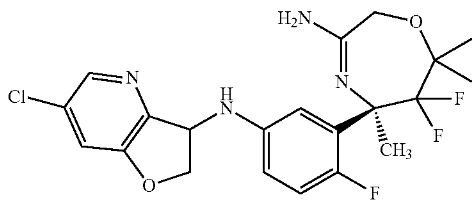 [SMILES: CC1(C)OCC(N)=N[C@](C)(c2cc(NC3COc4cc(Cl)cnc43)ccc2F)C1(F)F] | 0.040 | 0.058 |
| 16 | 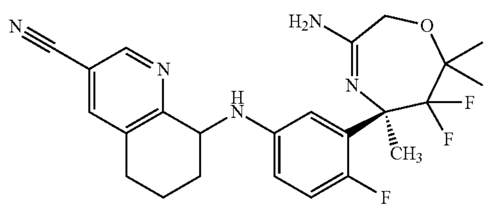 [SMILES: CC1(C)OCC(N)=N[C@](C)(c2cc(NC3CCCc4cc(C#N)cnc43)ccc2F)C1(F)F] | 0.120 | 0.133 |
| 17 | 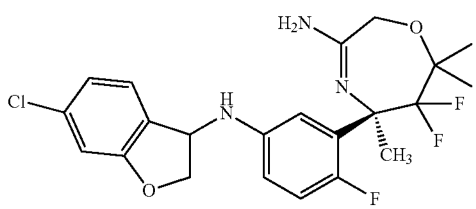 [SMILES: CC1(C)OCC(N)=N[C@](C)(c2cc(NC3COc4cc(Cl)ccc43)ccc2F)C1(F)F] | 0.320 | 0.400 |
| 18 | 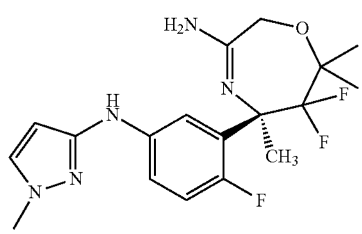 [SMILES: Cn1ccc(Nc2ccc(F)c([C@@]3(C)N=C(N)COC(C)(C)C3(F)F)c2)n1] | 0.240 | 0.530 |
| 19 | 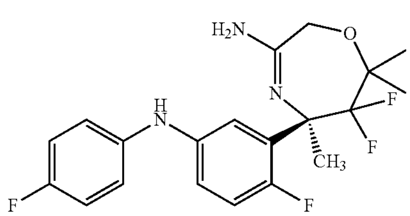 [SMILES: CC1(C)OCC(N)=N[C@](C)(c2cc(Nc3ccc(F)cc3)ccc2F)C1(F)F] | 0.310 | 4.160 |
| 20 | 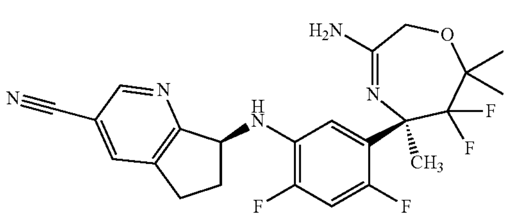 [SMILES: CC1(C)OCC(N)=N[C@](C)(c2cc(N[C@H]3CCc4cc(C#N)cnc43)c(F)cc2F)C1(F)F] | 1.900 | 0.170 |

TABLE 1-continued

| Ex. | Structure | BACE1 IC$_{50}$ [µM] | BACE2 IC$_{50}$ [µM] |
|---|---|---|---|
| 21 | 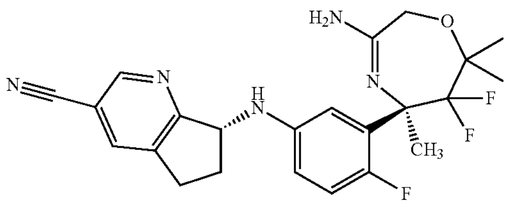 [SMILES: CC1(C)OCC(N)=N[C@](C)(c2cc(N[C@@H]3CCc4cc(C#N)cnc43)ccc2F)C1(F)F] | 14.000 | 2.810 |
| 22 | 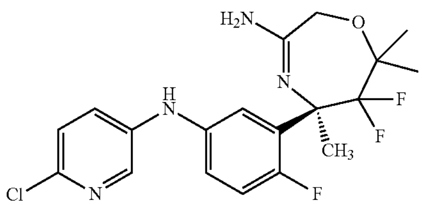 [SMILES: CC1(C)OCC(N)=N[C@](C)(c2cc(Nc3ccc(Cl)nc3)ccc2F)C1(F)F] | 0.370 | 1.770 |
| 23 | 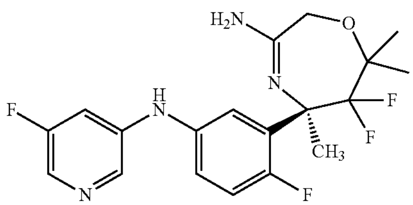 [SMILES: CC1(C)OCC(N)=N[C@](C)(c2cc(Nc3cncc(F)c3)ccc2F)C1(F)F] | 0.440 | 1.360 |
| 24 | 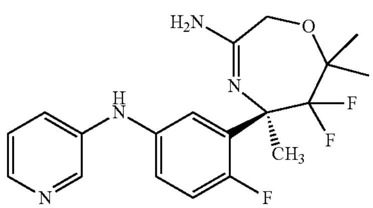 [SMILES: CC1(C)OCC(N)=N[C@](C)(c2cc(Nc3cccnc3)ccc2F)C1(F)F] | 1.100 | 0.940 |
| 25 | 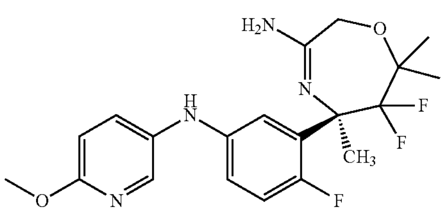 | 0.410 | 1.630 |
| 26 | 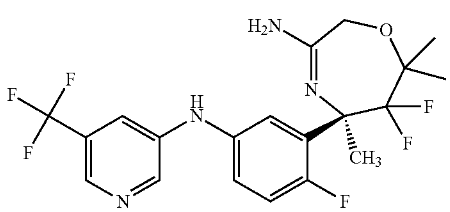 [SMILES: CC1(C)OCC(N)=N[C@](C)(c2cc(Nc3cncc(C(F)(F)F)c3)ccc2F)C1(F)F] | 1.900 | 3.890 |
| 27 | 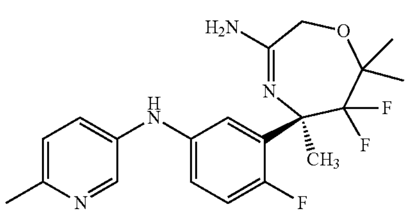 | 5.900 | |

TABLE 1-continued

IC$_{50}$ values of selected examples

| Ex. | Structure | BACE1 IC$_{50}$ [μM] | BACE2 IC$_{50}$ [μM] |
|---|---|---|---|
| 28 | 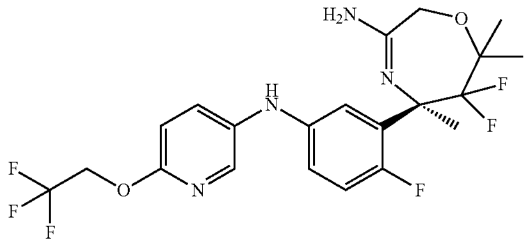 [SMILES: CC1(C)OCC(N)=N[C@](C)(c2cc(Nc3ccc(OCC(F)(F)F)nc3)ccc2F)C1(F)F] | 12.700 | 1.493 |

Pharmaceutical Compositions

The compounds of formula I and the pharmaceutically acceptable salts can be used as therapeutically active substances, e.g. in the form of pharmaceutical compositions. The pharmaceutical compositions can be administered orally, e.g. in the form of tablets, coated tablets, dragées, hard and soft gelatin capsules, solutions, emulsions or suspensions. The administration can, however, also be effected rectally, e.g. in the form of suppositories, or parenterally, e.g. in the form of injection solutions.

The compounds of formula I and the pharmaceutically acceptable salts thereof can be processed with pharmaceutically inert, inorganic or organic carriers for the production of pharmaceutical compositions. Lactose, corn starch or derivatives thereof, talc, stearic acids or its salts and the like can be used, for example, as such carriers for tablets, coated tablets, dragées and hard gelatin capsules. Suitable carriers for soft gelatin capsules are, for example, vegetable oils, waxes, fats, semi-solid and liquid polyols and the like. Depending on the nature of the active substance no carriers are however usually required in the case of soft gelatin capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical compositions can, moreover, contain pharmaceutically acceptable auxiliary substances such as preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Pharmaceutical compositions containing a compound of formula I or a pharmaceutically acceptable salt thereof and a therapeutically inert carrier are also provided by the present invention, as is a process for their production, which comprises bringing one or more compounds of formula I and/or pharmaceutically acceptable salts thereof and, if desired, one or more other therapeutically valuable substances into a galenical administration form together with one or more therapeutically inert carriers.

The dosage at which compounds of the invention can be administered can vary within wide limits and will, of course, have to be adjusted to the individual requirements in each particular case. In the case of oral administration the dosage for adults can vary from about 0.01 mg to about 1000 mg per day of a compound of formula I or of the corresponding amount of a pharmaceutically acceptable salt thereof. The daily dosage can be administered as single dose or in divided doses and, in addition, the upper limit can also be exceeded when this is found to be indicated.

The following examples illustrate the present invention without limiting it, but serve merely as representative thereof. The pharmaceutical preparations conveniently contain about 1-500 mg, particular 1-100 mg, of a compound of formula I. Examples of compositions according to the invention are:

Example A

Tablets of the following composition are manufactured in the usual manner:

TABLE 2 possible tablet composition

| ingredient | mg/tablet | | | |
|---|---|---|---|---|
| | 5 | 25 | 100 | 500 |
| Compound of formula I | 5 | 25 | 100 | 500 |
| Lactose Anhydrous DTG | 125 | 105 | 30 | 150 |
| Sta-Rx 1500 | 6 | 6 | 6 | 60 |
| Microcrystalline Cellulose | 30 | 30 | 30 | 450 |
| Magnesium Stearate | 1 | 1 | 1 | 1 |
| Total | 167 | 167 | 167 | 831 |

Manufacturing Procedure
1. Mix ingredients 1, 2, 3 and 4 and granulate with purified water.
2. Dry the granules at 50° C.
3. Pass the granules through suitable milling equipment.
4. Add ingredient 5 and mix for three minutes; compress on a suitable press.

Example B-1

Capsules of the following composition are manufactured:

TABLE 3 possible capsule ingredient composition

| ingredient | mg/capsule | | | |
|---|---|---|---|---|
| | 5 | 25 | 100 | 500 |
| Compound of formula I | 5 | 25 | 100 | 500 |
| Hydrous Lactose | 159 | 123 | 148 | — |
| Corn starch | 25 | 35 | 40 | 70 |
| Talc | 10 | 15 | 10 | 25 |
| Magnesium Stearate | 1 | 2 | 2 | 5 |
| Total | 200 | 200 | 300 | 600 |

Manufacturing Procedure
1. Mix ingredients 1, 2 and 3 in a suitable mixer for 30 minutes.
2. Add ingredients 4 and 5 and mix for 3 minutes.
3. Fill into a suitable capsule.

The compound of formula I, lactose and corn starch are firstly mixed in a mixer and then in a comminuting machine. The mixture is returned to the mixer; the talc is added thereto and mixed thoroughly. The mixture is filled by machine into suitable capsules, e.g. hard gelatin capsules.

Example B-2

Soft Gelatin Capsules of the following composition are manufactured:

TABLE 4 possible soft gelatin capsule ingredient composition

| ingredient | mg/capsule |
| --- | --- |
| Compound of formula I | 5 |
| Yellow wax | 8 |
| Hydrogenated Soya bean oil | 8 |
| Partially hydrogenated plant oils | 34 |
| Soya bean oil | 110 |
| Total | 165 |

TABLE 5 possible soft gelatin capsule composition

| ingredient | mg/capsule |
| --- | --- |
| Gelatin | 75 |
| Glycerol 85% | 32 |
| Karion 83 | 8 (dry matter) |
| Titan dioxide | 0.4 |
| Iron oxide yellow | 1.1 |
| Total | 116.5 |

Manufacturing Procedure

The compound of formula I is dissolved in a warm melting of the other ingredients and the mixture is filled into soft gelatin capsules of appropriate size. The filled soft gelatin capsules are treated according to the usual procedures.

Example C

Suppositories of the Following Composition are Manufactured:

TABLE 6 possible suppository composition

| ingredient | mg/supp. |
| --- | --- |
| Compound of formula I | 15 |
| Suppository mass | 1285 |
| Total | 1300 |

Manufacturing Procedure

The suppository mass is melted in a glass or steel vessel, mixed thoroughly and cooled to 45° C. Thereupon, the finely powdered compound of formula I is added thereto and stirred until it has dispersed completely. The mixture is poured into suppository moulds of suitable size, left to cool; the suppositories are then removed from the moulds and packed individually in wax paper or metal foil.

Example D

Injection solutions of the following composition are manufactured:

TABLE 7 possible injection solution composition

| ingredient | mg/injection solution. |
| --- | --- |
| Compound of formula I | 3 |
| Polyethylene Glycol 400 | 150 |
| acetic acid | q.s. ad pH 5.0 |
| water for injection solutions | ad 1.0 ml |

Manufacturing Procedure

The compound of formula I is dissolved in a mixture of Polyethylene Glycol 400 and water for injection (part). The pH is adjusted to 5.0 by acetic acid. The volume is adjusted to 1.0 ml by addition of the residual amount of water. The solution is filtered, filled into vials using an appropriate overage and sterilized.

Example E

Sachets of the following composition are manufactured:

TABLE 8 possible sachet composition

| ingredient | mg/sachet |
| --- | --- |
| Compound of formula I | 50 |
| Lactose, fine powder | 1015 |
| Microcrystalline cellulose (AVICEL PH 102) | 1400 |
| Sodium carboxymethyl cellulose | 14 |
| Polyvinylpyrrolidon K 30 | 10 |
| Magnesium stearate | 10 |
| Flavoring additives | 1 |
| Total | 2500 |

Manufacturing Procedure

The compound of formula I is mixed with lactose, microcrystalline cellulose and sodium carboxymethyl cellulose and granulated with a mixture of polyvinylpyrrolidone in water. The granulate is mixed with magnesium stearate and the flavoring additives and filled into sachets.

EXPERIMENTAL PART

The following examples are provided for illustration of the invention. They should not be considered as limiting the scope of the invention, but merely as being representative thereof.

General:

MS: Mass spectra (MS) were measured either with ion spray positive or negative (ISP or ISN) method on a Perkin-Elmer SCIEX API 300 or with electron impact method (EI, 70 eV) on a Finnigan MAT SSQ 7000 spectrometer.

Abbreviations:

DCC=N,N'-diisopropyl-carbodiimide, DCE=1,2-dichloroethane, DCM=dichloromethane, DIPEA=diisopropylethylamine, DMAc=dimethylacetamide, DMAP=4-dimethylaminopyridine, DMF=N,N-dimethylformamide, DMSO=dimethyl sulfoxide, EDCI=N-(3-dimethylaminopropyl)-N'-ethyl-carbodiimide hydrochloride, HATU=1-[bis(dimethylamino)methylene]-1H-1,2,3-triazolo[4,5-b]pyridinium-3-oxide hexafluorophosphate, HCl=hydrogen chloride, HPLC=high performance liquid chromatography, LDA=lithium diisopropylamide, MS=mass spectrum, NMR=nuclear magnetic resonance, TEA=triethylamine, TBME=tert-butyl methyl ether, and THF=tetrahydrofuran.

Synthesis of the intermediate
1-(2-fluoro-5-nitro-phenyl)-propan-1-one A1A

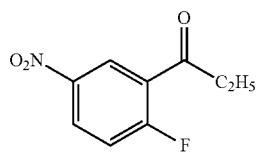 [SMILES: CCC(=O)c1cc([N+](=O)[O-])ccc1F]

To a solution of the 1-(2-fluoro-phenyl)-propan-1-one (99 mmol) in concentrated sulfuric acid (80 ml) cooled down to −30° C. was added slowly fuming nitric acid (8 ml) over 20 min and the solution was stirred at −30° C. for 15 min. The mixture was slowly poured into a stirred mixture of 200 ml of water and 400 g ice. The aqueous phase was extracted with ethyl acetate, the organic layer was extracted again with water and aqueous NaHCO$_3$ 1M. The organic layer was dried over Na$_2$SO$_4$, evaporated and the residue was purified by chromatography on silica using a mixture of heptane and ethylacetate as eluent to afford the pure nitro intermediate J. MS (ISP): m/z=198.1 [M+H]+.

Synthesis of the Intermediate Sulfinyl Imines A2

General Procedure

To a solution of the (R)-(+)-tert-butylsulfinamide (66 mmol) in THF (350 ml) was added subsequently the ketone A1 (72.6 mmol) and titanium(IV)ethoxide (132 mmol) and the solution was stirred at reflux temperature for 5 h. The mixture was cooled to 22° C., treated with brine (400 ml), the suspension was stirred for 10 min and filtered over dicalite. The layers were separated, the aqueous layer was extracted with ethyl acetate, the combined organic layers were washed with water, dried and concentrated in vacuo. The residue was purified by chromatography on silica using cylohexane/ethyl acetate to give the pure sulfinyl imine A2.

Intermediate A2A

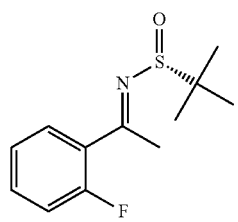 [SMILES: C/C(=N\[S@](=O)C(C)(C)C)c1ccccc1F]

Starting from 1-(2-fluorophenyl)-ethanone, the product (R)-2-methyl-propane-2-sulfinic acid [1-(2-fluorophenyl)-(E)-ethylidene]-amide was obtained as pale brown oil. MS (ISP): m/z=242.3 [M+H]+.

Intermediate A2B

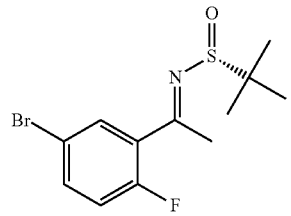 [SMILES: C/C(=N\[S@](=O)C(C)(C)C)c1cc(Br)ccc1F]

Starting from commercially available 1-(2-fluoro-5-bromo-phenyl)-ethanone [CAS No. 477-89-3], the product (R)-2-methyl-propane-2-sulfinic acid [1-(2-fluoro-5-bromo-phenyl)-(E)-ethylidene]-amide was obtained as a pale red oil. MS (ISP): m/z=320.3 [M+H]+.

Intermediate A2C

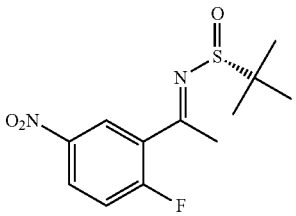 [SMILES: C/C(=N\[S@](=O)C(C)(C)C)c1cc([N+](=O)[O-])ccc1F]

Starting from 2'-fluoro-5'-nitroacetophenone, the product (R)-2-methyl-propane-2-sulfinic acid [1-(2-fluoro-5-nitro-phenyl)-(E)-ethylidene]-amide was obtained as a pale red oil. MS (ISP): m/z=287.2 [M+H]+.

Intermediate A2D

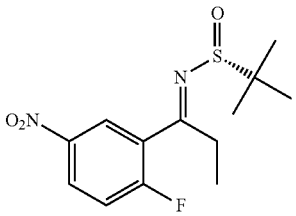 [SMILES: CC/C(=N\[S@](=O)C(C)(C)C)c1cc([N+](=O)[O-])ccc1F]

Starting from 1-(2-fluoro-5-nitro-phenyl)-propan-1-one, the product (R)-2-methyl-propane-2-sulfinic acid [1-(2-fluoro-5-nitro-phenyl)-prop-(E)-ylidene]-amide was obtained as pale red oil. MS (ISP): m/z=301.3 [M+H]+.

Intermediate A2E

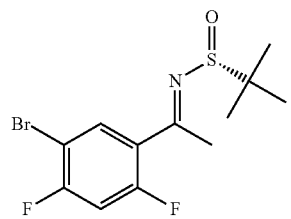 [SMILES: C/C(=N\[S@](=O)C(C)(C)C)c1cc(Br)c(F)cc1F]

Starting from commercially available 1-(5-bromo-2,4-difluorophenyl)-ethanone [CAS No. 864773-64-8] the product (R)-2-methyl-propane-2-sulfinic acid [1-(5-bromo-2,4-difluoro-phenyl)-eth-(E)-ylidene]-amide was obtained as a pale red oil. MS (ISP): m/z=338.1 [M+H]⁺ and 340.1 [M+2H]⁺.

Intermediate A2F

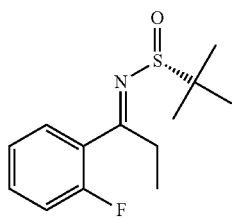 [SMILES: CC/C(=N\[S@](=O)C(C)(C)C)c1ccccc1F]

Starting from commercially available 2'-fluoropropiophenone [CAS No. 21120-36-5] the product (R)-2-methyl-propane-2-sulfinic acid [1-(2-fluoro-phenyl)-prop-(E)-ylidene]-amide was obtained as a yellow oil. MS (ISP): m/z=256.2 [M+H]⁺.

Synthesis of the Intermediate Sulfinamide Esters A3

General Procedure (Via Reformatsky Reaction)

In a dry apparatus a suspension of freshly activated zinc powder (1.63 g, 24.9 mmol) in dry THF (70 ml) was heated under inert atmosphere to reflux. A solution of the sulfinyl imine A2 (24.9 mmol) and the bromo-acetate (24.9 mmol) in dry THF (15 ml) was added dropwise over a period of 15 min and the suspension was heated to reflux for 5 h. The cooled mixture was partitioned between aqueous saturated NH₄Cl and ethyl acetate, the organic layer was dried and evaporated. The crude material was purified by flash chromatography using heptane/ethyl acetate to give the sulfinamide ester A3.

Intermediates A3A and A3B

A3A

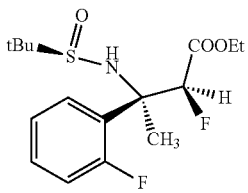

A3B

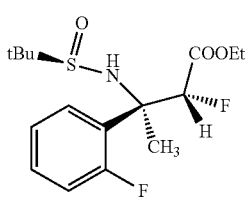

Starting from (R)-2-methyl-propane-2-sulfinic acid [1-(2-fluorophenyl)-(E)-ethylidene]-amide and ethyl 2-bromo-2-fluoroacetate, the faster eluting minor isomer (2S,3R)-ethyl 3-((R)-1,1-dimethylethylsulfinamido)-2-fluoro-3-(2-fluorophenyl)butanoate (intermediate A3A) was obtained as a dark brown oil. MS (ISP): m/z=348.2 [M+H]⁺.

The second fraction contained the slower eluting major isomer (2R,3R)-ethyl 3-((R)-1,1-dimethylethylsulfinamido)-2-fluoro-3-(2-fluorophenyl)butanoate (intermediate A3B) as a brown oil. MS (ISP): m/z=348.2 [M+H]⁺.

Intermediate A3C

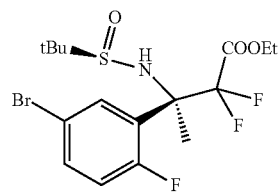 [SMILES: CCOC(=O)C(F)(F)[C@](C)(N[S@](=O)C(C)(C)C)c1cc(Br)ccc1F]

Starting from (R)-2-methyl-propane-2-sulfinic acid [1-(2-fluoro-5-bromo-phenyl)-(E)-ethylidene]-amide and ethyl 2-bromo-2,2-difluoroacetate, the product (3R)-ethyl 3-((R)-1,1-dimethyl ethyl sulfinamido)-2,2-difluoro-3-(2-fluoro-5-bromo-phenyl)butanoate was obtained as an orange oil. MS (ISP): m/z=446.1 [M+H]⁺.

Intermediate A3D

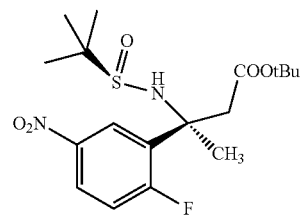

Starting from (R)-2-methyl-propane-2-sulfinic acid [1-(2-fluoro-5-nitro-phenyl)-eth-(E)-ylidene]-amide, the product (S)-3-(2-fluoro-5-nitro-phenyl)-(R)-3-(2-methyl-propane-2-sulfinylamino)-butyric acid tert-butyl ester was obtained as an orange oil. MS (ISP): m/z=403.0 [M+H]⁺.

Intermediate A3E

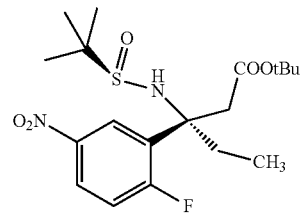

Starting from (R)-2-methyl-propane-2-sulfinic acid [1-(2-fluoro-5-nitro-phenyl)-prop-(E)-ylidene]-amide, the product (S)-3-(2-fluoro-5-nitro-phenyl)-(R)-3-(2-methyl-propane-2-sulfinylamino)-pentanoic acid tert-butyl ester was obtained as an orange oil. MS (ISP): m/z=417.5 [M+H]⁺.

Intermediate A3F (S)-3-(5-bromo-2-fluoro-phenyl)-3-((R)-2-methyl-propane-2-sulfinylamino)-butyric acid ethyl ester

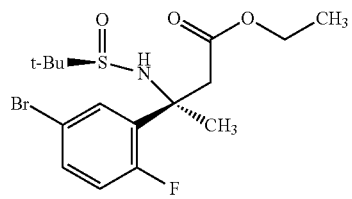 [SMILES: CCOC(=O)C[C@](C)(N[S@](=O)C(C)(C)C)c1cc(Br)ccc1F]

A dried four-necked 750 ml round-bottom flask equipped with mechanical stirrer, reflux condenser, internal thermometer and septum was charged with activated zinc powder (30.6 g, 468 mmol) and copper(I) chloride (4.64 g, 47 mmol), the two solids were mixed under a slow stream of nitrogen while the flask was dried with a heat gun. After cooling to 23° C., dry THF (90 ml) was added to produce a dark slurry, heated to reflux and stirred vigorously for 30 min. The heating bath was removed and a solution of ethyl bromoacetate (12.95 ml, 117 mmol) in dry THF (50 ml) was added at such rate that reflux was reinitiated and a controllable reflux was maintained. Once addition was complete, the mixture was stirred for 30 min at 50° C. Cooled to 5° C., a solution of (R)-2-methyl-propane-2-sulfinic acid [1-(2-fluoro-5-bromo-phenyl)-(E)-ethylidene]-amide (intermediate A2B) (15.0 g, 47 mmol) in dry THF (60 ml) was added dropwise and the mixture was stirred at 0° C. for 1 h. The reaction mixture was filtered through dicalite, washed with TBME, the filtrate was washed with 5% citric acid, sat. NaHCO$_3$-sol. and brine, dried over Na$_2$SO$_4$. Removal of the solvent in vacuum left the crude title compound as an orange oil (20.3 g, 106%), which was used in the next step without further purification. MS (ISP): m/z=408.0 [(M+H)$^+$] and 410.1 [(M+2+H)$^+$].

Intermediate A3G

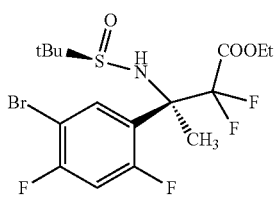 [SMILES: CCOC(=O)C(F)(F)[C@](C)(N[S@](=O)C(C)(C)C)c1cc(Br)c(F)cc1F]

Starting from (R)-2-methyl-propane-2-sulfinic acid [1-(5-bromo-2,4-difluoro-phenyl)-eth-(E)-ylidene]-amide (intermediate A2E) and ethyl 2-bromo-2,2-difluoroacetate, the product (R)-3-(5-bromo-2,4-difluoro-phenyl)-2,2-difluoro-3-((R)-2-methyl-propane-2-sulfinylamino)-butyric acid ethyl ester was obtained as an orange oil. MS (ISP): m/z=462.1 [M+H]$^+$ and 464.1 [M+2+H]$^+$.

Intermediate A3H

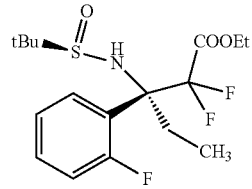 [SMILES: CCOC(=O)C(F)(F)[C@](CC)(N[S@](=O)C(C)(C)C)c1ccccc1F]

Starting from (R)-2-methyl-propane-2-sulfinic acid [1-(2-fluoro-phenyl)-prop-(E)-ylidene]-amide (intermediate A2F) and ethyl 2-bromo-2,2-difluoroacetate, the product (R)-2,2-difluoro-3-(2-fluoro-phenyl)-3-((R)-2-methyl-propane-2-sulfinylamino)-pentanoic acid ethyl ester was obtained as a colorless oil. MS (ISP): m/z=380.2 [M+H]$^+$.

General Procedure (Via Titanium Enolate Reaction)

To a solution of diisopropylamine (21.9 ml) in THF (250 ml) was added at −78° C. n-butyllithium (1.6 M solution in hexane, 97.2 ml) and stirring was continued at −78° C. for 30 min. The solution was treated with methyl acetate (12.4 ml) and after 30 min a solution of chlorotriisopropoxytitanium (43.0 g) in THF (50 ml) was added and stirring was continued at −78° C. for 30 min. The mixture was treated with a solution of the sulfinyl imine A2 (47.1 mmol) in THF (25 ml) and stirring was continued at −78° C. for 3 h. The mixture was quenched with saturated aqueous NH$_4$Cl solution (300 ml) and the mixture was filtered over dicalite. The layers were separated, the aqueous layer was extracted with ethyl acetate, the combined organic layers were washed with water, dried and evaporated. The residue was purified by chromatography on silica using cylohexane/ethyl acetate (1:2) to give the pure sulfinamide ester A3.

Synthesis of the Intermediate Sulfinamide Alcohols A4

General Procedure

A solution of the sulfinamide ester A3 (12.7 mmol) in dry THF (50 ml) was treated at 0° C. with lithium borohydride (25.3 mmol) and stirring was continued at 0° C. for 4 h. The reaction mixture was quenched by addition of acetic acid (2 ml) and water (50 ml), extracted with ethyl acetate and the organic layer was dried and evaporated. The residue was purified by chromatography on silica using a mixture of n-heptane and ethyl acetate to give the pure intermediate sulfinamide alcohol A4.

Intermediate A4A

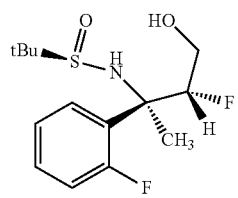 [SMILES: CC(C)(C)[S@@](=O)N[C@](C)(c1ccccc1F)[C@@H](F)CO]

Starting from (2R,3R)-ethyl 3-((R)-1,1-dimethylethylsulfinamido)-2-fluoro-3-(2-fluorophenyl)butanoate, the product (R)-2-methyl-propane-2-sulfinic acid [(1R,2R)-2-fluoro-1-(2-fluoro-phenyl)-3-hydroxy-1-methyl-propyl]-amide was obtained as pale red crystals. MS (ISP): m/z=306.1 [M+H]$^+$.

Intermediate A4B

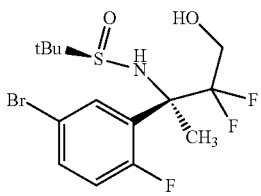 [SMILES: CC(C)(C)[S@@](=O)N[C@](C)(c1cc(Br)ccc1F)C(F)(F)CO]

Starting from (3R)-ethyl 3-((R)-1,1-dimethylethylsulfinamido)-2,2-difluoro-3-(2-fluoro-5-bromo-phenyl)butanoate, the product (S)—N—((R)-2-(5-bromo-2-fluorophenyl)-3,3-difluoro-4-hydroxybutan-2-yl)-2-methylpropane-2-sulfinamide was obtained as a colorless solid. MS (ISP): m/z=402.2 [M+H]$^+$.

Intermediate A4C

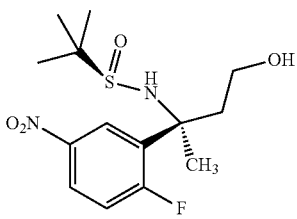 [SMILES: CC(C)(C)[S@@](=O)N[C@@](C)(CCO)c1cc([N+](=O)[O-])ccc1F]

Starting from (S)-3-(2-fluoro-5-nitro-phenyl)-(R)-3-(2-methyl-propane-2-sulfinylamino)-butyric acid tert-butyl ester, the product (R)-2-methyl-propane-2-sulfinic acid [(S)-1-(2-fluoro-5-nitro-phenyl)-3-hydroxy-1-methyl-propyl]-amide was obtained as an orange oil. MS (ISP): m/z=333.0 [M+H]$^+$.

Intermediate A4D

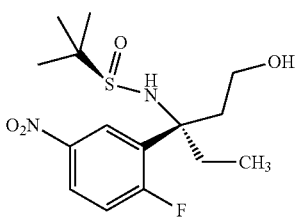 [SMILES: CC[C@@](CCO)(N[S@](=O)C(C)(C)C)c1cc([N+](=O)[O-])ccc1F]

Starting from (S)-3-(2-fluoro-5-nitro-phenyl)-(R)-3-(2-methyl-propane-2-sulfinylamino)-pentanoic acid tert-butyl ester, the product (R)-2-methyl-propane-2-sulfinic acid [(S)-1-ethyl-1-(2-fluoro-5-nitro-phenyl)-3-hydroxy-propyl]-amide was obtained as an orange oil. MS (ISP): m/z=347.0 [M+H]$^+$.

Intermediate A4E (R)-2-Methyl-propane-2-sulfinic acid [(S)-1-(5-bromo-2-fluoro-phenyl)-3-hydroxy-1,3-dimethyl-butyl]-amide

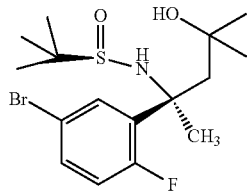 [SMILES: CC(C)(O)C[C@](C)(N[S@](=O)C(C)(C)C)c1cc(Br)ccc1F]

To a solution of (S)-3-(5-bromo-2-fluoro-phenyl)-3-(R)-2-methyl-propane-2-sulfinylamino)-butyric acid ethyl ester (intermediate A3F) (10.0 g, 24 mmol) in anhydrous THF (300 ml) at −70° C. was dropwise added a methyl magnesium bromide solution (3.2 M in THF; 61.2 ml, 196 mmol) within 30 min. The yellow solution was stirred for 1 h at −70° C. and then for 16 h at 23° C. The yellow solution was quenched with 200 ml ice cold sat. NH$_4$Cl solution and extracted with ethyl acetate. The organic layer was washed with water and brine, dried over Na$_2$SO$_4$, filtered and evaporated to give the title compound as a yellow oil (10.8 g, 95%; ca. 85% purity), which was used in the next step without further purification. MS (ISP): m/z=394.1 [(M+H)$^+$] and 396.1 [(M+2+H)$^+$].

Intermediate A4F (R)—N—((R)-2-(5-bromo-2-fluorophenyl)-3,3-difluoro-4-hydroxy-4-methylpentan-2-yl)-2-methylpropane-2-sulfinamide

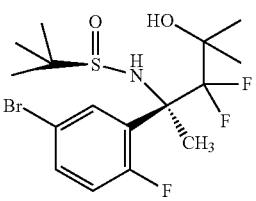 [SMILES: CC(C)(C)[S@@](=O)N[C@](C)(c1cc(Br)ccc1F)C(F)(F)C(C)(C)O]

To a solution of (R)-ethyl 3-(5-bromo-2-fluorophenyl)-3-(R)-1,1-dimethylethylsulfinamido)-2,2-difluorobutanoate (intermediate A3C) (10.5 g, 23.6 mmol) in anhydrous THF (150 ml) at −78° C. was dropwise added a methylmagnesium bromide solution (3.2 M in 2-methyl-THF; 59.1 ml, 189 mmol), the cooling bath was removed and the mixture was stirred at 23° C. for 18 h. Poured cautiously into sat. NH$_4$Cl-sol., extracted with ethyl acetate, washed organic layer with brine and dried over Na$_2$SO$_4$. Removal of the solvent in vacuum left the (R)—N—((R)-2-(5-bromo-2-fluorophenyl)-3,3-difluoro-4-hydroxy-4-methylpentan-2-yl)-2-methylpropane-2-sulfinamide (10.565 g, 23.6 mmol, 99.7% yield) as a yellow gum, which was used in the next step without further purification. MS (ISP): m/z=430.1 [(M+H)$^+$] and 432.1 [(M+2+H)$^+$].

Intermediate A4G (R)—N—((R)-2-(5-bromo-2,4-difluorophenyl)-3,3-difluoro-4-hydroxy-4-methylpentan-2-yl)-2-methyl-propane-2-sulfinamide

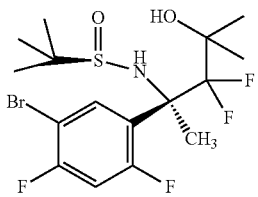 [SMILES: CC(C)(C)[S@@](=O)N[C@](C)(c1cc(Br)c(F)cc1F)C(F)(F)C(C)(C)O]

To a solution of (R)-ethyl 3-(5-bromo-2,4-difluorophenyl)-3-(R)-1,1-dimethylethylsulfinamido)-2,2-difluorobutanoate (intermediate A3G) (23.1 g, 50.0 mmol) in anhydrous THF (700 ml) at −78° C. was dropwise added a methylmagnesium bromide solution (3.2 M in 2-methyl-THF; 125 ml, 400 mmol), the cooling bath was removed and the mixture was stirred at 23° C. for 18 h. Poured cautiously into sat. NH$_4$Cl-sol., extracted with ethyl acetate, washed organic layer with brine and dried over Na$_2$SO$_4$. Removal of the solvent in vacuum left the (R)—N—((R)-2-(5-bromo-2,4-difluorophenyl)-3,3-difluoro-4-hydroxy-4-methylpentan-2-yl)-2-methylpropane-2-sulfinamide (21.4 g, 47.7 mmol, 95.5% yield) as a light yellow solid, which was used in the next step without further purification. MS (ISP): m/z=448.1 [(M+H)$^+$] and 450.1 [(M+2+H)$^+$].

Intermediate A4H

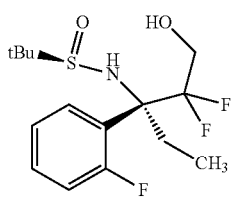 [SMILES: CC[C@@](N[S@](=O)C(C)(C)C)(c1ccccc1F)C(F)(F)CO]

Starting from (R)-2,2-difluoro-3-(2-fluoro-phenyl)-3-(R)-2-methyl-propane-2-sulfinylamino)-pentanoic acid ethyl ester (intermediate A3H), the product 2-methyl-propane-2-sulfinic acid [(R)-1-ethyl-2,2-difluoro-1-(2-fluoro-phenyl)-3-hydroxy-propyl]-amide was obtained as a white solid. MS (ISP): m/z=338.1 [M+H]$^+$.

Synthesis of the Intermediate Sulfinamide Nitrile A5 (R$^1$=R$^2$=H)

General procedure

To a solution of the sulfinamide alcohol A4 (4.1 mmol) in dichloromethane (23 ml) was subsequently added at 22° C. 2-bromoacetonitrile (6.2 mmol), silver(I) oxide (1.9 g) and tetrabutylammonium iodide (0.30 g) and stirring was continued for 2 h. The suspension was filtered, the filtrate was washed with aqueous saturated NaHCO$_3$ solution, the organic layer was dried and evaporated to give the crude sulfinamide nitrile A5 which was used without further purification.

Intermediate A5A

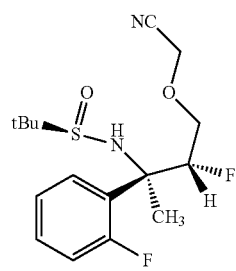 [SMILES: CC(C)(C)[S@@](=O)N[C@](C)(c1ccccc1F)[C@@H](F)COCC#N]

Starting from (R)-2-methyl-propane-2-sulfinic acid [(1R,2R)-2-fluoro-1-(2-fluoro-phenyl)-3-hydroxy-1-methyl-propyl]-amide, the product (R)—N-((2R,3R)-4-(cyanomethoxy)-3-fluoro-2-(2-fluorophenyl)butan-2-yl)-2-methylpropane-2-sulfinamide was obtained as a pale yellow oil. MS (ISP): m/z=345.2 [M+H]$^+$.

Intermediate A5B

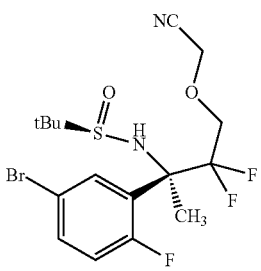 [SMILES: CC(C)(C)[S@@](=O)N[C@](C)(c1cc(Br)ccc1F)C(F)(F)COCC#N]

Starting from (S)—N—((R)-2-(5-bromo-2-fluorophenyl)-3,3-difluoro-4-hydroxybutan-2-yl)-2-methylpropane-2-sulfinamide, the product (S)—N—((R)-2-(5-bromo-2-fluorophenyl)-4-(cyanomethoxy)-3,3-difluorobutan-2-yl)-2-methylpropane-2-sulfinamide was obtained as a colorless oil. MS (ISP): m/z=441.1 [M+H]$^+$.

Intermediate A5C

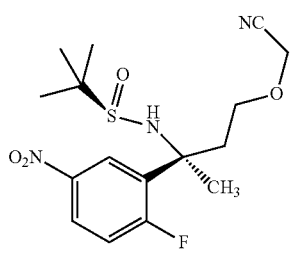 [SMILES: CC(C)(C)[S@@](=O)N[C@@](C)(CCOCC#N)c1cc([N+](=O)[O-])ccc1F]

Starting from (R)-2-methyl-propane-2-sulfinic acid [(S)-1-(2-fluoro-5-nitro-phenyl)-3-hydroxy-1-methyl-propyl]-amide, the product (R)-2-methyl-propane-2-sulfinic acid [(S)-3-cyanomethoxy-1-(2-fluoro-5-nitro-phenyl)-1-methyl-propyl]-amide was obtained as an orange oil. MS (ISP): m/z=372.0 [M+H]$^+$.

Intermediate A5D

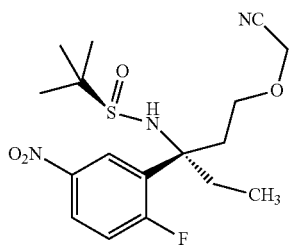 [SMILES: CC[C@@](CCOCC#N)(N[S@](=O)C(C)(C)C)c1cc([N+](=O)[O-])ccc1F]

Starting from (R)-2-methyl-propane-2-sulfinic acid [(S)-1-ethyl-1-(2-fluoro-5-nitro-phenyl)-3-hydroxy-propyl]-amide, the product (R)-2-methyl-propane-2-sulfinic acid [(S)-3-cyanomethoxy-1-ethyl-1-(2-fluoro-5-nitro-phenyl)-propyl]-amide was obtained as an orange oil. MS (ISP): m/z=386.1 [M+H]$^+$.

Intermediate A5E

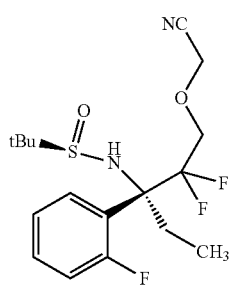 [SMILES: CC[C@@](N[S@](=O)C(C)(C)C)(c1ccccc1F)C(F)(F)COCC#N]

Starting from 2-methyl-propane-2-sulfinic acid [(R)-1-ethyl-2,2-difluoro-1-(2-fluoro-phenyl)-3-hydroxy-propyl]-amide (intermediate A4H), the product 2-methyl-propane-2-sulfinic acid [(R)-3-cyanomethoxy-1-ethyl-2,2-difluoro-1-(2-fluoro-phenyl)-propyl]-amide was obtained as a light yellow oil. MS (ISP): m/z=377.3 [M+H]$^+$.

Synthesis of the Intermediate Sulfinamide Nitrile A5
($R^1=R^2=Me$)

To a solution of acetone cyanohydrin (307 mg, 3.6 mmol) in 10 ml DCE was added to a solution of SnCl$_4$ 1.0 M in DCM (3.91 ml, 3.9 mmol) at RT, then addition of the alcohol (1 g, 3 mmol). The reaction mixture was stirred at RT for 10 min, then stirred at 60° C. for two days, controlled by TLC (EE pure). Reaction mixture cooled down to RT and poured into a mixture of DCM and aq. Na$_2$CO$_3$, solution stirred for 20 min. A white precipitate formed and was filtered over Celite®, separation of the two phases in the filtrate, organic phase dried over Na$_2$SO$_4$, filtered and evaporated down to dryness. The residue was purified by chromatography on silica with a mixture of heptane and ethyl acetate to give yellow oil.

Intermediate A5F

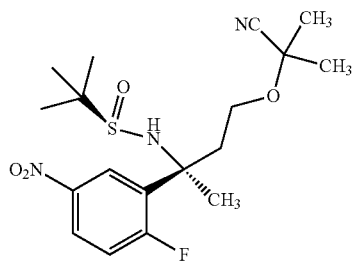 [SMILES: CC(C)(C#N)OCC[C@](C)(N[S@](=O)C(C)(C)C)c1cc([N+](=O)[O-])ccc1F]

Starting from (R)-2-methyl-propane-2-sulfinic acid [(S)-1-(2-fluoro-5-nitro-phenyl)-3-hydroxy-1-methyl-propyl]-amide, the product (R)-2-methyl-propane-2-sulfinic acid [(S)-3-(cyano-dimethyl-methoxy)-1-(2-fluoro-5-nitro-phenyl)-1-methyl-propyl]-amide was obtained as an orange oil. MS (ISP): m/z=400.1 [M+H]$^+$.

Synthesis of the Intermediate Amino Nitrile A6

General Procedure

A solution of the sulfinamide nitrile A5 (4.25 mmol) in 1,4-dioxane (20 ml) was treated with a solution of HCl in 1,4-dioxane (4 M, 5.3 ml) and stirring was continued at 22° C. for 1 h. The mixture was diluted with ethyl acetate, washed with saturated aqueous Na$_2$CO$_3$ solution, the organic layer was dried and evaporated. The crude material was purified on silica using n-heptane/ethyl acetate to give the pure amino nitrile A6.

Intermediate A6A

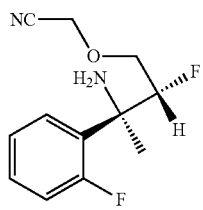 [SMILES: C[C@@](N)(c1ccccc1F)[C@@H](F)COCC#N]

Starting from (R)—N-((2R,3R)-4-(cyanomethoxy)-3-fluoro-2-(2-fluorophenyl)butan-2-yl)-2-methylpropane-2-sulfinamide, the product 2-((2R,3R)-3-amino-2-fluoro-3-(2-fluorophenyl)butoxy)acetonitrile was obtained as a pale yellow oil. MS (ISP): m/z=241.1 [M+H]$^+$.

Intermediate A6B

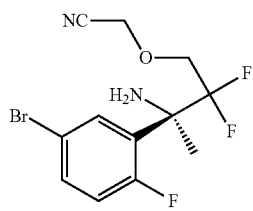 [SMILES: C[C@@](N)(c1cc(Br)ccc1F)C(F)(F)COCC#N]

Starting from (S)—N—((R)-2-(5-bromo-2-fluorophenyl)-4-(cyanomethoxy)-3,3-difluorobutan-2-yl)-2-methylpropane-2-sulfinamide, the product (R)-2-(3-amino-3-(5-bromo-2-fluorophenyl)-2,2-difluorobutoxy)acetonitrile was obtained as a colorless oil. MS (ISP): m/z=337.2 [M+H]⁺.

Intermediate A6C

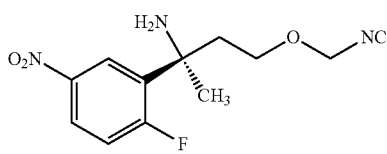

Starting from (R)-2-methyl-propane-2-sulfinic acid [(S)-3-cyanomethoxy-1-(2-fluoro-5-nitro-phenyl)-1-methyl-propyl]-amide, the product [(S)-3-amino-3-(2-fluoro-5-nitrophenyl)-butoxy]-acetonitrile was obtained as an orange oil. MS (ISP): m/z=268.0 [M+H]⁺.

Intermediate A6D

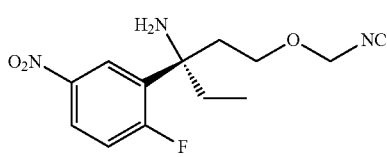

Starting from (R)-2-methyl-propane-2-sulfinic acid [(S)-3-cyanomethoxy-1-ethyl-1-(2-fluoro-5-nitro-phenyl)-propyl]-amide, the product [(S)-3-amino-3-(2-fluoro-5-nitrophenyl)-pentyloxy]-acetonitrile was obtained as an orange oil. MS (ISP): m/z=282.4 [M+H]⁺.

Intermediate A6E

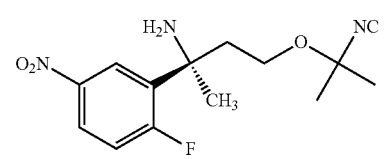

Starting from (R)-2-methyl-propane-2-sulfinic acid [(S)-3-(cyano-dimethyl-methoxy)-1-(2-fluoro-5-nitro-phenyl)-1-methyl-propyl]-amide, the product 2-[(S)-3-amino-3-(2-fluoro-5-nitro-phenyl)-butoxy]-2-methyl-propionitrile was obtained as an orange oil. MS (ISP): m/z=296.3 [M+H]⁺.

Intermediate A6F

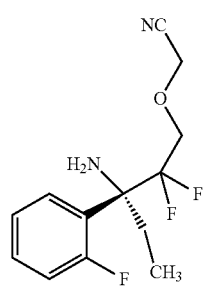 [SMILES: CC[C@@](N)(c1ccccc1F)C(F)(F)COCC#N]

Starting from 2-methyl-propane-2-sulfinic acid [(R)-3-cyanomethoxy-1-ethyl-2,2-difluoro-1-(2-fluoro-phenyl)-propyl]-amide (intermediate A5E), the product [(R)-3-amino-2,2-difluoro-3-(2-fluoro-phenyl)-pentyloxy]-acetonitrile was obtained as a colorless oil. MS (ISP): m/z=273.1 [M+H]⁺.

Synthesis of the Intermediate 1,4-oxazepine A7

General Procedure

To a solution of the amino nitrile A6 (2.20 mmol) in toluene (38 ml) was added at 22° C. a solution of AlMe₃ in toluene (2 M, 1.2 ml) and the mixture was heated to 80° C. for 1 h. The mixture was cooled to 0° C., diluted with saturated aqueous Na₂CO₃ and the aqueous layer was extracted with ethyl acetate. The combined organic layers were dried, evaporated and the residue purified by chromatography on NH₂-silica using n-heptane/ethyl acetate to give the pure 1,4-oxazepine A7.

Intermediate A7A

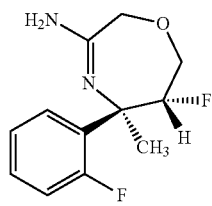 [SMILES: C[C@]1(c2ccccc2F)N=C(N)COC[C@@H]1F]

Starting from 2-((2R,3R)-3-amino-2-fluoro-3-(2-fluorophenyl)butoxy)acetonitrile, the product (5R,6R)-6-fluoro-5-(2-fluorophenyl)-5-methyl-2,5,6,7-tetrahydro-1,4-oxazepin-3-amine was obtained as a pale yellow solid. MS (ISP): m/z=241.2 [M+H]⁺.

Intermediate A7B

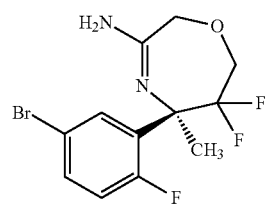 [SMILES: C[C@]1(c2cc(Br)ccc2F)N=C(N)COCC1(F)F]

Starting from (R)-2-(3-amino-3-(5-bromo-2-fluorophenyl)-2,2-difluorobutoxy)acetonitrile, the product (R)-5-(5-bromo-2-fluorophenyl)-6,6-difluoro-5-methyl-2,5,6,7-tetrahydro-1,4-oxazepin-3-amine was obtained as a colorless oil. MS (ISP): m/z=337.2 [M+H]⁺ and 339.2 [M+2+H]⁺.

Intermediate A7C

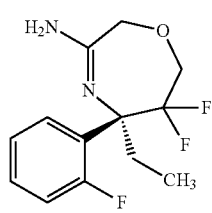 [SMILES: CC[C@]1(c2ccccc2F)N=C(N)COCC1(F)F]

Starting from [(R)-3-amino-2,2-difluoro-3-(2-fluoro-phenyl)-pentyloxy]-acetonitrile (intermediate A6F), the product (R)-5-ethyl-6,6-difluoro-5-(2-fluoro-phenyl)-2,5,6,7-tetrahydro-[1,4]oxazepin-3-ylamine was obtained as a dark brown oil. MS (ISP): m/z=273.1 [M+H]+.

Intermediate A7D

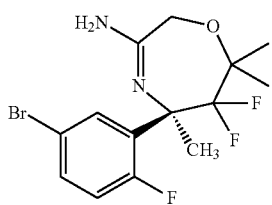 [SMILES: CC1(C)OCC(N)=N[C@](C)(c2cc(Br)ccc2F)C1(F)F]

a) Starting from (R)-5-(5-bromo-2-fluorophenyl)-6,6-difluoro-5,7,7-trimethyl-[1,4]oxazepan-3-one (intermediate A16B) (1 g, 2.73 mmol) the lactam was converted into the thiolactam as described for intermediate A20A. Obtained the (R)-5-(5-bromo-2-fluorophenyl)-6,6-difluoro-5,7,7-trimethyl-1,4-oxazepane-3-thione (0.92 g, 2.41 mmol, 88.1% yield) as a light yellow oil. MS (ISN): m/z=379.9 [M−H]− and 381.8 [M+2−H]−.

b) The (R)-5-(5-bromo-2-fluorophenyl)-6,6-difluoro-5,7,7-trimethyl-1,4-oxazepane-3-thione (0.92 g, 2.41 mmol) was converted into the amidine following a procedure as described for example 8. The product (R)-5-(5-bromo-2-fluorophenyl)-6,6-difluoro-5,7,7-trimethyl-2,5,6,7-tetrahydro-1,4-oxazepin-3-amine (0.425 g, 1.16 mmol, 48.4%) was obtained as a white foam. MS (ISP): m/z=365.2 [M+H]+ and 367.1 [M+2+H]+.

Synthesis of the Intermediate DMT-1,4-oxazepine A8A

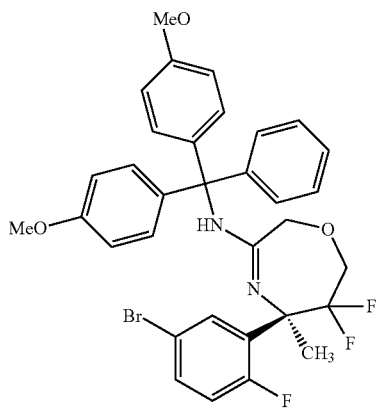 [SMILES: COc1ccc(C(NC2=N[C@](C)(c3cc(Br)ccc3F)C(F)(F)COC2)(c2ccccc2)c2ccc(OC)cc2)cc1]

To a solution of (R)-5-(5-bromo-2-fluorophenyl)-6,6-difluoro-5-methyl-2,5,6,7-tetrahydro-1,4-oxazepin-3-amine (9.0 mmol) in dichloromethane (150 ml) was subsequently added at 0° C. NEt3 (18.0 mmol) and 4,4'-dimethoxytriphenylmethyl chloride (9.9 mmol) and stirring was continued at 22° C. for 2 h. The mixture was washed with saturated aqueous NH4Cl, the organic layer was dried, evaporated and the residue was purified by chromatography on silica using cyclohexane/ethyl acetate to give pure (R)—N-(bis(4-methoxyphenyl)(phenyl)methyl)-5-(5-bromo-2-fluorophenyl)-6,6-difluoro-5-methyl-2,5,6,7-tetrahydro-1,4-oxazepin-3-amine (A8A) as a colorless foam. MS (ISP): m/z=639.3 [M+H]+ and 641.4 [M+2+H]+.

Intermediate A8B

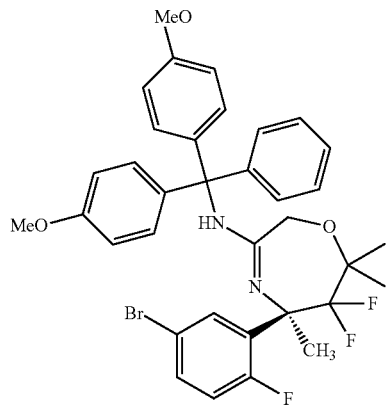 [SMILES: COc1ccc(C(NC2=N[C@](C)(c3cc(Br)ccc3F)C(F)(F)C(C)(C)OC2)(c2ccccc2)c2ccc(OC)cc2)cc1]

Prepared in an analogous manner as described for intermediate A8A from (R)-5-(5-bromo-2-fluorophenyl)-6,6-difluoro-5,7,7-trimethyl-2,5,6,7-tetrahydro-1,4-oxazepin-3-amine (intermediate A7D) (302.6 mg, 829 μmol). Obtained the (R)—N-(bis(4-methoxyphenyl)(phenyl)methyl)-5-(5-bromo-2-fluorophenyl)-6,6-difluoro-5,7,7-trimethyl-2,5,6,7-tetrahydro-1,4-oxazepin-3-amine (418 mg, 74%) as a white foam. MS (ISP): m/z=667.2 [M+H]+ and 669.3 [M+2+H]+.

Synthesis of the Intermediate Imine A9A

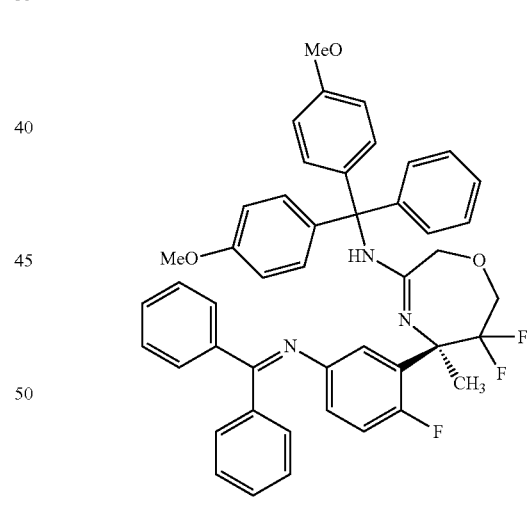

To a solution of (R)—N-(bis(4-methoxyphenyl)(phenyl)methyl)-5-(5-bromo-2-fluorophenyl)-6,6-difluoro-5-methyl-2,5,6,7-tetrahydro-1,4-oxazepin-3-amine (intermediate A8A) (1.2 mmol) in toluene (15 ml) was added subsequently at 22° C. and under a argon atmosphere benzophenone imine (2.4 mmol), sodium tert-butoxide (3.6 mmol) and 2-di-t-butylphosphino-2',4',6'-triisopropylbiphenyl (0.12 mmol). To the mixture was added tris(dibenzylideneacetone) dipalladium chloroform adduct (0.036 mmol), the tube was sealed and heated to 105° C. for 3 h. The mixture was cooled to 22° C., partitioned between saturated aqueous NaHCO3 and ethyl acetate, the organic layer was dried and evaporated to give the crude (R)—N-(bis(4-methoxyphenyl)(phenyl)methyl)-5-(5-(diphenylmethyleneamino)-2-fluorophenyl)-6,6-difluoro-5-methyl-2,5,6,7-tetrahydro-1,4-oxazepin-3-amine (A9A) as a yellow oil. MS (ISN): m/z=738.5 [M−H]⁻.

Synthesis of the Intermediate Aniline A10A from the Imine A9A

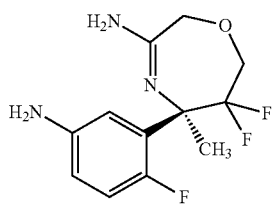 [SMILES: C[C@]1(c2cc(N)ccc2F)N=C(N)COCC1(F)F]

To a solution of crude (R)—N-(bis(4-methoxyphenyl)(phenyl)methyl)-5-(5-(diphenylmethyleneamino)-2-fluorophenyl)-6,6-difluoro-5-methyl-2,5,6,7-tetrahydro-1,4-oxazepin-3-amine (1.2 mmol) in dichloromethane (20 ml) was added at 22° C. trifluoroacetic acid (2.6 ml) and stirring was continued for 1 h. The mixture was diluted with 1,4-dioxane (40 ml) and aqueous hydrochloric acid (1 M, 33 ml) and vigorous stirring of the emulsion at 22° C. was continued for 16 h. The mixture was evaporated and the residue partitioned between saturated aqueous NaCl and ethyl acetate, the aqueous layer was separated, the pH was adjusted to 14 using saturated aqueous $Na_2CO_3$ solution and extracted with ethyl acetate. The organic layer was dried, evaporated and the residue purified by chromatography on silica-$NH_2$ using dichloromethane to give (R)-5-(5-amino-2-fluorophenyl)-6,6-difluoro-5-methyl-2,5,6,7-tetrahydro-1,4-oxazepin-3-amine as a colorless oil. MS (ISP): m/z=274.3 [M+H]⁺.

General Procedure for Synthesis of Nitrobenzenes A11 Directly from Nitriles A6

To a solution of the amino nitrile A6 (2.20 mmol) in toluene (38 ml) was added at 22° C. a solution of $AlMe_3$ in toluene (2 M, 1.2 ml) and the mixture was heated to 80° C. for 1 h. The mixture was cooled to 0° C., diluted with saturated aqueous $Na_2CO_3$ and the aqueous layer was extracted with ethyl acetate. The combined organic layers were dried, evaporated and the residue purified by chromatography on $NH_2$-silica using n-heptane/ethyl acetate to give the pure 1,4-oxazepine A11.

Intermediate A11A

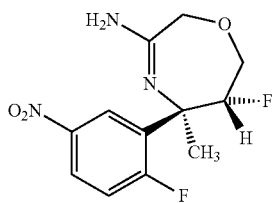

To a solution of (5R,6R)-6-fluoro-5-(2-fluorophenyl)-5-methyl-2,5,6,7-tetrahydro-1,4-oxazepin-3-amine (1.2 mmol) in sulfuric acid (5.0 ml) was added at 0° C. red fuming nitric acid (1.9 mmol) over a period of 20 min and stirring was continued for 30 min. The solution was dropped slowly into ice/water (60 ml), the pH was adjusted to 9 by addition of aqueous 4 N NaOH and extracted with ethyl acetate. The organic layer was dried, evaporated and the residue purified by chromatography on silica-$NH_2$ using n-heptane/ethyl acetate to give (5R,6R)-6-fluoro-5-(2-fluoro-5-nitro-phenyl)-5-methyl-2,5,6,7-tetrahydro-1,4-oxazepin-3-ylamine as a pale yellow solid. MS (ISP): m/z=286.2 [M+H]⁺.

Intermediate A11B

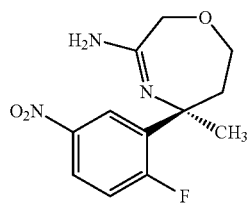

Starting from [(S)-3-amino-3-(2-fluoro-5-nitro-phenyl)-butoxy]-acetonitrile, the product (S)-5-(2-fluoro-5-nitro-phenyl)-5-methyl-2,5,6,7-tetrahydro-1,4-oxazepin-3-ylamine was obtained as an orange oil. MS (ISP): m/z=268.3 [M+H]⁺.

Intermediate A11C

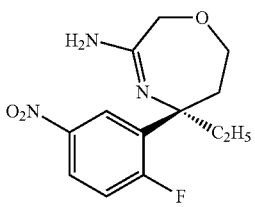

Starting from [(S)-3-amino-3-(2-fluoro-5-nitro-phenyl)-pentyloxy]-acetonitrile, the product (S)-5-ethyl-5-(2-fluoro-5-nitro-phenyl)-2,5,6,7-tetrahydro-1,4-oxazepin-3-ylamine was obtained as an orange oil. MS (ISP): m/z=282.3 [M+H]⁺.

Intermediate A11E

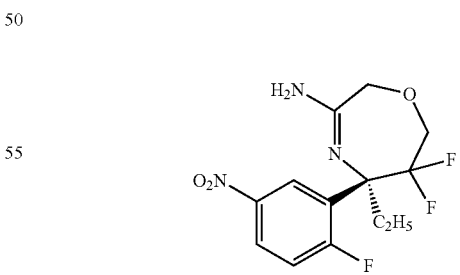

Starting from (R)-5-ethyl-6,6-difluoro-5-(2-fluoro-phenyl)-2,5,6,7-tetrahydro-[1,4]oxazepin-3-ylamine (intermediate A7C), the product (R)-5-ethyl-6,6-difluoro-5-(2-fluoro-5-nitro-phenyl)-2,5,6,7-tetrahydro-[1,4]oxazepin-3-ylamine was obtained as a light yellow oil. MS (ISP): m/z=318.1 [M+H]⁺.

Synthesis of the Intermediate Aniline A10B Via Reduction of the Nitrobenzene A11A

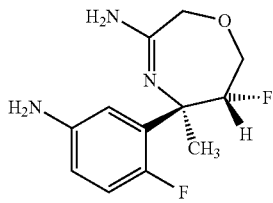

A suspension of (5R,6R)-6-fluoro-5-(2-fluoro-5-nitro-phenyl)-5-methyl-2,5,6,7-tetrahydro-1,4-oxazepin-3-ylamine (1.0 mmol) in ethanol (9 ml) and Pd/C (10%, 100 mg) was hydrogenated at 22° C. and atmospheric pressure for 2 h. The suspension was filtered and the residue evaporated to give (5R,6R)-5-(5-amino-2-fluoro-phenyl)-6-fluoro-5-methyl-2,5,6,7-tetrahydro-1,4-oxazepin-3-ylamine as a yellow solid. MS (ISP): m/z=256.3 [M+H]$^+$.

General Procedure for Syntheses of Intermediate Anilines A10 Via Alternative Reduction Method of Intermediate Nitrobenzenes A11

To a solution of nitrobenzene (140 mg, 0.47 mmol) in 4.0 ml EtOH was added SnCl$_2$.2H$_2$O (321 mg, 1.42 mmol) (precipitate formed instantly which dissolved upon heating). Reaction stirred at 80° C. for 1.5 h and controlled by TLC Si—NH$_2$ (CH$_2$Cl$_2$/MeOH/NH$_4$OH 80:18:2) which showed complete conversion. Reaction mixture poured into an aqueous solution NaOH 1N, addition of ethyl acetate and the mixture was stirred for 10 min. Precipitate was filtered over Celite®, the two phases in the filtrate were separated. The organic phase was dried over Na$_2$SO$_4$, filtered and evaporated down to dryness. The residue was purified by chromatography on an amine-modified silica with a mixture of CH$_2$Cl$_2$ and MeOH to give the pure aniline.

Intermediate A10C

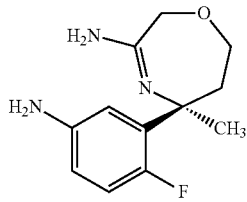 [SMILES: C[C@@]1(c2cc([N+](=O)[O-])ccc2F)CCOCC(N)=N1]

Starting from (S)-5-(2-fluoro-5-nitro-phenyl)-5-methyl-2,5,6,7-tetrahydro-1,4-oxazepin-3-ylamine, the product (S)-5-(5-amino-2-fluoro-phenyl)-5-methyl-2,5,6,7-tetrahydro-1,4-oxazepin-3-ylamine was obtained as an orange oil. MS (ISP): m/z=237.9 [M+H]$^+$.

Intermediate A10D

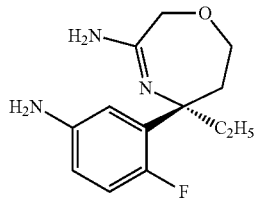

Starting from (S)-5-ethyl-5-(2-fluoro-5-nitro-phenyl)-2,5,6,7-tetrahydro-1,4-oxazepin-3-ylamine, the product (S)-5-(5-amino-2-fluoro-phenyl)-5-ethyl-2,5,6,7-tetrahydro-1,4-oxazepin-3-ylamine was obtained as an orange oil. MS (ISP): m/z=252.3 [M+H]$^+$.

Intermediate A10F

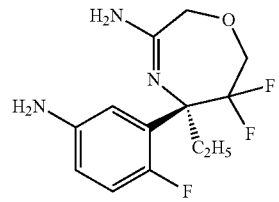 [SMILES: CC[C@]1(c2cc([N+](=O)[O-])ccc2F)N=C(N)COCC1(F)F]

Starting from (R)-5-ethyl-6,6-difluoro-5-(2-fluoro-5-nitro-phenyl)-2,5,6,7-tetrahydro-[1,4]oxazepin-3-ylamine (intermediate A11E), the product (R)-5-(5-amino-2-fluoro-phenyl)-5-ethyl-6,6-difluoro-2,5,6,7-tetrahydro-[1,4]oxazepin-3-ylamine was obtained by catalytic hydrogenation as a light yellow solid. MS (ISP): m/z=288.1 [M+H]$^+$.

Intermediate A12A

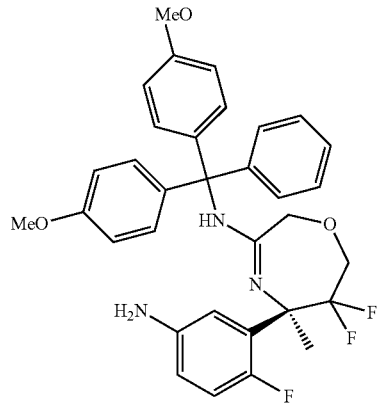 [SMILES: COc1ccc(C(NC2=N[C@](C)(c3cc(N)ccc3F)C(F)(F)COC2)(c2ccccc2)c2ccc(OC)cc2)cc1]

To a solution of (R)—N-(bis(4-methoxyphenyl)(phenyl)methyl)-5-(5-(diphenylmethyleneamino)-2-fluorophenyl)-6,6-difluoro-5-methyl-2,5,6,7-tetrahydro-1,4-oxazepin-3-amine (intermediate A9A) (3.55 g, 4.8 mmol) in dioxane (100 ml) at 23° C. was added 1 M hydrochloric acid (4.8 ml, 4.8 mmol) and the mixture was stirred at 23° C. for 3 h. The reaction mixture was concentrated in vacuum and the residue was purified by silica gel flash chromatography with n-heptane/ethyl acetate to give the [(R)-5-(5-amino-2-fluoro-phenyl)-6,6-difluoro-5-methyl-2,5,6,7-tetrahydro-[1,4]oxazepin-3-yl]-[bis-(4-methoxy-phenyl)-phenyl-methyl]-amine (1.45 g, 52%) as a white foam. MS (ISP): m/z=576.5 [M+H]$^+$.

Intermediate A13A

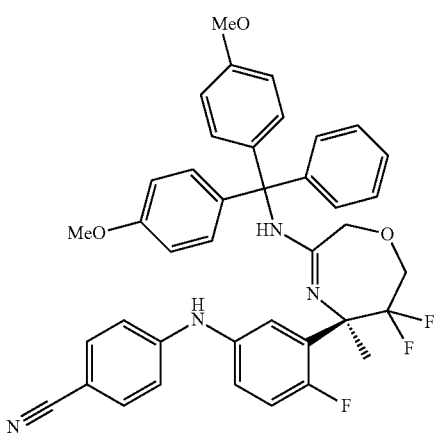 [SMILES: COc1ccc(C(NC2=N[C@](C)(c3cc(Nc4ccc(C#N)cc4)ccc3F)C(F)(F)COC2)(c2ccccc2)c2ccc(OC)cc2)cc1]

To a solution of [(R)-5-(5-amino-2-fluoro-phenyl)-6,6-difluoro-5-methyl-2,5,6,7-tetrahydro-[1,4]oxazepin-3-yl]-[bis-(4-methoxy-phenyl)-phenyl-methyl]-amine (intermediate A12A) (40 mg, 69.5 µmol) in toluene (0.6 ml) in a sealable tube was added subsequently at 23° C. and under an argon atmosphere 4-bromobenzonitrile (25.3 mg, 139 µmol), sodium tert-butoxide (13.4 mg, 139 µmol), 2-di-t-butylphosphino-2',4',6'-triisopropylbiphenyl (2.95 mg, 6.95 µmol) and tris(dibenzylideneacetone) dipalladium chloroform adduct (2.16 mg, 2.08 µmol), the tube was sealed and heated to 105 to 110° C. for 17 h. The mixture was cooled to 23° C., partitioned between saturated aqueous NaHCO$_3$ and ethyl acetate, the organic layer was dried and evaporated to give the crude product, which was purified by silica gel flash chromatography with n-heptane/ethyl acetate and trituration with diethyl ether/pentane to give the (R)-4-(3-(3-(bis(4-methoxyphenyl)(phenyl)methylamino)-6,6-difluoro-5-methyl-2,5,6,7-tetrahydro-1,4-oxazepin-5-yl)-4-fluorophenylamino)benzonitrile (23 mg, 49%) as a light yellow crystalline. MS (ISN): m/z=675.5 [M−H]$^-$.

Intermediate A13B

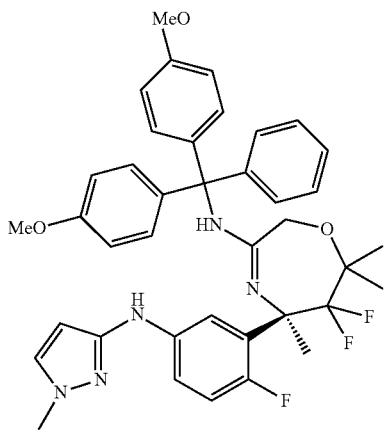 [SMILES: COc1ccc(C(NC2=N[C@](C)(c3cc(Nc4ccn(C)n4)ccc3F)C(F)(F)C(C)(C)OC2)(c2ccccc2)c2ccc(OC)cc2)cc1]

Prepared in an analogous manner as described for intermediate A9A or A13A from (R)—N-(bis(4-methoxyphenyl)(phenyl)methyl)-5-(5-bromo-2-fluorophenyl)-6,6-difluoro-5,7,7-trimethyl-2,5,6,7-tetrahydro-1,4-oxazepin-3-amine (intermediate A8B) (210 mg, 315 µmol) and commercially available 1-methyl-1H-pyrazol-3-amine [CAS no 1904-31-0] (62.4 mg, 629 µmol). The (R)—N-(bis(4-methoxyphenyl)(phenyl)methyl)-6,6-difluoro-5-(2-fluoro-5-(1-methyl-1H-pyrazol-3-ylamino)phenyl)-5,7,7-trimethyl-2,5,6,7-tetrahydro-1,4-oxazepin-3-amine (174 mg, 80.9%) was obtained as a light yellow foam. MS (ISP): m/z=684 [M+H]$^+$.

Intermediate A14A (S)-4-Amino-4-(5-bromo-2-fluoro-phenyl)-2-methyl-pentan-2-ol

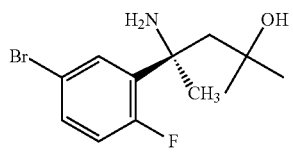 [SMILES: CC(C)(O)C[C@](C)(N)c1cc(Br)ccc1F]

The compound was prepared in an analogous manner as described for intermediate A6 from (R)-2-methyl-propane-2-sulfinic acid [(S)-1-(5-bromo-2-fluoro-phenyl)-3-hydroxy-1,3-dimethyl-butyl]-amide (intermediate A'1A) (10.8 g; 27 mmol; 85% purity). After silica gel column chromatography the compound was obtained as a light brown solid (2.22 g, 33%). MS (ISP): m/z=290.0 [(M+H)$^+$] and 292.0 [(M+2+H)$^+$].

Intermediate A14B (R)-3-Amino-3-(5-bromo-2-fluoro-phenyl)-2,2-difluoro-butan-1-ol

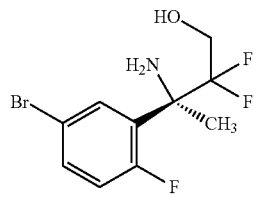 [SMILES: C[C@@](N)(c1cc(Br)ccc1F)C(F)(F)CO]

The compound was prepared in an analogous manner as described for intermediate A6 from (S)—N—((R)-2-(5-bromo-2-fluorophenyl)-3,3-difluoro-4-hydroxybutan-2-yl)-2-methylpropane-2-sulfinamide (intermediate A4B) (3.706 g, 9.21 mmol) to give the title compound as an orange viscous oil (2.96 g, 90% purity, 97% yield). MS (ISP): m/z=298.2 [(M+H)$^+$] and 300.2 [(M+2+H)$^+$].

Intermediate A15A

N—[(S)-1-(5-Bromo-2-fluoro-phenyl)-3-hydroxy-1,3-dimethyl-butyl]-2-chloro-acetamide

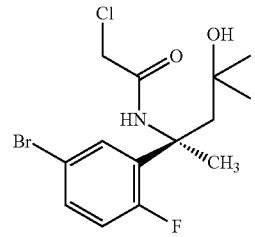

To a vigorously stirred mixture of (S)-4-amino-4-(5-bromo-2-fluoro-phenyl)-2-methyl-pentan-2-ol (intermediate A14A) (2.22 g; 7.7 mmol) in sat. aqueous NaHCO$_3$-sol. (25 ml) and dichloromethane (DCM) (35 ml) at 0° C. was added chloroacetyl chloride (672 µl, 8.5 mmol) and the mixture was stirred at 0° C. for 30 min Diluted with water, brine and ethyl acetate (EtOAc), separated phases, dried organic layer over sodium sulphate. Removal of the solvent in vacuum left the crude product as a colourless oil (3.11 g, 111%), which was used in the next step without further purification. MS (ISP): m/z=366.0 [(M+H)$^+$], 368.0 [(M+2+H)$^+$] and 370.0 [(M+4+H)$^+$].

Intermediate A15B

2-Bromo-N—[(R)-1-(5-bromo-2-fluoro-phenyl)-2,2-difluoro-3-hydroxy-1-methyl-propyl]-acetamide

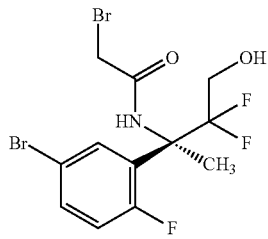 [SMILES: C[C@@](NC(=O)CBr)(c1cc(Br)ccc1F)C(F)(F)CO]

Prepared in an analogous manner as described for intermediate A15A from (R)-3-amino-3-(5-bromo-2-fluoro-phenyl)-2,2-difluoro-butan-1-ol (intermediate A14B) (2.96 g, 9.93 mmol) and bromoacetyl chloride (1.72 g, 914 µl, 10.9 mmol). Obtained was the title compound as an off-white solid. MS (ISP): m/z=418.0 [(M+H)$^+$], 420.0 [(M+2+H)$^+$] and 422.0 [(M+4+H)$^+$].

Intermediate A16A (S)-5-(5-Bromo-2-fluoro-phenyl)-5,7,7-trimethyl-[1,4]oxazepan-3-one

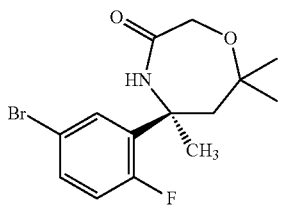 [SMILES: CC1(C)C[C@@](C)(c2cc(Br)ccc2F)NC(=O)CO1]

To a solution of N—[(S)-1-(5-bromo-2-fluoro-phenyl)-3-hydroxy-1,3-dimethyl-butyl]-2-chloro-acetamide (intermediate A15A) (3.11 g, 8.5 mmol) in toluene (150 ml) at 23° C. was added dropwise a solution of potassium amylate (1.7 M in toluene; 25.0 ml, 42 mmol) within 10 min (slightly exothermic). The light brown solution was stirred at 23° C. for 2 h. Diluted with water, 1N HCl and brine and extracted twice with ethyl acetate. The organic layers were washed with sat. NaHCO$_3$ solution and brine, dried over Na$_2$SO$_4$, filtered and evaporated to give a light brown oil, which was purified by silica gel column chromatography with n-heptane/ethyl acetate to give the title compound as an off-white solid (1.05 g, 37%). MS (ISP): m/z=330.0 [(M+H)$^+$] and 332.0 [(M+2+H)$^+$].

Intermediate A16B (R)-5-(5-bromo-2-fluorophenyl)-6,6-difluoro-5,7,7-trimethyl-[1,4]oxazepan-3-one

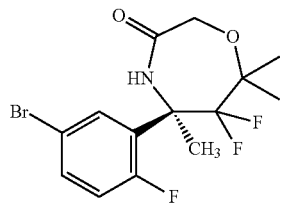 [SMILES: CC1(C)OCC(=O)N[C@](C)(c2cc(Br)ccc2F)C1(F)F]

To a solution of (R)-ethyl 2-(4-amino-4-(5-bromo-2-fluorophenyl)-3,3-difluoro-2-methylpentan-2-yloxy)acetate (intermediate A27A) (6.85 g, 16.6 mmol) in toluene (205 ml) at 23° C. was dropwise added trimethylaluminum (2 M in toluene, 10.8 ml, 21.6 mmol) and the light yellow solution was stirred at 23° C. for 2 h. Poured into sat. NaHCO$_3$-sol., extracted with ethyl acetate, washed organic layer with brine, dried over Na$_2$SO$_4$, filtered off and evaporated totally, dried in high vacuum to give the (R)-5-(5-bromo-2-fluorophenyl)-6,6-difluoro-5,7,7-trimethyl-1,4-oxazepan-3-one (5.95 g, 16.2 mmol, 97.8% yield) as a light yellow solid, which was used without further purification. MS (ISP): m/z=366.2 [(M+H)$^+$] and 368.1 [(M+2+H)$^+$].

Intermediate A16C (R)-5-(5-bromo-2,4-difluorophenyl)-6,6-difluoro-5,7,7-trimethyl-[1,4]oxazepan-3-one

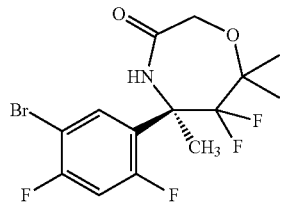 [SMILES: CC1(C)OCC(=O)N[C@](C)(c2cc(Br)c(F)cc2F)C1(F)F]

Prepared in an analogous manner as described for intermediate A27A from (R)-ethyl 2-(4-amino-4-(5-bromo-2,4-difluorophenyl)-3,3-difluoro-2-methylpentan-2-yloxy)acetate (intermediate A27B) (16.1 g; 37.4 mmol). After silica gel column chromatography with heptane and ethyl acetate the (R)-5-(5-bromo-2,4-difluorophenyl)-6,6-difluoro-5,7,7-trimethyl-[1,4]oxazepan-3-one (9.0 g, 23.4 mmol, 63% yield) was obtained as an off-white solid. MS (ISP): m/z=384.2 [(M+H)$^+$] and 386.1 [(M+2+H)$^+$].

Intermediate A16D (R)-5-(5-Bromo-2-fluoro-phenyl)-6,6-difluoro-5-methyl-[1,4]oxazepan-3-one

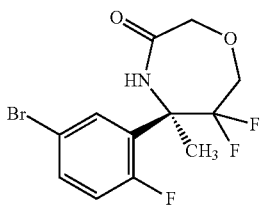 [SMILES: C[C@]1(c2cc(Br)ccc2F)NC(=O)COCC1(F)F]

Prepared in an analogous manner as described for intermediate A27A from 2-Bromo-N—[(R)-1-(5-bromo-2-fluoro-phenyl)-2,2-difluoro-3-hydroxy-1-methyl-propyl]-acetamide (intermediate A15B) (700 mg; 2.82 mmol). After silica gel column chromatography with heptane and ethyl acetate the (R)-5-(5-bromo-2-fluoro-phenyl)-6,6-difluoro-5-methyl-[1,4]oxazepan-3-one (366 mg, 1.83 mmol, 65% yield) was obtained as a white solid. MS (ISP): m/z=337.0 [(M+H)$^+$] and 339.0 [(M+2+H)$^+$].

Intermediate A17A (S)-5-[5-(Benzhydrylidene-amino)-2-fluoro-phenyl]-5,7,7-trimethyl-[1,4]oxazepan-3-one

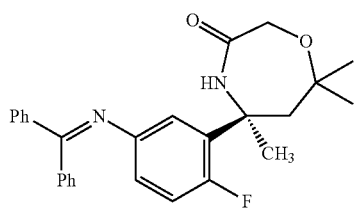 [SMILES: CC1(C)C[C@@](C)(c2cc(N=C(c3ccccc3)c3ccccc3)ccc2F)NC(=O)CO1]

Under argon in a sealed tube was added to a solution of (S)-5-(5-bromo-2-fluoro-phenyl)-5,7,7-trimethyl-[1,4]oxazepan-3-one (intermediate A16A) (1.0 g, 3.0 mmol) in toluene (20 ml), sodium tert-butoxide (NaOBu$^t$) (865 mg, 9.0 mmol), 2-di-tert-butylphosphino-2',4',6'-triisopropylbiphenyl (t-Bu X-phos) (127 mg, 10 mol %) and tris(dibenzylideneacetone)dipalladium chloroform complex (Pd$_2$(dba)$_3$. CHCl$_3$) (93 mg, 3 mol %) followed by benzophenone imine (1.07 mL, 6.0 mmol). The tube was sealed under argon and the mixture was stirred at 105° C. for 18 h to 2.5 days. The mixture was cooled to 23° C., poured into water, extracted with ethyl acetate, and the organic layer was washed with brine and dried over sodium sulphate. Removal of the solvent in vacuum left a brown oil, which was purified by silica gel column chromatography with n-heptane/ethyl acetate to give the (S)-5-[5-(benzhydrylidene-amino)-2-fluoro-phenyl]-5,7,7-trimethyl-[1,4]oxazepan-3-one (1.15 g, 88%) as light yellow foam. MS (ISP): m/z=431.3 [(M+H)$^+$].

Intermediate A17B (R)-5-(5-(diphenylmethyleneamino)-2-fluorophenyl)-6,6-difluoro-5,7,7-trimethyl-[1,4]oxazepan-3-one

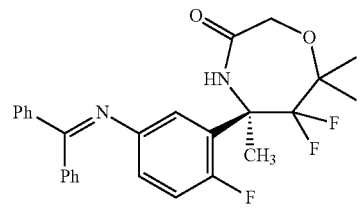 [SMILES: CC1(C)OCC(=O)N[C@](C)(c2cc(N=C(c3ccccc3)c3ccccc3)ccc2F)C1(F)F]

The compound was prepared in an analogous manner as described for intermediate A17A below from (R)-5-(5-bromo-2-fluorophenyl)-6,6-difluoro-5,7,7-trimethyl-[1,4]oxazepan-3-one (intermediate A16B) (1.03 g, 2.81 mmol). The compound was obtained as yellow solid (1.05 g, 2.25 mmol, 80%). MS (ISP): m/z=467.3 [(M+H)$^+$].

Intermediate A17C (R)-5-(5-(diphenylmethyleneamino)-2,4-difluorophenyl)-6,6-difluoro-5,7,7-trimethyl-[1,4]oxazepan-3-one

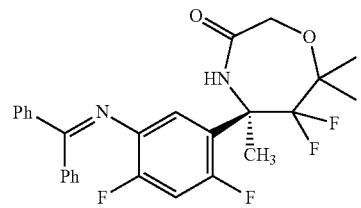 [SMILES: CC1(C)OCC(=O)N[C@](C)(c2cc(N=C(c3ccccc3)c3ccccc3)c(F)cc2F)C1(F)F]

The compound was prepared in an analogous manner as described for intermediate A17A below from (R)-5-(5-bromo-2,4-difluorophenyl)-6,6-difluoro-5,7,7-trimethyl-[1,4]oxazepan-3-one (intermediate A16C) (1.5 g, 3.9 mmol). The compound was obtained as a light yellow foam (0.75 g, 1.55 mmol, 40%). MS (ISP): m/z=485.3 [(M+H)$^+$].

Intermediate A17D (R)-5-[5-(Benzhydrylidene-amino)-2-fluoro-phenyl]-6,6-difluoro-5-methyl-[1,4]oxazepan-3-one

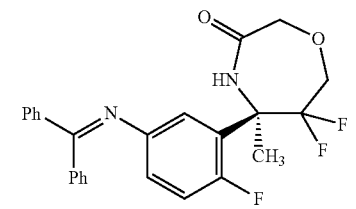 [SMILES: C[C@]1(c2cc(N=C(c3ccccc3)c3ccccc3)ccc2F)NC(=O)COCC1(F)F]

The compound was prepared in an analogous manner as described for intermediate A17A below from (R)-5-(5-bromo-2-fluoro-phenyl)-6,6-difluoro-5-methyl-[1,4]oxazepan-3-one (intermediate A16D) (355 mg, 1.05 mmol). The compound was obtained as yellow foam (308 mg, 0.70 mmol, 67%). MS (ISP): m/z=439.2 [(M+H)+].

Intermediate A19A (S)-5-(5-Amino-2-fluoro-phenyl)-5,7,7-trimethyl-[1,4]oxazepane-3-thione

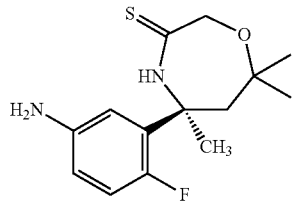 [SMILES: CC1(C)C[C@@](C)(c2cc(N)ccc2F)NC(=S)CO1]

To a solution of (S)-5-[5-(benzhydrylidene-amino)-2-fluoro-phenyl]-5,7,7-trimethyl-[1,4]oxazepan-3-one (intermediate A17A) (1.15 g, 2.7 mmol) in dioxane (80 ml) at 23° C. was added 2,4-bis-(4-methoxy-phenyl)-[1,3,2,4]dithiadiphosphetane 2,4-disulfide (Lawesson's reagent) (681 mg, 1.7 mmol) and the mixture was stirred at 80° C. for 2 h to obtain a crude solution of the (S)-5-[5-(benzhydrylideneamino)-2-fluoro-phenyl]-5,7,7-trimethyl-[1,4]oxazepane-3-thione (intermediate A18A), which was cooled to 23° C. and 1 M HCl (3.4 ml, 3.4 mmol) was added. After 30 min of stirring, the reaction mixture was poured on sat. NaHCO₃-solution and extracted twice with ethyl acetate. The combined organic layers were washed with brine, dried over sodium sulfate, filtered and evaporated to give a dark green oil, which was purified by silica gel column chromatography with dichloromethane/ethyl acetate to give the (S)-5-(5-amino-2-fluoro-phenyl)-5,7,7-trimethyl-[1,4]oxazepane-3-thione (575 mg, 76%) as a light brown foam. MS (ISP): m/z=283.1 [(M+H)+].

Intermediate A19B (R)-5-(5-amino-2-fluorophenyl)-6,6-difluoro-5,7,7-trimethyl-[1,4]oxazepane-3-thione

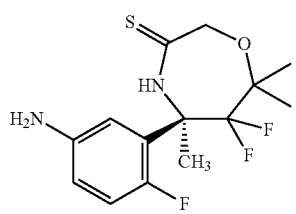 [SMILES: CC1(C)OCC(=S)N[C@](C)(c2cc(N)ccc2F)C1(F)F]

The compound was prepared in an analogous manner as described for intermediate A19A from (R)-5-(5-(diphenylmethyleneamino)-2-fluorophenyl)-6,6-difluoro-5,7,7-trimethyl-[1,4]oxazepan-3-one (intermediate A17B) (3.13 g, 6.71 mmol). The compound was obtained as yellow foam (1.0 g, 3.14 mmol, 47%). MS (ISP): m/z=319.2 [(M+H)+].

Intermediate A19C (R)-5-(5-Amino-2,4-difluorophenyl)-6,6-difluoro-5,7,7-trimethyl-[1,4]oxazepane-3-thione

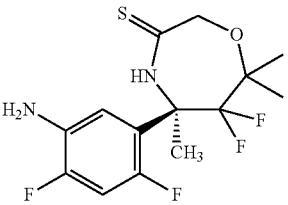 [SMILES: CC1(C)OCC(=S)N[C@](C)(c2cc(N)c(F)cc2F)C1(F)F]

The compound was prepared in an analogous manner as described for intermediate A19A from (R)-5-(5-(diphenylmethyleneamino)-2,4-difluorophenyl)-6,6-difluoro-5,7,7-trimethyl-[1,4]oxazepan-3-one (intermediate A17C) (0.75 g, 1.55 mmol). The compound was obtained as a light yellow foam (0.29 g, 0.86 mmol, 56%). MS (ISP): m/z=337.2 [(M+H)+].

Intermediate A20A (R)-5-[5-(3-Chloro-6,7-dihydro-5H-[1]pyrindin-7-ylamino)-2-fluoro-phenyl]-6,6-difluoro-5-methyl-[1,4]oxazepane-3-thione

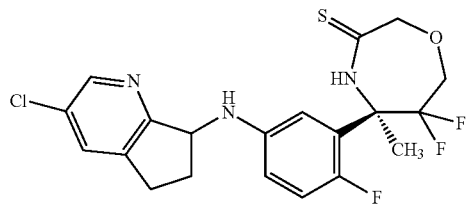

To a solution of (5R)-5-(5-(3-chloro-6,7-dihydro-5H-cyclopenta[b]pyridin-7-ylamino)-2-fluorophenyl)-6,6-difluoro-5-methyl-1,4-oxazepan-3-one (intermediate A22A) (62 mg, 146 μmmol) in dioxane (2.2 ml) at 23° C. was added 2,4-bis-(4-methoxy-phenyl)-[1,3,2,4]dithiadiphosphetane 2,4-disulfide (Lawesson's reagent) (38.3 mg, 94.6 μmmol) and the mixture was stirred at 80° C. for 3 h. The reaction mixture was poured onto sat. NaHCO₃-solution and extracted twice with ethyl acetate. The combined organic layers were washed with brine, dried over sodium sulfate, filtered and evaporated to give a yellow solid, which was purified by silica gel column chromatography with n-heptane/ethyl acetate to give the (R)-5-[5-(3-chloro-6,7-dihydro-5H-[1]pyrindin-7-ylamino)-2-fluoro-phenyl]-6,6-difluoro-5-methyl-[1,4]oxazepane-3-thione (54 mg, 84%) as a white solid. MS (ISP): m/z=443.0 [(M+H)+].

Intermediate A20Aa (R)-5-[5-((R)-3-Chloro-6,7-dihydro-5H-[1]pyrindin-7-ylamino)-2-fluoro-phenyl]-6,6-difluoro-5-methyl-[1,4]oxazepane-3-thione

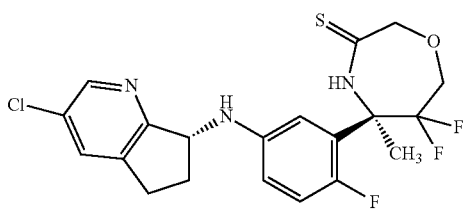

Obtained from (R)-5-[5-(3-chloro-6,7-dihydro-5H-[1]pyrindin-7-ylamino)-2-fluoro-phenyl]-6,6-difluoro-5-methyl-[1,4]oxazepane-3-thione (intermediate A20A) (50 mg) by chromatography on a Chiralpak AD column with 40% ethanol in n-heptane being the less polar eluting epimer (A(−)) as a yellow solid (20 mg). MS (ISP): m/z=443.0 [(M+H)$^+$].

Intermediate A20Ab (R)-5-[5-((S)-3-Chloro-6,7-dihydro-5H-[1]pyrindin-7-ylamino)-2-fluoro-phenyl]-6,6-difluoro-5-methyl-[1,4]oxazepane-3-thione

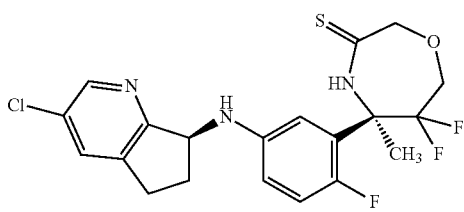 [SMILES: C[C@]1(c2cc(N[C@H]3CCc4cc(Cl)cnc43)ccc2F)NC(=S)COCC1(F)F]

Obtained from (R)-5-[5-(3-chloro-6,7-dihydro-5H-[1]pyrindin-7-ylamino)-2-fluoro-phenyl]-6,6-difluoro-5-methyl-[1,4]oxazepane-3-thione (intermediate A20A) (50 mg) by chromatography on a Chiralpak AD column with 40% ethanol in n-heptane being the more polar eluting epimer (B(−)) as a yellow solid (16 mg). MS (ISP): m/z=443.0 [(M+H)$^+$].

Intermediate A20B 7-(3-((R)-6,6-Difluoro-5,7,7-trimethyl-3-thioxo-1,4-oxazepan-5-yl)-4-fluorophenylamino)-6,7-dihydro-5H-cyclopenta[b]pyridine-3-carbonitrile

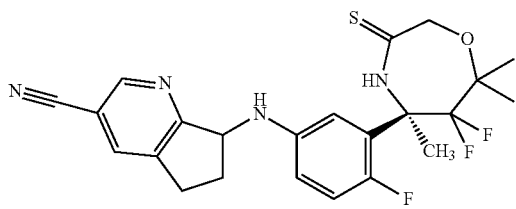 [SMILES: CC1(C)OCC(=S)N[C@](C)(c2cc(NC3CCc4cc(C#N)cnc43)ccc2F)C1(F)F]

Prepared in an analogous manner as described for intermediate A22A from (R)-5-(5-amino-2-fluorophenyl)-6,6-difluoro-5,7,7-trimethyl-1,4-oxazepane-3-thione (intermediate A19B) (305 mg, 958 μmol) and 7-oxo-6,7-dihydro-5H-[1]pyrindine-3-carbonitrile (167 mg, 1.05 mmol) The 7-(3-((R)-6,6-difluoro-5,7,7-trimethyl-3-thioxo-1,4-oxazepan-5-yl)-4-fluorophenylamino)-6,7-dihydro-5H-cyclopenta[b]pyridine-3-carbonitrile (370 mg, 84%) was obtained as a light yellow foam. MS (ISP): m/z=426.1 [(M+H)$^+$].

The 7-oxo-6,7-dihydro-5H-[1]pyrindine-3-carbonitrile was prepared as follows:

a) 6,7-Dihydro-5H-[1]pyrindine-3-carbonitrile

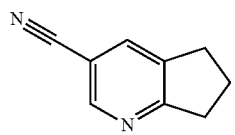 [SMILES: N#Cc1cnc2c(c1)CCC2]

A mixture of 3-chloro-6,7-dihydro-5H-[1]pyridine (7.1 g, 46.2 mmol), sodium carbonate (980 mg, 9.25 mmol), potassium hexacyanoferrate(II) trihydrates (7.81 g, 18.5 mmol), palladium(II) acetate (104 mg, 462 μmol) and butyldi-1-adamantylphosphine (497 mg, 1.39 mmol) was dissolved in N-methyl-2-pyrrolidinone (46.2 ml), the solution flushed with argon and heated to 160° C. for 16 hr. After cooling to 23° C., the mixture was poured into water, extracted with dichloromethane, the combined extracts dried over Na$_2$SO$_4$ and the solvent evaporated leaving a dark blue liquid. The crude material was purified by silica gel flash chromatography with n-heptane/ethyl acetate to give the 6,7-dihydro-5H-[1]pyrindine-3-carbonitrile as a white solid (4.82 g, 72%). MS (ISP): m/z=145.1 [(M+H)$^+$].

b) 1-Oxy-6,7-dihydro-5H-[1]pyrindine-3-carbonitrile

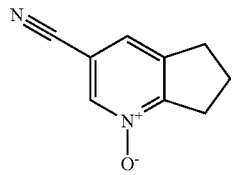 [SMILES: N#Cc1cc2c([n+]([O-])c1)CCC2]

To a solution of 6,7-dihydro-5H-[1]pyrindine-3-carbonitrile (6.23 g, 43.2 mmol) in acetic acid (54 ml) at 40° C. was portionwise added sodium perborate tetrahydrate (7.31 g, 47.5 mmol) and the mixture was stirred at 40° C. for 30 h. Added more sodium perborate tetrahydrate (1.05 g, 6.82 mmol) after 24 h. The acetic acid was removed by evaporation, the residue taken up in sat. NaHCO$_3$-sol., extracted with dichloromethane (3×150 mL), the combined organic layer was dried over Na$_2$SO$_4$. Removal of the solvent in vacuum left the 1-oxy-6,7-dihydro-5H-[1]pyrindine-3-carbonitrile (6.5 g, 39.2 mmol, 90.6%) as a white solid. MS (ISP): m/z=161.1 [(M+H)$^+$].

c) 7-Hydroxy-6,7-dihydro-5H-[1]pyrindine-3-carbonitrile

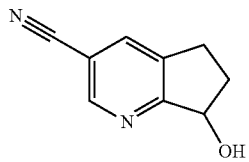 [SMILES: N#Cc1cnc2c(c1)CCC2O]

To a solution of 1-oxy-6,7-dihydro-5H-[1]pyrindine-3-carbonitrile (1.82 g, 11.4 mmol) in dichloromethane (40 ml) at 0° C. was added dropwise trifluoroacetic anhydride (14.3 g, 9.63 ml, 68.2 mmol) and the mixture was stirred at 0 to 23° C. for 18 h. Poured into icecold 1 N NaOH sol., stirred for 30 min and extracted twice with dichloromethane. The combined organic layer was dried over sodium sulfate, the solvent was removed in vacuum to leave a brown residue, which was purified by silica gel column chromatography with n-heptane/ethyl acetate to give the 7-hydroxy-6,7-dihydro-5H-[1]pyrindine-3-carbonitrile (1.14 g, 7.12 mmol, 62.6%) as a yellow solid. MS (ISP): m/z=161.1 [(M+H)$^+$].

d) 7-Oxo-6,7-dihydro-5H-[1]pyrindine-3-carbonitrile

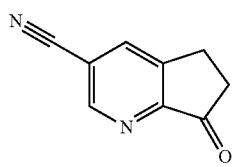 [SMILES: N#Cc1cnc2c(c1)CCC2=O]

To a solution of 7-hydroxy-6,7-dihydro-5H-[1]pyrindine-3-carbonitrile (1.05 g, 6.56 mmol) in dichloromethane (50 ml) at 0° C. was added Dess-Martin periodinane (2.92 g, 6.88 mmol) and the mixture was stirred at 23° C. for 2 hours. Poured on 1 M Na$_2$CO$_3$-sol. and extracted twice with dichloromethane. The organic layers were washed with diluted NaHSO$_3$ solution and brine, dried over Na$_2$SO$_4$, filtered and evaporated to give a grey solid. The residue was purified by silica gel flash chromatography with n-heptane/ethyl acetate to give the 7-oxo-6,7-dihydro-5H-[1]pyrindine-3-carbonitrile (855 mg, 5.14 mmol, 78.3%) as a dark green solid. MS (ISP): m/z=159.1 [(M+H)$^+$].

Intermediate A20Ba (S)-7-[3-((R)-6,6-Difluoro-5,7,7-trimethyl-3-thioxo-[1,4]oxazepan-5-yl)-4-fluoro-phenylamino]-6,7-dihydro-5H-[1]pyrindine-3-carbonitrile

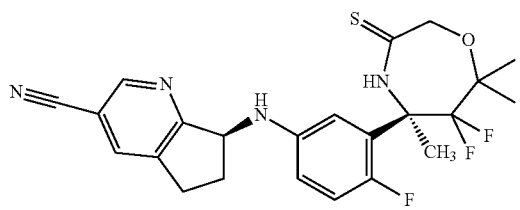 [SMILES: CC1(C)OCC(=S)N[C@](C)(c2cc(N[C@H]3CCc4cc(C#N)cnc43)ccc2F)C1(F)F]

Obtained from 7-(3-((R)-6,6-difluoro-5,7,7-trimethyl-3-thioxo-1,4-oxazepan-5-yl)-4-fluorophenylamino)-6,7-dihydro-5H-cyclopenta[b]pyridine-3-carbonitrile (intermediate A20B) (370 mg, 803 µmol) by chromatography on a Chiralpak AD column with 30% ethanol in n-heptane being the less polar eluting epimer (A(−)) as a light brown foam (158 mg, 343 µmol, 42.7%). MS (ISP): m/z=461.3 [(M+H)$^+$].

Intermediate A20Bb (R)-7-(3-((R)-6,6-difluoro-5,7,7-trimethyl-3-thioxo-1,4-oxazepan-5-yl)-4-fluorophenylamino)-6,7-dihydro-5H-cyclopenta[b]pyridine-3-carbonitrile

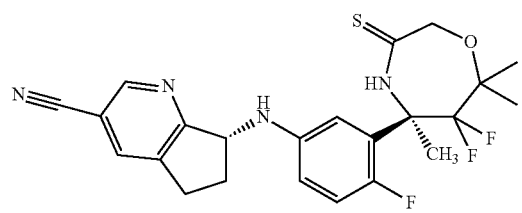 [SMILES: CC1(C)OCC(=S)N[C@](C)(c2cc(N[C@@H]3CCc4cc(C#N)cnc43)ccc2F)C1(F)F]

Obtained from 7-(3-((R)-6,6-difluoro-5,7,7-trimethyl-3-thioxo-1,4-oxazepan-5-yl)-4-fluorophenylamino)-6,7-dihydro-5H-cyclopenta[b]pyridine-3-carbonitrile (intermediate A20B) (370 mg, 803 µmol) by chromatography on a Chiralpak AD column with 30% ethanol in n-heptane being the more polar eluting epimer (B(−)) as a light brown foam (145 mg, 315 µmol, 39.2%). MS (ISP): m/z=461.3 [(M+H)$^+$].

Intermediate A20C (R)-5-[5-(3-Chloro-6,7-dihydro-5H-[1]pyrindin-7-ylamino)-2-fluoro-phenyl]-6,6-difluoro-5,7,7-trimethyl-[1,4]oxazepane-3-thione

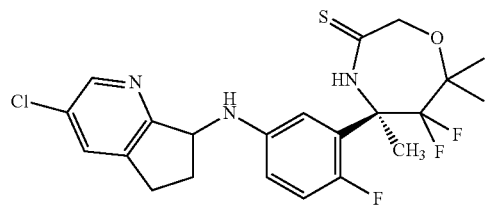 [SMILES: CC1(C)OCC(=S)N[C@](C)(c2cc(NC3CCc4cc(Cl)cnc43)ccc2F)C1(F)F]

Prepared in an analogous manner as described for intermediate A22A from (R)-5-(5-amino-2-fluorophenyl)-6,6-difluoro-5,7,7-trimethyl-1,4-oxazepane-3-thione (intermediate A19B) (72.3 mg, 227 µmol) and 3-chloro-5,6-dihydro-[1]pyrindin-7-one (34.6 mg, 206 µmol) The (R)-5-[5-(3-chloro-6,7-dihydro-5H-[1]pyrindin-7-ylamino)-2-fluoro-phenyl]-6,6-difluoro-5,7,7-trimethyl-[1,4]oxazepane-3-thione (82 mg, 84%) was obtained as a white foam. MS (ISP): m/z=470.2 [(M+H)$^+$] and 472.3 [(M+2+H)$^+$].

Intermediate A20D (5R)-5-(5-(6-chloro-2,3-dihydrofuro[3,2-b]pyridin-3-ylamino)-2-fluorophenyl)-6,6-difluoro-5,7,7-trimethyl-1,4-oxazepane-3-thione

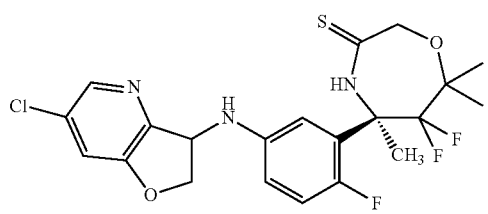 [SMILES: CC1(C)OCC(=S)N[C@](C)(c2cc(NC3COc4cc(Cl)cnc43)ccc2F)C1(F)F]

Prepared in an analogous manner as described for intermediate A22A from (R)-5-(5-amino-2-fluorophenyl)-6,6-difluoro-5,7,7-trimethyl-1,4-oxazepane-3-thione (intermediate A19B) (100 mg, 314 µmol) and 6-chloro-furo[3,2-b]pyridin-3-one (63.9 mg, 377 µmol) The (5R)-5-(5-(6-chloro-2,3-dihydrofuro[3,2-b]pyridin-3-ylamino)-2-fluorophenyl)-6,6-difluoro-5,7,7-trimethyl-1,4-oxazepane-3-thione (67 mg, 45.2%) was obtained as a light yellow foam. MS (ISN): m/z=470.2 [(M−H)⁻] and 472.1 [(M+2−H)⁻].

The 6-chloro-furo[3,2-b]pyridin-3-one was prepared as follows:

a) 5-Chloro-2-iodopyridin-3-ol

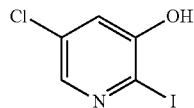

To a solution of 5-chloropyridin-3-ol [CAS no 74115-12-1] (15 g, 116 mmol) in sodium carbonate (1 M in water, 232 ml, 232 mmol) at 23° C. was portionwise added iodine (29.4 g, 116 mmol) and the mixture was stirred for 5 h. Poured onto 1 M hydrochloric acid (300 ml), adjusted pH by additional hydrochloric acid to pH 1, the precipitate was filtered off, washed with water, dissolved in ethyl acetate, the organic layer was dried over Na₂SO₄. Removal of the solvent in vacuum left the 5-chloro-2-iodopyridin-3-ol (28.33 g, 111 mmol, 95.8% yield) as a light brown solid. MS (ISP): m/z=256.1 [(M+H)⁺] and 258.2 [(M+2+H)⁺].

b) Ethyl 2-(5-chloro-2-iodopyridin-3-yloxy)acetate

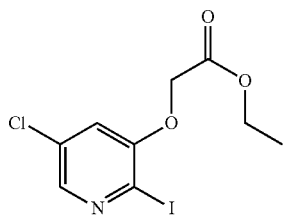

To a solution of 5-chloro-2-iodopyridin-3-ol (15 g, 58.7 mmol) in N,N-dimethylformamide (150 ml) at 0° C. was added cesium carbonate (47.8 g, 147 mmol) and ethyl bromoacetate (14.7 g, 9.81 ml, 88.1 mmol) and the mixture was stirred at 23° C. for 18 h. Poured into brine, extracted thrice with ethyl acetate, dried the combined organic layer over sodium sulfate. Removal of the solvent in vacuum left an oil, which was diluted with tert-butyl methyl ether, washed with water and brine and dried over sodium sulfate. Removal of the solvent in vacuum left a light brown oil, which was purified by silica gel column chromatography with n-heptane/ethyl acetate to give the ethyl 2-(5-chloro-2-iodopyridin-3-yloxy)acetate (17.3 g, 50.7 mmol, 86.3% yield) as a light brown solid. MS (ISP): m/z=341.9 [(M+H)⁺] and 343.9 [(M+2+H)⁺].

c) Ethyl 5-chloro-3-(2-ethoxy-2-oxoethoxy)picolinate

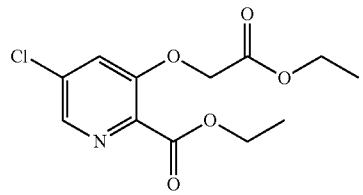 [SMILES: CCOC(=O)COc1cc(Cl)cnc1C(=O)OCC]

Ethyl 2-(5-chloro-2-iodopyridin-3-yloxy)acetate (16.5 g, 48.3 mmol) was carbonylated with 20 bar carbon monoxide in the presence of bis(diphenylphosphino)ferrocene-palladium(II)dichloride dichloromethane adduct (1.66 g, 2.03 mmol) in a mixture of ethanol, ethyl acetate and triethylamine at 70° C. for 20 h. The crude reaction mixture was extracted with ethyl acetate and water, the organic layer was dried over sodium sulfate. Removal of the solvent in vacuum left a dark brown oil, which was purified by silica gel column chromatography with n-heptane/ethyl acetate to give the ethyl 5-chloro-3-(2-ethoxy-2-oxoethoxy)picolinate (12.5 g, 43.4 mmol, 89.9% yield) as a light red solid. MS (ISP): m/z=287.9 [(M+H)⁺] and 290.1 [(M+2+H)⁺].

d) Ethyl 6-chloro-3-hydroxyfuro[3,2-b]pyridine-2-carboxylate

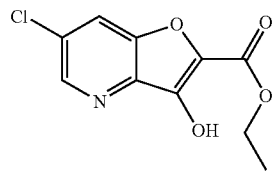 [SMILES: CCOC(=O)c1oc2cc(Cl)cnc2c1O]

To a solution of ethyl 5-chloro-3-(2-ethoxy-2-oxoethoxy)picolinate (385 mg, 1.34 mmol) in toluene (10 ml) at 23° C. was added sodium ethoxide (200 mg, 2.94 mmol) and the reaction mixture was stirred at reflux overnight. To the yellow suspension was added some ice, ethyl acetate and set to pH=4 with acetic acid. The organic layer was separated and washed with sat NaHCO₃ solution. The aqueous layers were reextracted with ethyl acetate, then dried over Na₂SO₄, filtered and evaporated to give the crude ethyl 6-chloro-3-hydroxyfuro[3,2-b]pyridine-2-carboxylate (154 mg, 637 µmol, 47.6% yield) as a light brown solid. MS (ISN): m/z=240.1 [(M−H)⁻] and 242.3 [(M+2−H)⁻].

e) 6-Chloro-furo[3,2-b]pyridin-3-one

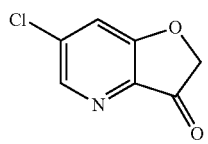 [SMILES: O=C1COc2cc(Cl)cnc21]

A mixture of ethyl 6-chloro-3-hydroxyfuro[3,2-b]pyridine-2-carboxylate (154 mg, 637 μmol) and 10% hydrochloric acid (4.65 g, 3.87 ml, 127 mmol) was stirred at 110° C. for 3 hours. To the cooled brown solution was added some ice and neutralized with sat NaHCO$_3$ to pH=8. Then the aqueous layer was extracted thrice with dichloromethane, the combined organic layers were washed with brine, dried over Na$_2$SO$_4$, filtered and evaporated to give a brown oil. The residue was purified by silica gel flash chromatography with dichloromethane toster) with CH$_2$Cl$_2$ to give the 6-chloro-furo[3,2-b]pyridin-3-one (79 mg, 466 μmol, 73.1% yield) as a light brown solid. MS (ISP): m/z=170.0 [(M+H)$^+$] and 172.0 [(M+2+H)$^+$].

Intermediate A20E 8-(3-((R)-6,6-Difluoro-5,7,7-trimethyl-3-thioxo-1,4-oxazepan-5-yl)-4-fluorophenylamino)-5,6,7,8-tetrahydroquinoline-3-carbonitrile

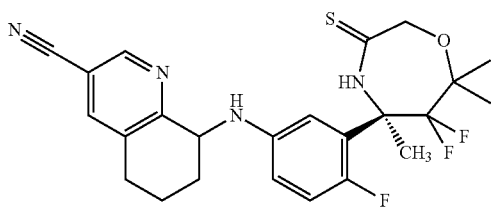 [SMILES: CC1(C)OCC(=S)N[C@](C)(c2cc(NC3CCCc4cc(C#N)cnc43)ccc2F)C1(F)F]

Prepared in an analogous manner as described for intermediate A22A from (R)-5-(5-amino-2-fluorophenyl)-6,6-difluoro-5,7,7-trimethyl-1,4-oxazepane-3-thione (intermediate A19B) (102 mg, 320 μmol) and 8-oxo-5,6,7,8-tetrahydroquinoline-3-carbonitrile (66.2 mg, 384 μmol). The 8-(3-((R)-6,6-difluoro-5,7,7-trimethyl-3-thioxo-1,4-oxazepan-5-yl)-4-fluorophenylamino)-5,6,7,8-tetrahydroquinoline-3-carbonitrile (96 mg, 63.1%) was obtained as a white foam. MS (ISN): m/z=473.1 [(M−H)$^-$].

The 8-oxo-5,6,7,8-tetrahydroquinoline-3-carbonitrile was prepared as follows:

a) 5,6,7,8-Tetrahydroquinoline-3-carbonitrile

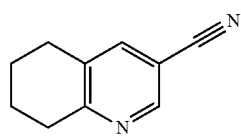 [SMILES: N#Cc1cnc2c(c1)CCCC2]

A mixture of commercially available 2-chloro-5,6,7,8-tetrahydroquinoline-3-carbonitrile [CAS no 65242-27-5] (1 g, 5.19 mmol), zinc dust (activated) (602 mg, 9.2 mmol) and sodium acetate trihydrate (694 mg, 479 μl, 5.1 mmol) in acetic acid (5.19 g, 4.95 ml, 86.4 mmol) was stirred at 60° C. for 2 hours. Water (2.5 ml) was added and the mixture stirred at 60° C. for another 5 hours. After cooling to 23° C., the mixture was basified with aqueous 1 M NaOH solution, filtered through Celite®, the filtrate extracted with THF, the organic layers dried over Na$_2$SO$_4$ and the solvent evaporated leaving a yellow liquid. The crude material was purified by silica gel flash chromatography with n-heptane/ethyl acetate to give the 5,6,7,8-tetrahydroquinoline-3-carbonitrile as a white solid (433 mg, 53% yield). MS (ISP): m/z=159.1 [(M+H)$^+$].

b) 3-Cyano-5,6,7,8-tetrahydroquinoline 1-oxide

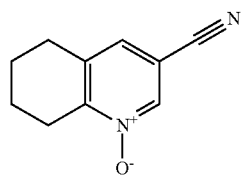 [SMILES: N#Cc1cc2c([n+]([O-])c1)CCCC2]

To a solution of 5,6,7,8-tetrahydroquinoline-3-carbonitrile (633 mg, 4.00 mmol) in acetic acid (5 ml) at 40° C. was portionwise added sodium perborate tetrahydrate (677 mg, 4.4 mmol) and the mixture was stirred at 40° C. for 16 hours. The acetic acid was removed by evaporation under reduced pressure, the residue was basified with aqueous saturated NaHCO$_3$ solution, the mixture extracted thrice with ethyl acetate, the combined extracts were dried over Na$_2$SO$_4$ and the solvent removed in vacuum to give the 3-cyano-5,6,7,8-tetrahydroquinoline 1-oxide (645 mg, 3.7 mmol, 92.5% yield) as a white solid. MS (ISP): m/z=175.1 [(M+H)$^+$].

c) 8-Hydroxy-5,6,7,8-tetrahydroquinoline-3-carbonitrile

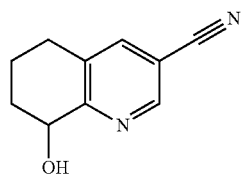 [SMILES: N#Cc1cnc2c(c1)CCCC2O]

To a solution of 3-cyano-5,6,7,8-tetrahydroquinoline 1-oxide (645 mg, 3.7 mmol) was added dropwise under ice cooling trifluoroacetic anhydride (6.22 g, 4.18 ml, 29.6 mmol). The light yellow solution was stirred at 23° C. for 18 h. The mixture was quenched with 1 N NaOH solution and stirred vigorously for 30 min., then extracted twice with dichloromethane, the combined organic layers were dried over Na$_2$SO$_4$, filtered and evaporated. The residue was purified by silica gel flash chromatography with n-heptane/ethyl acetate to give the 8-hydroxy-5,6,7,8-tetrahydroquinoline-3-carbonitrile (562 mg, 3.23 mmol, 87.1% yield) as a white solid. MS (ISP): m/z=175.1 [(M+H)$^+$].

d) 8-Oxo-5,6,7,8-tetrahydroquinoline-3-carbonitrile

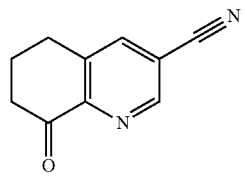 [SMILES: N#Cc1cnc2c(c1)CCCC2=O]

To a solution of 8-hydroxy-5,6,7,8-tetrahydroquinoline-3-carbonitrile (555 mg, 3.19 mmol) in DMSO (15 ml) at 23° C.

was added triethylamine (1.93 g, 2.66 ml, 19.1 mmol) and sulphur trioxide-pyridine complex (1.52 g, 9.56 mmol). The brown solution was stirred at 23° C. for 2 hours. The reaction mixture was poured on water and extracted twice with ethyl acetate. The combined organic layers were washed with brine, dried over Na$_2$SO$_4$, filtered and evaporated to give of a light brown solid, which was purified by silica gel flash chromatography with dichloromethane/methanol to give the 8-oxo-5,6,7,8-tetrahydroquinoline-3-carbonitrile (286 mg, 1.66 mmol, 52.1% yield) as a light yellow solid. MS (ISP): m/z=173.1 [(M+H)$^+$].

Intermediate A20F (5R)-5-(5-(6-chloro-2,3-dihydrobenzofuran-3-ylamino)-2-fluorophenyl)-6,6-difluoro-5,7,7-trimethyl-1,4-oxazepane-3-thione

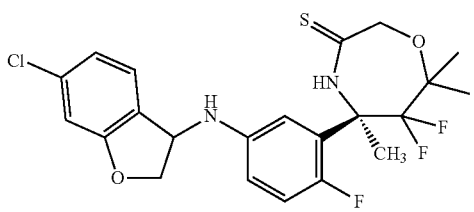 [SMILES: CC1(C)OCC(=S)N[C@](C)(c2cc(NC3COc4cc(Cl)ccc43)ccc2F)C1(F)F]

Prepared in an analogous manner as described for intermediate A22A from (R)-5-(5-amino-2-fluorophenyl)-6,6-difluoro-5,7,7-trimethyl-1,4-oxazepane-3-thione (intermediate A19B) (96 mg, 302 µmol) and commercially available 6-chlorobenzofuran-3(2H)-one [CAS no 3260-78-4] (61.0 mg, 362 µmol) The (5R)-5-(5-(6-chloro-2,3-dihydrobenzofuran-3-ylamino)-2-fluorophenyl)-6,6-difluoro-5,7,7-trimethyl-1,4-oxazepane-3-thione (72 mg, 153 µmol, 50.7% yield) was obtained as a light yellow foam. MS (ISN): m/z=469.1 [(M–H)$^-$] and 471.2 [(M+2-H)$^-$].

Intermediate A20G (R)-6,6-Difluoro-5-(2-fluoro-5-(4-fluorophenylamino)phenyl)-5,7,7-trimethyl-1,4-oxazepane-3-thione

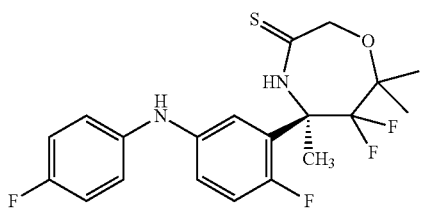 [SMILES: CC1(C)OCC(=S)N[C@](C)(c2cc(Nc3ccc(F)cc3)ccc2F)C1(F)F]

The compound was prepared in an analogous manner as described for intermediate A20A from (R)-6,6-difluoro-5-(2-fluoro-5-(4-fluorophenylamino)phenyl)-5,7,7-trimethyl-1,4-oxazepan-3-one (intermediate A22B) (157 mg, 396 µmol). The compound was obtained as a white solid (162 mg, 99%). MS (ISP): m/z=413.1 [(M+H)$^+$].

Intermediate A20H 7-(5-((R)-6,6-Difluoro-5,7,7-trimethyl-3-thioxo-1,4-oxazepan-5-yl)-2,4-difluorophenylamino)-6,7-dihydro-5H-cyclopenta[b]pyridine-3-carbonitrile

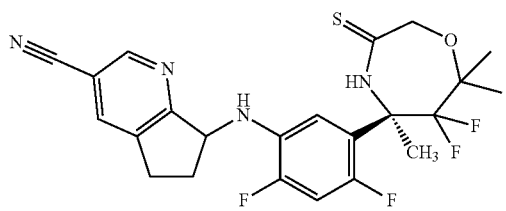 [SMILES: CC1(C)OCC(=S)N[C@](C)(c2cc(NC3CCc4cc(C#N)cnc43)c(F)cc2F)C1(F)F]

Prepared in an analogous manner as described for intermediate A22A from (R)-5-(5-amino-2,4-difluorophenyl)-6,6-difluoro-5,7,7-trimethyl-1,4-oxazepane-3-thione (intermediate A19C) (140 mg, 416 µmol) (305 mg, 958 µmol) and 7-oxo-6,7-dihydro-5H-[1]pyrindine-3-carbonitrile (72.4 mg, 458 µmol) The 7-(5-((R)-6,6-difluoro-5,7,7-trimethyl-3-thioxo-1,4-oxazepan-5-yl)-2,4-difluorophenylamino)-6,7-dihydro-5H-cyclopenta[b]pyridine-3-carbonitrile (162 mg, 81.3%) was obtained as a white foam. MS (ISP): m/z=479.0 [(M+H)$^+$].

Intermediate A20Ha (R)-7-(5-((R)-6,6-difluoro-5,7,7-trimethyl-3-thioxo-1,4-oxazepan-5-yl)-2,4-difluorophenylamino)-6,7-dihydro-5H-cyclopenta[b]pyridine-3-carbonitrile

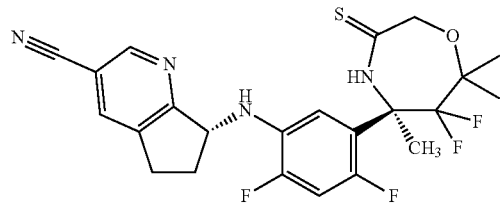 [SMILES: CC1(C)OCC(=S)N[C@](C)(c2cc(N[C@@H]3CCc4cc(C#N)cnc43)c(F)cc2F)C1(F)F]

Obtained from 7-(5-((R)-6,6-difluoro-5,7,7-trimethyl-3-thioxo-1,4-oxazepan-5-yl)-2,4-difluorophenylamino)-6,7-dihydro-5H-cyclopenta[b]pyridine-3-carbonitrile (intermediate A20H) (160 mg, 334 µmol) by chromatography on a Chiralpak AD column with 20% isopropanol in n-heptane being the less polar eluting epimer (A(–)) as a light brown foam (47 mg, 101 µmol, 30.3%). MS (ISP): m/z=479.0 [(M+H)$^+$].

Intermediate A20Hb (S)-7-(5-((R)-6,6-difluoro-5,7,7-trimethyl-3-thioxo-1,4-oxazepan-5-yl)-2,4-difluorophenylamino)-6,7-dihydro-5H-cyclopenta[b]pyridine-3-carbonitrile

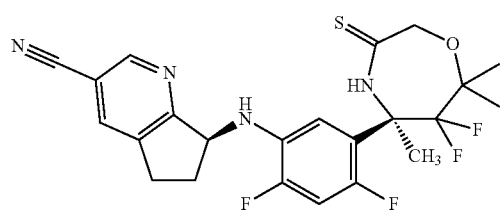 [SMILES: CC1(C)OCC(=S)N[C@](C)(c2cc(N[C@H]3CCc4cc(C#N)cnc43)c(F)cc2F)C1(F)F]

Obtained from 7-(5-((R)-6,6-difluoro-5,7,7-trimethyl-3-thioxo-1,4-oxazepan-5-yl)-2,4-difluorophenylamino)-6,7-dihydro-5H-cyclopenta[b]pyridine-3-carbonitrile (intermediate A20H) (160 mg, 334 μmol) by chromatography on a Chiralpak AD column with 20% isopropanol in n-heptane being the more polar eluting epimer (B(−)) as an off-white foam (56 mg, 117 μmol, 36.1%). MS (ISP): m/z=479.0 [(M+H)⁺].

Intermediate A20I (R)-5-(5-(6-Chloropyridin-3-ylamino)-2-fluorophenyl)-6,6-difluoro-5,7,7-trimethyl-1,4-oxazepane-3-thione

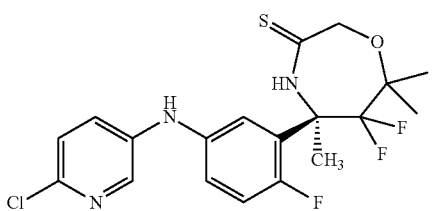 [SMILES: CC1(C)OCC(=S)N[C@](C)(c2cc(Nc3ccc(Cl)nc3)ccc2F)C1(F)F]

The compound was prepared in an analogous manner as described for intermediate A20A from (R)-5-(5-(6-chloropyridin-3-ylamino)-2-fluorophenyl)-6,6-difluoro-5,7,7-trimethyl-1,4-oxazepan-3-one (intermediate A22C) (63 mg, 152 μmol). The compound was obtained as a white solid (67 mg, 98%). MS (ISP): m/z=430.3 [(M+H)⁺] and 432.2 [(M+2+H)⁺].

Intermediate A20J (R)-6,6-Difluoro-5-(2-fluoro-5-(5-fluoropyridin-3-ylamino)phenyl)-5,7,7-trimethyl-1,4-oxazepane-3-thione

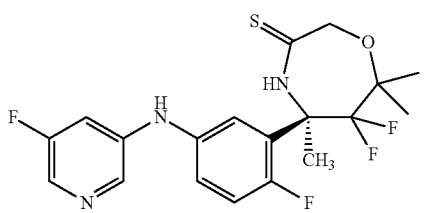 [SMILES: CC1(C)OCC(=S)N[C@](C)(c2cc(Nc3cncc(F)c3)ccc2F)C1(F)F]

The compound was prepared in an analogous manner as described for intermediate A20A from (R)-6,6-difluoro-5-(2-fluoro-5-(5-fluoropyridin-3-ylamino)phenyl)-5,7,7-trimethyl-1,4-oxazepan-3-one (intermediate A22D) (52 mg, 131 μmol). The compound was obtained as a white solid (34 mg, 63%). MS (ISP): m/z=414.2 [(M+H)⁺].

Intermediate A20K (R)-6,6-Difluoro-5-(2-fluoro-5-(pyridin-3-ylamino)phenyl)-5,7,7-trimethyl-1,4-oxazepane-3-thione

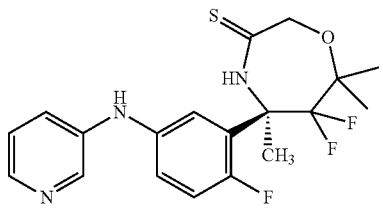 [SMILES: CC1(C)OCC(=S)N[C@](C)(c2cc(Nc3cccnc3)ccc2F)C1(F)F]

The compound was prepared in an analogous manner as described for intermediate A20A from (R)-6,6-difluoro-5-(2-fluoro-5-(pyridin-3-ylamino)phenyl)-5,7,7-trimethyl-1,4-oxazepan-3-one (intermediate A22E) (54 mg, 142 μmol). The compound was obtained as a white solid (43 mg, 76%). MS (ISP): m/z=396.2 [(M+H)⁺].

Intermediate A20L (R)-6,6-Difluoro-5-(2-fluoro-5-(6-methoxypyridin-3-ylamino)phenyl)-5,7,7-trimethyl-1,4-oxazepane-3-thione

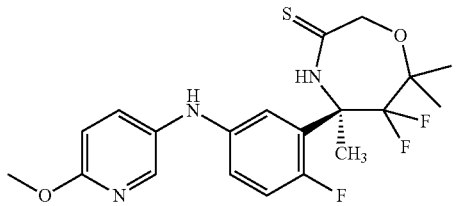

The compound was prepared in an analogous manner as described for intermediate A20A from (R)-6,6-difluoro-5-(2-fluoro-5-(6-methoxypyridin-3-ylamino)phenyl)-5,7,7-trimethyl-1,4-oxazepan-3-one (intermediate A22F) (32 mg, 78 μmol). The compound was obtained as a light green foam (28 mg, 84%). MS (ISP): m/z=426.2 [(M+H)⁺].

Intermediate A20M (R)-6,6-Difluoro-5-(2-fluoro-5-(5-(trifluoromethyl)pyridin-3-ylamino)phenyl)-5,7,7-trimethyl-1,4-oxazepane-3-thione

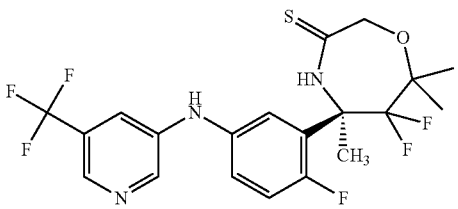 [SMILES: CC1(C)OCC(=S)N[C@](C)(c2cc(Nc3cncc(C(F)(F)F)c3)ccc2F)C1(F)F]

The compound was prepared in an analogous manner as described for intermediate A20A from (R)-6,6-difluoro-5-(2-fluoro-5-(5-(trifluoromethyl)pyridin-3-ylamino)phenyl)-5,7,7-trimethyl-1,4-oxazepan-3-one (intermediate A22G) (123 mg, 275 μmol). The compound was obtained as white foam (88 mg, 69%). MS (ISP): m/z=464.1 [(M+H)⁺].

Intermediate A20N (R)-6,6-Difluoro-5-(2-fluoro-5-(6-methylpyridin-3-ylamino)phenyl)-5,7,7-trimethyl-1,4-oxazepane-3-thione

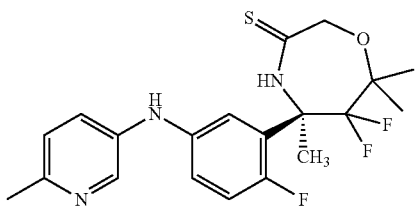

The compound was prepared in an analogous manner as described for intermediate A20A from (R)-6,6-difluoro-5-(2-fluoro-5-(6-methylpyridin-3-ylamino)phenyl)-5,7,7-trimethyl-1,4-oxazepan-3-one (intermediate A22H) (14 mg, 36 µmol). The compound was obtained as an off-white foam (8 mg, 55%). MS (ISP): m/z=410.2 [(M+H)$^+$].

Intermediate A21A (R)-5-(5-Amino-2-fluorophenyl)-6,6-difluoro-5-methyl-1,4-oxazepan-3-one

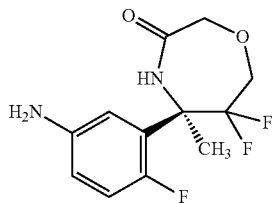 [SMILES: C[C@]1(c2cc(N)ccc2F)NC(=O)COCC1(F)F]

To a solution of (R)-5-[5-(benzhydrylidene-amino)-2-fluoro-phenyl]-6,6-difluoro-5-methyl-[1,4]oxazepan-3-one (intermediate A17D) (308 mg, 0.70 mmol) in dioxane (20 ml) at 23° C. was added 1 M HCl (2.1 ml, 2.1 mmol) was added. After 30 min of stirring, the reaction mixture was poured on sat. NaHCO$_3$-solution and extracted twice with ethyl acetate. The combined organic layers were washed with brine, dried over sodium sulfate, filtered and evaporated to give a dark green oil, which was purified by silica gel column chromatography with n-heptane/ethyl acetate to give the (R)-5-(5-amino-2-fluorophenyl)-6,6-difluoro-5-methyl-1,4-oxazepan-3-one (172 mg, 0.63 mmol, 90%) as a yellow foam. MS (ISP): m/z=275.2 [(M+H)$^+$].

Intermediate A22A (5R)-5-(5-(3-Chloro-6,7-dihydro-5H-cyclopenta[b]pyridin-7-ylamino)-2-fluorophenyl)-6,6-difluoro-5-methyl-1,4-oxazepan-3-one

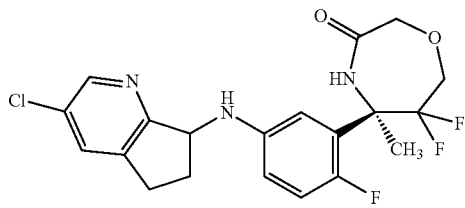 [SMILES: C[C@]1(c2cc(NC3CCc4cc(Cl)cnc43)ccc2F)NC(=O)COCC1(F)F]

To a solution of 3-chloro-5,6-dihydro-[1]pyrindin-7-one (28 mg, 167 µmol) in methanol (6 ml) and dichloromethane (750 µl) at 23° C. was added (R)-5-(5-amino-2-fluorophenyl)-6,6-difluoro-5-methyl-1,4-oxazepan-3-one (intermediate A21A) (49.9 mg, 182 µmol) followed by decaborane (5.6 mg, 167 µmol) and the mixture was stirred at 23° C. for 22 hours. After completion, the mixture was poured into aqueous NaHCO$_3$ solution, extracted with ethyl acetate, the organic layers were dried over Na$_2$SO$_4$ and the solvent evaporated. The crude material was purified by silica gel flash chromatography with n-heptane/ethyl acetate to give the (5R)-5-(5-(3-chloro-6,7-dihydro-5H-cyclopenta[b]pyridin-7-ylamino)-2-fluorophenyl)-6,6-difluoro-5-methyl-1,4-oxazepan-3-one (62 mg, 87%) as an orange solid. MS (ISP): m/z=426.1 [(M+H)$^+$] and 428.1 [(M+2+H)$^+$].

The 3-chloro-5,6-dihydro-[1]pyrindin-7-one was prepared as follows:

a) 3-Chloro-6,7-dihydro-5H-[1]pyridine

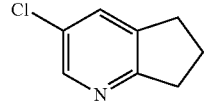

A solution of 5-chloro-2-(pent-4-ynyl)pyrimidine (H. C. van der Plas, Tetrahedron 1989, 45, 5151-5162) (4.95 g (27.4 mmol) in nitrobenzene (50 ml) was heated to 210° C. for 1.5 hours under a continuous stream of nitrogen. The reaction was followed by TLC (silica gel, heptane:ethyl acetate=2:1; UV detection 254 nm). After completion, the reaction mixture was purified by flash chromatography on silica gel using a gradient of heptane/ethyl acetate=100:0 to 80:20 as the eluent. The 3-chloro-6,7-dihydro-5H-[1]pyridine was obtained as a light brown solid (3.21 g, 76%); (calculated) C$_8$H$_8$ClN [153.61]; (found) [M+H]$^+$=154.

b) 3-Chloro-6,7-dihydro-5H-[1]piridina 1-oxide

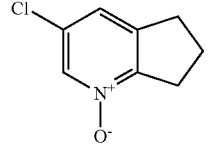 [SMILES: [O-][n+]1cc(Cl)cc2c1CCC2]

A solution of 3-chloro-6,7-dihydro-5H-[1]pyridine (3.03 g, 19.7 mmol) in acetic acid (19.7 ml) was treated at room temperature with hydrogen peroxide (3.45 ml, 39.5 mmol). The mixture was heated to 70° C. and stirred at this temperature overnight. After completion, the reaction mixture was allowed to cool and was concentrated at reduced pressure. Water was added and the mixture was evaporated again. This procedure was repeated another 2 times. The residue was dissolved in ethyl acetate, washed with a saturated aqueous solution of sodium hydrogen carbonate and brine, then dried over sodium sulfate and evaporated at reduced pressure. The crude 3-chloro-6,7-dihydro-5H-[1]pyridine 1-oxide was obtained as dark green crystals (2.07 g, 62%). (calculated) C$_8$H$_8$ClNO [169.61]; (found) [M+H]$^+$=170.

c) Acetic acid 3-chloro-6,7-dihydro-5H-[1]pyrindin-7-yl ester

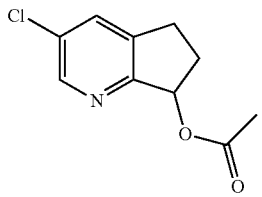

A solution of 3-chloro-6,7-dihydro-5H-[1]pyrindine 1-oxide (2.07 g, 12.2 mmol) in acetic acid anhydride (62.2 ml, 659 mmol) was stirred at 110° C. for 20 hours. For the workup, the solvent was removed at reduced pressure and the residue quenched with saturated aqueous solution of sodium hydrogen carbonate. The aqueous phase was extracted with dichloromethane, the resulting organic layers combined and dried over sodium sulfate. After evaporation of the solvent, the residue was purified by flash chromatography on silica gel using a gradient of heptane/ethyl acetate=100:0 to 70:30 as the eluent. The acetic acid 3-chloro-6,7-dihydro-5H-[1]pyrindin-7-yl ester was obtained as a red liquid (1.57 g, 61%); (calculated) $C_{10}H_{10}ClNO_2$ [211.65]; (found) $[M+H]^+$=212.

d) 3-Chloro-6,7-dihydro-5H-[1]pyrindin-7-ol

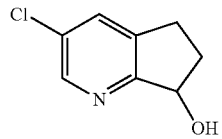 [SMILES: OC1CCc2cc(Cl)cnc21]

A solution of acetic acid 3-chloro-6,7-dihydro-5H-[1]pyrindin-7-yl ester (1.57 g, 7.42 mmol) in methanol (35.7 ml) was treated with 1 M sodium hydroxide solution (8.9 ml). The mixture was stirred at room temperature for 1.5 hours. The reaction was followed by TLC (silica gel, heptane:ethyl acetate=1:1; UV detection 254 nm). After completion, the reaction mixture was treated with water and extracted with dichloromethane. The combined organic layers were dried over sodium sulfate, then evaporated leaving a dark red liquid (1.15 g, 91%) which crystallized on standing. Following NMR the product was pure enough for the next step of the synthesis; (calculated) $C_8H_8ClNO$ [169.61]; (found) $[M+H]^+$=170.

e) 3-Chloro-5,6-dihydro-[1]pyrindin-7-one

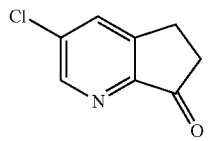 [SMILES: O=C1CCc2cc(Cl)cnc21]

A solution of 3-chloro-6,7-dihydro-5H-[1]pyrindin-7-ol (570 mg, 3.36 mmol) in dimethylsulphoxide (17.7 ml) was treated at room temperature with triethylamine (2.81 ml, 20.2 mmol) followed by sulfur trioxide-pyridine complex (1.6 g, 10.1 mmol). The solution was stirred at room temperature for 1 hour. After completion, the reaction mixture was treated with water and extracted with dichloromethane. The combined organic layers were dried over sodium sulfate, then evaporated leaving a dark red liquid. The crude material was purified by flash chromatography on silica gel using a gradient of heptane/ethyl acetate=70:30 to 30:70 as the eluent. The 3-chloro-5,6-dihydro-[1]pyrindin-7-one was obtained as a pink solid (472 mg, 84%); (calculated) $C_8H_6ClNO$ [167.60]; (found) $[M+H]^+$=168.

Intermediate A22B (R)-6,6-Difluoro-5-(2-fluoro-5-(4-fluorophenylamino)phenyl)-5,7,7-trimethyl-1,4-oxazepan-3-one

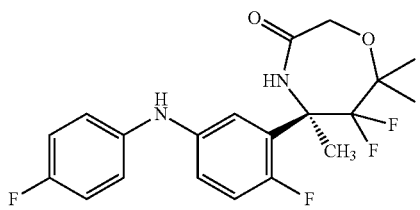 [SMILES: CC1(C)OCC(=O)N[C@](C)(c2cc(Nc3ccc(F)cc3)ccc2F)C1(F)F]

Prepared in an analogous manner as described for intermediate A9A or A13A from (R)-545-bromo-2-fluorophenyl)-6,6-difluoro-5,7,7-trimethyl-1,4-oxazepan-3-one (intermediate A16B) (300 mg, 819 μmol) and commercially available 4-fluoroaniline [CAS no 371-40-4] 4-fluoroaniline (157 μL, 1.64 mmol). The (R)-6,6-difluoro-5-(2-fluoro-5-(4-fluorophenylamino)phenyl)-5,7,7-trimethyl-1,4-oxazepan-3-one (181 mg, 55.7%) was obtained as a light yellow foam. MS (ISP): m/z=397.0 $[(M+H)^+]$.

Intermediate A22C (R)-5-(5-(6-Chloropyridin-3-ylamino)-2-fluorophenyl)-6,6-difluoro-5,7,7-trimethyl-1,4-oxazepan-3-one

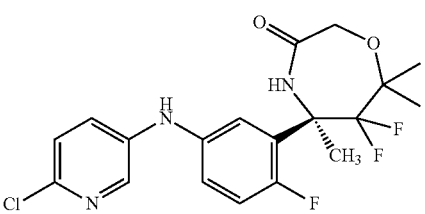 [SMILES: CC1(C)OCC(=O)N[C@](C)(c2cc(Nc3ccc(Cl)nc3)ccc2F)C1(F)F]

Prepared in an analogous manner as described for intermediate A9A or A13A from (R)-5-(5-bromo-2-fluorophenyl)-6,6-difluoro-5,7,7-trimethyl-1,4-oxazepan-3-one (intermediate A16B) (200 mg, 546 μmol) and commercially available 5-amino-2-chloropyridine [CAS no 5350-93-6] (140 mg, 1.09 mmol). The (R)-5-(5-(6-chloropyridin-3-ylamino)-2-fluorophenyl)-6,6-difluoro-5,7,7-trimethyl-1,4-oxazepan-3-one (74 mg, 32.7%) was obtained as a light brown foam. MS (ISP): m/z=414.2 $[(M+H)^+]$ and 416.2 $[(M+2+H)^+]$.

Intermediate A22D (R)-6,6-Difluoro-5-(2-fluoro-5-(5-fluoropyridin-3-ylamino)phenyl)-5,7,7-trimethyl-1,4-oxazepan-3-one

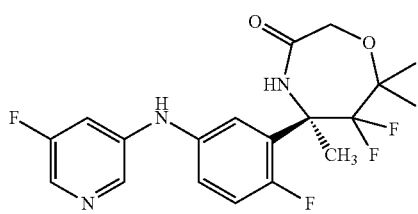 [SMILES: CC1(C)OCC(=O)N[C@](C)(c2cc(Nc3cncc(F)c3)ccc2F)C1(F)F]

Prepared in an analogous manner as described for intermediate A9A or A13A from (R)-5-(5-bromo-2-fluorophenyl)-6,6-difluoro-5,7,7-trimethyl-1,4-oxazepan-3-one (intermediate A16B) (200 mg, 546 µmol) and commercially available 3-amino-5-fluoropyridine [CAS no 210169-05-4] (122 mg, 1.09 mmol). The (R)-6,6-difluoro-5-(2-fluoro-5-(5-fluoropyridin-3-ylamino)phenyl)-5,7,7-trimethyl-1,4-oxazepan-3-one (56 mg, 26%) was obtained as an off-white foam. MS (ISP): m/z=398.2 [(M+H)$^+$].

Intermediate A22E (R)-6,6-Difluoro-5-(2-fluoro-5-(pyridin-3-ylamino)phenyl)-5,7,7-trimethyl-1,4-oxazepan-3-one

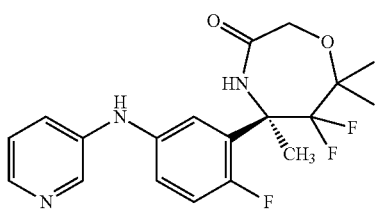 [SMILES: CC1(C)OCC(=O)N[C@](C)(c2cc(Nc3cccnc3)ccc2F)C1(F)F]

Prepared in an analogous manner as described for intermediate A9A or A13A from (R)-5-(5-bromo-2-fluorophenyl)-6,6-difluoro-5,7,7-trimethyl-1,4-oxazepan-3-one (intermediate A16B) (200 mg, 546 µmol) and commercially available 3-aminopyridine [CAS no 462-08-8] (103 mg, 1.09 mmol). The (R)-6,6-difluoro-5-(2-fluoro-5-(pyridin-3-ylamino)phenyl)-5,7,7-trimethyl-1,4-oxazepan-3-one (60 mg, 29%) was obtained as an off-white foam. MS (ISP): m/z=380.3 [(M+H)$^+$].

Intermediate A22F (R)-6,6-Difluoro-5-(2-fluoro-5-(6-methoxypyridin-3-ylamino)phenyl)-5,7,7-trimethyl-1,4-oxazepan-3-one

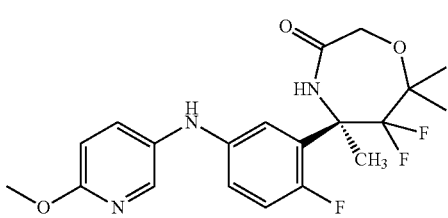

Prepared in an analogous manner as described for intermediate A9A or A13A from (R)-5-(5-bromo-2-fluorophenyl)-6,6-difluoro-5,7,7-trimethyl-1,4-oxazepan-3-one (intermediate A16B) (200 mg, 546 µmol) and commercially available 5-amino-2-methoxypyridine [CAS no 6628-77-9] (136 mg, 1.09 mmol). The (R)-6,6-difluoro-5-(2-fluoro-5-(6-methoxypyridin-3-ylamino)phenyl)-5,7,7-trimethyl-1,4-oxazepan-3-one (32 mg, 14%) was obtained as a brown solid. MS (ISP): m/z=410.2 [(M+H)$^+$].

Intermediate A22G (R)-6,6-Difluoro-5-(2-fluoro-5-(5-(trifluoromethyl)pyridin-3-ylamino)phenyl)-5,7,7-trimethyl-1,4-oxazepan-3-one

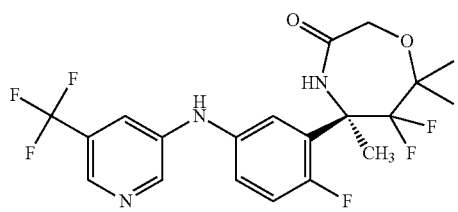 [SMILES: CC1(C)OCC(=O)N[C@](C)(c2cc(Nc3cncc(C(F)(F)F)c3)ccc2F)C1(F)F]

Prepared in an analogous manner as described for intermediate A9A or A13A from (R)-5-(5-bromo-2-fluorophenyl)-6,6-difluoro-5,7,7-trimethyl-1,4-oxazepan-3-one (intermediate A16B) (200 mg, 546 µmol) and commercially available 5-(trifluoromethyl)-3-aminopyridine [CAS no 112110-07-3] (177 mg, 1.09 mmol). The (R)-6,6-difluoro-5-(2-fluoro-5-(5-(trifluoromethyl)pyridin-3-ylamino)phenyl)-5,7,7-trimethyl-1,4-oxazepan-3-one (142 mg, 58%) was obtained as an off-white foam. MS (ISP): m/z=448.1 [(M+H)$^+$].

Intermediate A22H (R)-6,6-Difluoro-5-(2-fluoro-5-(6-methylpyridin-3-ylamino)phenyl)-5,7,7-trimethyl-1,4-oxazepan-3-one

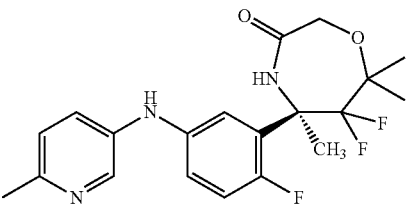

Prepared in an analogous manner as described for intermediate A9A or A13A from (R)-5-(5-bromo-2-fluorophenyl)-6,6-difluoro-5,7,7-trimethyl-1,4-oxazepan-3-one (intermediate A16B) (200 mg, 546 µmol) and commercially available 3-amino-6-methylpyridine [CAS no 3430-14-6] (118 mg, 1.09 mmol). The (R)-6,6-difluoro-5-(2-fluoro-5-(6-methylpyridin-3-ylamino)phenyl)-5,7,7-trimethyl-1,4-oxazepan-3-one (15 mg, 7.0%) was obtained as a light brown foam. MS (ISP): m/z=394.1 [(M+H)$^+$].

Synthesis of the O-allyl Compounds A23 from the Alcohols A4

General Procedure

To a solution of the alcohol A4 (29.25 mmol) in dry tetrahydrofuran (290 mL) at 23° C. was added commercially available allyl tert-butyl carbonate (5.56 g, 35.1 mmol), argon was bubbled through the solution and tetrakistriphenylphosphinepalladium(0) (1.02 g, 878 µmol) was added and the mixture was stirred at 70° C. for 8 hours. Cooled to 23° C., extracted with ethyl acetate and water, dried the organic layer over $Na_2SO_4$, filtered and evaporated totally. The residue was chromatographed on silica gel with ethyl acetate 0%-80% in heptane to give the O-allylated compounds A23.

Intermediate A23A (R)—N—((R)-4-(allyloxy)-2-(5-bromo-2-fluorophenyl)-3,3-difluoro-4-methylpentan-2-yl)-2-methylpropane-2-sulfinamide

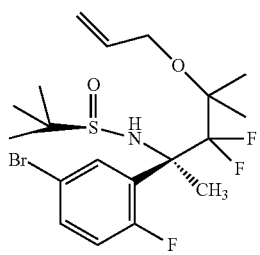 [SMILES: C=CCOC(C)(C)C(F)(F)[C@](C)(N[S@](=O)C(C)(C)C)c1cc(Br)ccc1F]

The compound was prepared from (R)—N—((R)-2-(5-bromo-2-fluorophenyl)-3,3-difluoro-4-hydroxy-4-methylpentan-2-yl)-2-methylpropane-2-sulfinamide (intermediate A4F) (12.58 g; 29.25 mmol). The (R)—N—((R)-4-(allyloxy)-2-(5-bromo-2-fluorophenyl)-3,3-difluoro-4-methylpentan-2-yl)-2-methylpropane-2-sulfinamide (9.5 g, 20.2 mmol, 69% yield) was obtained as a light yellow solid. MS (ISP): m/z=470.0 [(M+H)$^+$] and 472.0 [(M+2+H)$^+$].

Intermediate A23B (R)—N—((R)-4-(allyloxy)-2-(5-bromo-2,4-difluorophenyl)-3,3-difluoro-4-methylpentan-2-yl)-2-methylpropane-2-sulfinamide

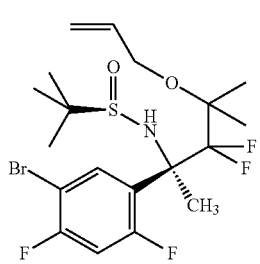 [SMILES: C=CCOC(C)(C)C(F)(F)[C@](C)(N[S@](=O)C(C)(C)C)c1cc(Br)c(F)cc1F]

The compound was prepared from (R)—N—((R)-2-(5-bromo-2,4-difluorophenyl)-3,3-difluoro-4-hydroxy-4-methylpentan-2-yl)-2-methylpropane-2-sulfinamide (intermediate A4G) (21.4 g; 47.7 mmol). The (R)—N—((R)-4-(allyloxy)-2-(5-bromo-2,4-difluorophenyl)-3,3-difluoro-4-methylpentan-2-yl)-2-methylpropane-2-sulfinamide (16.15 g, 33.1 mmol, 69% yield) was obtained as a light brown oil. MS (ISP): m/z=488.1 [(M+H)$^+$] and 490.0 [(M+2+H)$^+$].

Synthesis of the Acids A24 from the Allyl Ethers A24

General Procedure

To a solution of the allyl ether A23 (20.2 mmol) in ethyl acetate (95 mL), acetonitrile (95 mL) and water (142 mL) at 23° C. was added sodium periodate (28.1 g, 131 mmol) followed by ruthenium(III) chloride hydrate (91 mg, 0.4 mmol) and the mixture was stirred at 23° C. for 3 hours. Diluted with ethyl acetate and extracted with 1 N HCl+ diluted $NaHSO_3$-sol., dried the organic layer over $Na_2SO_4$, filtered off, evaporated totally and dried in high vacuum to give the crude product (acid A25), which was used without further purification.

Intermediate A24A (R)-2-(4-(5-bromo-2-fluorophenyl)-4-(1,1-dimethylethylsulfonamido)-3,3-difluoro-2-methylpentan-2-yloxy)acetic acid

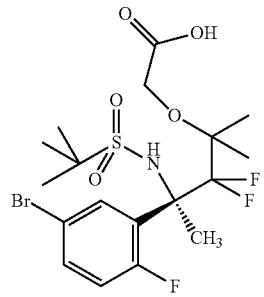 [SMILES: CC(C)(OCC(=O)O)C(F)(F)[C@](C)(NS(=O)(=O)C(C)(C)C)c1cc(Br)ccc1F]

The compound was prepared from (R)—N—((R)-4-(allyloxy)-2-(5-bromo-2-fluorophenyl)-3,3-difluoro-4-methylpentan-2-yl)-2-methylpropane-2-sulfinamide (intermediate A23A) (9.5 g; 20.2 mmol). The (R)-2-(4-(5-bromo-2-fluorophenyl)-4-(1,1-dimethylethylsulfonamido)-3,3-difluoro-2-methylpentan-2-yloxy)acetic acid (10.2 g, 20.2 mmol, 100% yield) was obtained as a light yellow foam. MS (ISN): m/z=502.0 [(M−H)$^-$] and 503.9 [(M+2−H)$^-$].

Intermediate A24B (R)-2-(4-(5-bromo-2,4-difluorophenyl)-4-(1,1-dimethylethylsulfonamido)-3,3-difluoro-2-methylpentan-2-yloxy)acetic acid

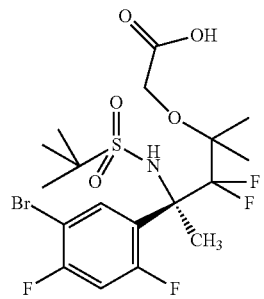 [SMILES: CC(C)(OCC(=O)O)C(F)(F)[C@](C)(NS(=O)(=O)C(C)(C)C)c1cc(Br)c(F)cc1F]

The compound was prepared from (R)—N—((R)-4-(allyloxy)-2-(5-bromo-2,4-difluorophenyl)-3,3-difluoro-4-methylpentan-2-yl)-2-methylpropane-2-sulfinamide (intermediate A23B) (16.14 g; 33 mmol). The (R)-2-(4-(5-bromo-2,4-difluorophenyl)-4-(1,1-dimethylethylsulfonamido)-3,3- difluoro-2-methylpentan-2-yloxy)acetic acid (17.3 g, 33.1 mmol, 100% yield) was obtained as a light grey solid. MS (ISN): m/z=520.0 [(M−H)⁻] and 521.9 [(M+2−H)⁻].

Synthesis of the Ethyl Esters A25 from the Acids A24

General Procedure

To a solution of the acid A24 (18.2 mmol) in ethanol (200 mL) at 23° C. was dropwise added thionyl chloride (5.3 mL, 72.8 mmol) and the mixture was stirred at reflux for 18 hours. Cooled to 23° C., diluted with ethyl acetate and extracted with sat NaHCO₃-sol. and brine, dried over Na₂SO₄, filtered off and evaporated totally to give the crude ethyl esters A25, which were used without further purification.

Intermediate A25A (R)-ethyl 2-(4-(5-bromo-2-fluorophenyl)-4-(1,1-dimethylethylsulfonamido)-3,3-difluoro-2-methyl-pentan-2-yloxy)acetate

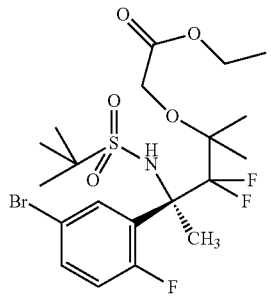 [SMILES: CCOC(=O)COC(C)(C)C(F)(F)[C@](C)(NS(=O)(=O)C(C)(C)C)c1cc(Br)ccc1F]

The compound was prepared from (R)-2-(4-(5-bromo-2-fluorophenyl)-4-(1,1-dimethylethylsulfonamido)-3,3-difluoro-2-methylpentan-2-yloxy)acetic acid (intermediate A24A) (10.2 g; 18.2 mmol). The (R)-ethyl 2-(4-(5-bromo-2-fluorophenyl)-4-(1,1-dimethylethylsulfonamido)-3,3-difluoro-2-methylpentan-2-yloxy)acetate (10 g, 103% yield) was obtained as a light brown solid. MS (ISN): m/z=530.2 [(M−H)⁻] and 532.0 [(M+2−H)⁻].

Intermediate A25B (R)-ethyl 2-(4-(5-bromo-2,4-difluorophenyl)-4-(1,1-dimethylethylsulfonamido)-3,3-difluoro-2-methyl-pentan-2-yloxy)acetate

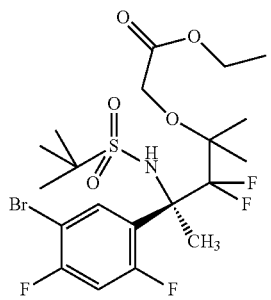 [SMILES: CCOC(=O)COC(C)(C)C(F)(F)[C@](C)(NS(=O)(=O)C(C)(C)C)c1cc(Br)c(F)cc1F]

The compound was prepared from (R)-2-(4-(5-bromo-2,4-difluorophenyl)-4-(1,1-dimethylethylsulfonamido)-3,3-difluoro-2-methylpentan-2-yloxy)acetic acid (intermediate A24B) (17.1 g; 33 mmol). The (R)-ethyl 2-(4-(5-bromo-2,4-difluorophenyl)-4-(1,1-dimethylethylsulfonamido)-3,3-difluoro-2-methylpentan-2-yloxy)acetate (20.55 g, 37.3 mmol, 113% yield) was obtained as a light brown oil. MS (ISP): m/z=550.2 [(M+H)⁺] and 552.3 [(M+2+H)⁺].

Synthesis of the Amino Esters A26 from the Sulfonamides A25

General Procedure

To a solution of the sulfonamide A25 (18.8 mmol) in dichloromethane (190 mL) at 0° C. was dropwise added a 0.25 M solution of trifluoromethanesulfonic acid (225 mL, 56.3 mmol) and the mixture was stirred at 23° C. for 30 min. Poured into sat NaHCO₃-sol., extracted with dichloromethane, dried the organic layer over Na₂SO₄, filtered off and evaporated totally to give the crude amino esters A26, which were used without further purification or alternatively purified by silica gel column chromatography with heptane and ethyl acetate.

Intermediate A26A (R)-ethyl 2-(4-amino-4-(5-bromo-2-fluorophenyl)-3,3-difluoro-2-methylpentan-2-yloxy)acetate

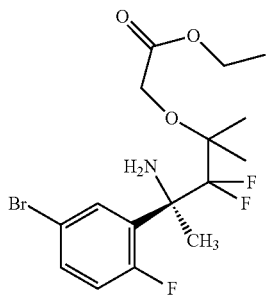 [SMILES: CCOC(=O)COC(C)(C)C(F)(F)[C@](C)(N)c1cc(Br)ccc1F]

The compound was prepared from (R)-ethyl 2-(4-(5-bromo-2-fluorophenyl)-4-(1,1-dimethylethylsulfonamido)-3,3-difluoro-2-methylpentan-2-yloxy)acetate (intermediate A25A) (10.2 g; 18.2 mmol). The (R)-ethyl 2-(4-amino-4-(5-bromo-2-fluorophenyl)-3,3-difluoro-2-methylpentan-2-yloxy)acetate (6.85 g, 16.6 mmol, 88.5% yield) was obtained as a light yellow oil. MS (ISP): m/z=412.1 [(M+H)⁺] and 414.2 [(M+2+H)⁺].

Intermediate A26B (R)-ethyl 2-(4-amino-4-(5-bromo-2,4-difluorophenyl)-3,3-difluoro-2-methylpentan-2-yloxy)acetate

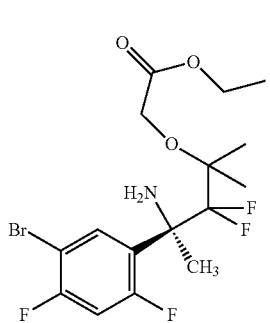 [SMILES: CCOC(=O)COC(C)(C)C(F)(F)[C@](C)(N)c1cc(Br)c(F)cc1F]

The compound was prepared from (R)-ethyl 2-(4-(5-bromo-2,4-difluorophenyl)-4-(1,1-dimethylethylsulfonamido)-3,3-difluoro-2-methylpentan-2-yloxy)acetate (intermediate A25B) (20.55 g; 37.3 mmol). The (R)-ethyl 2-(4- amino-4-(5-bromo-2,4-difluorophenyl)-3,3-difluoro-2-methylpentan-2-yloxy)acetate (16.1 g, 37.4 mmol, 100% yield) was obtained as a light yellow oil. MS (ISP): m/z=430.1 [(M+H)$^+$] and 432.2 [(M+2+H)$^+$].

Example 1

[3-((5R,6R)-3-Amino-6-fluoro-5-methyl-2,5,6,7-tetrahydro-[1,4]oxazepin-5-yl)-4-fluoro-phenyl]-(3-chloro-6,7-dihydro-5H-[1]pyrindin-7-yl)-amine To a solution of (5R,6R)-5-(5-amino-2-fluoro-phenyl)-6-fluoro-5-methyl-2,5,6,7-tetrahydro-1,4-oxazepin-3-ylamine (intermediate A10B) (20 mg, 78.4 µmol) in 1,2-dichloroethane (200 µl) was added at 23° C. under inert atmosphere 3-chloro-5,6-dihydro-[1]pyrindin-7-one (14.4 mg, 86.2 µmol) and acetic acid (9.41 mg, 8.97 µl, 157 µmol) and the solution was stirred at 23° C. for 30 min. Then sodium triacetoxyborohydride (24.9 mg, 118 µmol) was added and the mixture was stirred at 23° C. for 4 h. After addition of 1 M HCl (1 ml) and stirring for 10 min, the aqueous layer was washed once with dichloromethane, then treated with sat. Na$_2$CO$_3$-sol. to achieve pH 14 and extracted twice with ethyl acetate. The combined organic layers were dried over Na$_2$SO$_4$ and evaporated to give a crude product, which was purified by basic preparative HPLC to give (5R,6R)-5-(5-(3-chloro-6,7-dihydro-5H-cyclopenta[b]pyridin-7-ylamino)-2-fluorophenyl)-6-fluoro-5-methyl-2,5,6,7-tetrahydro-1,4-oxazepin-3-amine (11 mg, 27.0 µmol, 34.5% yield) as a colorless oil. MS (ISP): m/z=407.3.3 [(M+H)$^+$] and 409.3 [(M+2+H)$^+$].

Example 2

(5R,6R)-5-{5-[(4-Chloro-1-difluoromethyl-1H-pyrazol-3-ylmethyl)-amino]-2-fluoro-phenyl}-6-fluoro-5-methyl-2,5,6,7-tetrahydro-[1,4]oxazepin-3-ylamine To a solution of (5R,6R)-5-(5-amino-2-fluoro-phenyl)-6-fluoro-5-methyl-2,5,6,7-tetrahydro-1,4-oxazepin-3-ylamine (intermediate A10B) (20.4 mg, 80 µmol) in methanol (0.3 ml) was added at 23° C. under inert atmosphere 4-chloro-1-difluoromethyl-1H-pyrazole-3-carbaldehyde (15.9 mg, 88 µmol) and the reaction mixture was stirred at 23° C. for 60 min. Then decaborane (19.5 mg, 160 µmol) was added in one portion and the mixture was stirred at 45° C. for 15 h. The solution was quenched with 10% Na$_2$CO$_3$-sol., methanol was removed under reduced pressure and then extracted three times with ethyl acetate. The organic layers were dried with Na$_2$SO$_4$ and evaporated to give the crude product, which was purified by basic preparative HPLC (column: Gemini 5µ C18 110A° AXIA (50×21.2 mm), flow: 40 ml/min; gradient: water (+0.1% TEA)/acetonitrile (90%-10% 1 min plateau; in 4.5 min to 5%-95%); collection: UV-detector 230 nm) and further purified by preparative TLC (Merck Si—NH2 HPTLC-plate with dichloromethane/methanol 9:1) to give the (5R,6R)-5-(5-((4-chloro-1-(difluoromethyl)-1H-pyrazol-3-yl)methylamino)-2-fluorophenyl)-6-fluoro-5-methyl-2,5,6,7-tetrahydro-1,4-oxazepin-3-amine (1.5 mg, 4.5%) as a colorless oil. MS (ISP): m/z=420.1 [(M+H)$^+$] and 422.1 [(M+2+H)$^+$].

The 4-chloro-1-difluoromethyl-1H-pyrazole-3-carbaldehyde was prepared as follows:

a) 1-Difluoromethyl-1H-pyrazole-3-carboxylic acid methyl ester

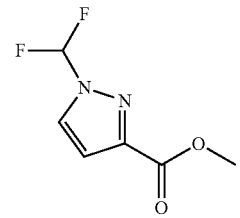

A solution of 1-difluoromethyl-1H-pyrazole-3-carboxylic acid (CAS [925179-02-8]) (500 mg, 3.1 mmole) in methanol (18 ml) was cooled to 0° C. and treated with sulfuric acid (98%, 0.2 ml, 3.1 mmol). The mixture was heated to reflux for 2 hours, cooled to 23° C. and concentrated at reduced pressure. The residue was partitioned between AcOEt and water, the organic layer was washed with water until the water phase showed a neutral pH, dried and evaporated to give the title compound (535 mg) as a colorless liquid which was used without further purification. MS: m/z=177.1 [M+H]$^+$.

b) 4-Chloro-1-difluoromethyl-1H-pyrazole-3-carboxylic acid methyl ester

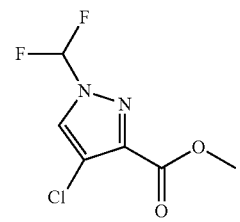

A mixture of 1-difluoromethyl-1H-pyrazole-3-carboxylic acid methyl ester (535 mg, 3 mmole) and N-chloro-succinimide (1.22 g, 9.1 mmole) in DMF (5 ml) was heated at 50° C. overnight. The reaction mixture was cooled, partitioned between AcOEt and water, the organic layer was washed with water, dried, evaporated and the residue was purified by chromatography on silica gel using cyclohexane/AcOEt (3:1) to give the title compound (540 mg) as a white solid. MS: m/z=209.9 [M]$^+$.

c) 4-Chloro-1-difluoromethyl-1H-pyrazole-3-carboxylic acid

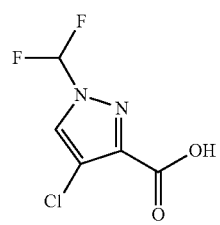

A solution of 4-chloro-1-difluoromethyl-1H-pyrazole-3-carboxylic acid methyl ester (540 mg, 2.6 mmole) in THF (18 ml) was treated at 23° C. with a solution of lithium hydroxide (135 mg, 5.6 mmole) in a 1:1-mixture of water and methanol

95

(12 ml). After 1 hour the reaction was complete, and the solvents were evaporated at reduced pressure. The residue was partitioned between 2 M aqueous HCl and AcOEt, the organic layer was dried, evaporated, the residue was triturated with pentane and the solid was dried to give the title compound (477 mg) as a white solid. MS: m/z=195.0 [M–H]$^-$.

d)
4-Chloro-1-difluoromethyl-1H-pyrazole-3-carboxylic acid methoxy-methyl-amide

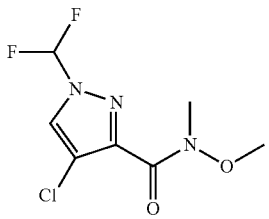

A solution of 4-chloro-1-difluoromethyl-1H-pyrazole-3-carboxylic acid (150 mg, 0.76 mmole) in dichloromethane (5 ml) was subsequently treated at 23° C. with N,O-dimethylhydroxylamine hydrochloride (78 mg, 0.80 mmole), N-methylmorpholine (0.09 ml, 0.8 mmole) and EDCI.HCl (154 mg, 0.8 mmole) and stirring was continued for 16 h. The mixture was washed with 1 M aqueous HCl and H$_2$O, the organic layer was dried, evaporated and the residue purified by chromatography on silica gel using cyclohexane/AcOEt (2:1) to give the title compound (164 mg) as a colorless oil. MS: m/z=240.1 [M]$^+$.

e) 4-Chloro-1-difluoromethyl-1H-pyrazole-3-carbaldehyde

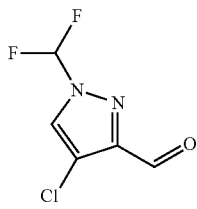 [SMILES: O=Cc1nn(C(F)F)cc1Cl]

To a solution of 4-chloro-1-difluoromethyl-1H-pyrazole-3-carboxylic acid methoxy-methyl-amide (164 mg, 0.68 mmole) in THF (5 ml) was added at 0° C. a solution of LiAlH$_4$ (1M in THF, 0.35 ml) and stirring was continued for 30 min. The mixture was quenched at −15° C. with saturated aqueous KHSO$_4$, extracted with diethyl ether, the organic layer was dried, evaporated and the residue purified by chromatography on silica gel using cyclohexane/AcOEt (4:1) to give the title compound (71 mg) as a pale yellow oil.

Example 3

(5R,6R)-6-Fluoro-5-[2-fluoro-5-(tetrahydro-furan-3-ylamino)-phenyl]-5-methyl-2,5,6,7-tetrahydro-[1,4]oxazepin-3-ylamine In an analogous manner as described for example 1 the reductive amination of (5R,6R)-5-(5-amino-2-fluoro-phenyl)-6-fluoro-5-methyl-2,5,6,7-tetrahydro-1,4-oxazepin-3-ylamine (intermediate A10B) (20 mg, 78.4 μmol) and dihydrofuran-3(2H)-one (3-oxotetrahydrofuran) (CAS [22929-52-8]) (7.42 mg, 6.67 μl, 86.2 μmol) yielded the title compound (11.4 mg, 44.7%) as a colorless solid. MS (ISP): m/z=326.3 [M+H]$^+$.

Example 4

(5R,6R)-6-Fluoro-5-[2-fluoro-5-(tetrahydro-pyran-3-ylamino)-phenyl]-5-methyl-2,5,6,7-tetrahydro-[1,4]oxazepin-3-ylamine In an analogous manner as described for example 1 the reductive amination of (5R,6R)-5-(5-amino-2-fluoro-phenyl)-6-fluoro-5-methyl-2,5,6,7-tetrahydro-1,4-oxazepin-3-ylamine (intermediate A10B) (20 mg, 78.4 μmol) and dihydro-2H-pyran-3(4H)-one (CAS [23462-75-1]) (8.63 mg, 86.2 μmol) yielded the title compound (13.2 mg, 49.6%) as a colorless solid. MS (ISP): m/z=340.2 [M+H]$^+$.

Example 5

(5R,6R)-6-Fluoro-5-[2-fluoro-5-(tetrahydro-pyran-4-ylamino)-phenyl]-5-methyl-2,5,6,7-tetrahydro-[1,4]oxazepin-3-ylamine In an analogous manner as described for example 1 the reductive amination of (5R,6R)-5-(5-amino-2-fluoro-phenyl)-6-fluoro-5-methyl-2,5,6,7-tetrahydro-1,4-oxazepin-3-ylamine (intermediate A10B) (20 mg, 78.4 μmol) and dihydro-2H-pyran-4(3H)-one (CAS [29943-42-8]) (8.63 mg, 7.96 μl, 86.2 μmol) yielded the title compound (10.2 mg, 38.4%) as a colorless oil. MS (ISP): m/z=340.2 [M+H]$^+$.

Example 6

(R)-5-{5-[(4-Chloro-1-difluoromethyl-1H-pyrazol-3-ylmethyl)-amino]-2-fluoro-phenyl}-6,6-difluoro-5-methyl-2,5,6,7-tetrahydro-[1,4]oxazepin-3-ylamine In an analogous manner as described for example 2 the reductive amination of (R)-5-(5-amino-2-fluorophenyl)-6,6-difluoro-5-methyl-2,5,6,7-tetrahydro-1,4-oxazepin-3-amine (intermediate A10A) (27.3 mg, 100 μmol) and 4-chloro-1-difluoromethyl-1H-pyrazole-3-carbaldehyde (19.9 mg, 110 μmol) yielded the title compound (5 mg, 11.4%) as a colorless oil. MS (ISP): m/z=438.2 [M+H]$^+$ and 440.1 [(M+2+H)$^+$].

Example 7

(R)-5-{5-[(4-Chloro-1-difluoromethyl-1H-pyrazol-3-ylmethyl)-amino]-2-fluoro-phenyl}-5-ethyl-6,6-difluoro-2,5,6,7-tetrahydro-[1,4]oxazepin-3-ylamine In an analogous manner as described for example 2 the reductive amination of (R)-5-(5-amino-2-fluoro-phenyl)-5-ethyl-6,6-difluoro-2,5,6,7-tetrahydro-[1,4]oxazepin-3-ylamine (intermediate A10F) (28.7 mg, 100 μmol) and 4-chloro-1-difluoromethyl-1H-pyrazole-3-carbaldehyde (19.9 mg, 110 μmol) yielded the title compound (10.5 mg, 23.2%) as a colorless oil. MS (ISP): m/z=452.1 [M+H]$^+$ and 454.1 [(M+2+H)$^+$].

Example 8

[3-((R)-3-Amino-6,6-difluoro-5-methyl-2,5,6,7-tetrahydro-[1,4]oxazepin-5-yl)-4-fluoro-phenyl]-((S)-3-chloro-6,7-dihydro-5H-[1]pyrindin-7-yl)-amine To a solution of (R)-5-[5-((S)-3-chloro-6,7-dihydro-5H-[1]pyrindin-7-ylamino)-2-fluoro-phenyl]-6,6-difluoro-5-methyl-[1,4]oxazepane-3-thione (intermediate A20Ab) (16 mg, 36.2 µmol) in 7 M ammonia in methanol (0.4 mL, 2.8 mmol) at 23° C. was added tert-butyl hydroperoxide (70% in water, 16.3 mg, 17.4 µL, 181 µmol) and the mixture stirred at 23° C. for 22 hours. Poured into aqueous 2 M $Na_2CO_3$ solution, extracted with ethyl acetate, the organic layer was dried over $Na_2SO_4$. Removal of the solvent in vacuum left a light brown solid, which was purified by flash chromatography (silica gel (amine)) with n-heptane/ethyl acetate to give the title compound as a yellow solid (7 mg, 45%). MS (ISP): m/z=425.1 [M+H]$^+$.

Example 9

[3-((R)-3-Amino-6,6-difluoro-5-methyl-2,5,6,7-tetrahydro-[1,4]oxazepin-5-yl)-4-fluoro-phenyl]-((R)-3-chloro-6,7-dihydro-5H-[1]pyrindin-7-yl)-amine Prepared in an analogous manner as described for example 8 from (R)-5-[5-((R)-3-chloro-6,7-dihydro-5H-[1]pyrindin-7-ylamino)-2-fluoro-phenyl]-6,6-difluoro-5-methyl-[1,4]oxazepane-3-thione (intermediate A20Aa) (20 mg, 45.3 µmol). The title compound was obtained as a yellow solid (15 mg, 78%). MS (ISP): m/z=425.1 [M+H]$^+$.

Example 10

4-[3-((R)-3-Amino-6,6-difluoro-5-methyl-2,5,6,7-tetrahydro-[1,4]oxazepin-5-yl)-4-fluoro-phenylamino]-benzonitrile To a solution of (R)-4-(3-(3-(bis(4-methoxyphenyl)(phenyl)methylamino)-6,6-difluoro-5-methyl-2,5,6,7-tetrahydro-1,4-oxazepin-5-yl)-4-fluorophenylamino)benzonitrile (intermediate A13A) (21 mg, 31 µmol) in dichloromethane (1 ml) at 23° C. was added trifluoroacetic acid (370 mg, 250 µl, 3.24 mmol) and the mixture was stirred at 23° C. for 1 h. Poured into sat. $Na_2CO_3$-sol., extracted thrice with ethyl acetate, dried the combined organic layer over $Na_2SO_4$. Removal of the solvent in vacuum left a crude product, which was purified by preparative HPLC (column: Gemini 5µ C18 110 A° AXIA (50×21.2 mm); flow: 40 ml/min; gradient: water (+0.1% TEA)/acetonitrile (90%-10% 1 min plateau; in 3.5 min to 5%-95%); collection: UV-detector 300 nm) to give the title compound (8.9 mg, 76.6%) after trituration with little diethyl ether/pentane as a white solid. MS (ISP): m/z=375.3 [M+H]$^+$.

Example 12

(S)-7-[3-((R)-3-Amino-6,6-difluoro-5,7,7-trimethyl-2,5,6,7-tetrahydro-[1,4]oxazepin-5-yl)-4-fluoro-phenylamino]-6,7-dihydro-5H-[1]pyrindine-3-carbonitrile Prepared in an analogous manner as described for example 8 from (S)-7-[3-((R)-6,6-difluoro-5,7,7-trimethyl-3-thioxo-[1,4]oxazepan-5-yl)-4-fluoro-phenylamino]-6,7-dihydro-5H-[1]pyrindine-3-carbonitrile (intermediate A20Ba) (155 mg, 337 µmol). The title compound was obtained as a light brown foam (65 mg, 43.5%). MS (ISP): m/z=444.2 [M+H]$^+$.

Example 13

(R)-7-[3-((R)-3-Amino-6,6-difluoro-5,7,7-trimethyl-2,5,6,7-tetrahydro-[1,4]oxazepin-5-yl)-4-fluoro-phenylamino]-6,7-dihydro-5H-[1]pyrindine-3-carbonitrile Prepared in an analogous manner as described for example 8 from (R)-7-[3-((R)-6,6-difluoro-5,7,7-trimethyl-3-thioxo-[1,4]oxazepan-5-yl)-4-fluoro-phenylamino]-6,7-dihydro-5H-[1]pyrindine-3-carbonitrile (intermediate A20Bb) (145 mg, 315 µmol). The title compound was obtained as a light brown foam (51 mg, 36.5%). MS (ISP): m/z=444.3 [M+H]$^+$.

Example 14

[3-((R)-3-Amino-6,6-difluoro-5,7,7-trimethyl-2,5,6,7-tetrahydro-[1,4]oxazepin-5-yl)-4-fluoro-phenyl]-(3-chloro-6,7-dihydro-5H-[1]pyrindin-7-yl)-amine Prepared in an analogous manner as described for example 8 from (R)-5-[5-(3-chloro-6,7-dihydro-5H-[1]pyrindin-7-ylamino)-2-fluoro-phenyl]-6,6-difluoro-5,7,7-trimethyl-[1,4]oxazepane-3-thione (intermediate A20C) (82 mg, 174 µmol). The title compound was obtained as a white foam (40 mg, 51%). MS (ISP): m/z=453.2 [M+H]$^+$ and 455.3 [M+2+H]$^+$.

Example 15

[3-((R)-3-Amino-6,6-difluoro-5,7,7-trimethyl-2,5,6,7-tetrahydro-[1,4]oxazepin-5-yl)-4-fluoro-phenyl]-(6-chloro-2,3-dihydro-furo[3,2-b]pyridin-3-yl)-amine Prepared in an analogous manner as described for example 8 from (5R)-5-(5-(6-chloro-2,3-dihydrofuro[3,2-b]pyridin-3-ylamino)-2-fluorophenyl)-6,6-difluoro-5,7,7-trimethyl-1,4-oxazepane-3-thione (intermediate A20D) (64 mg, 136 µmol). The title compound was obtained as an off-white foam (23 mg, 37.3%). MS (ISP): m/z=455.1 [M+H]$^+$ and 457.2 [M+2+H]$^+$.

Example 16

8-[3-((R)-3-Amino-6,6-difluoro-5,7,7-trimethyl-2,5,6,7-tetrahydro-[1,4]oxazepin-5-yl)-4-fluoro-phenylamino]-5,6,7,8-tetrahydro-quinoline-3-carbonitrile Prepared in an analogous manner as described for example 8 from 8-(3-((R)-6,6-difluoro-5,7,7-trimethyl-3-thioxo-1,4-oxazepan-5-yl)-4-fluorophenylamino)-5,6,7,8-tetrahydro-quinoline-3-carbonitrile (intermediate A20E) (94 mg, 198 µmol). The title compound was obtained as a light brown foam (35 mg, 38.6%). MS (ISP): m/z=458.2 [M+H]$^+$.

Example 17

(R)-5-[5-(6-Chloro-2,3-dihydro-benzofuran-3-ylamino)-2-fluoro-phenyl]-6,6-difluoro-5,7,7-trimethyl-2,5,6,7-tetrahydro-[1,4]oxazepin-3-ylamine Prepared in an analogous manner as described for example 8 from (5R)-5-(5-(6-chloro-2,3-dihydrobenzofuran-3- ylamino)-2-fluorophenyl)-6,6-difluoro-5,7,7-trimethyl-1,4-oxazepane-3-thione (intermediate A20F) (70 mg, 149 μmol). The title compound was obtained as a light brown foam (29 mg, 38.7%). MS (ISP): m/z=454.2 [M+H]$^+$ and 456.3 [M+2+H]$^+$.

Example 18

(R)-6,6-Difluoro-5-[2-fluoro-5-(1-methyl-1H-pyrazol-3-ylamino)-phenyl]-5,7,7-trimethyl-2,5,6,7-tetrahydro-[1,4]oxazepin-3-ylamine Prepared in an analogous manner as described for example 10 from (R)—N-(bis(4-methoxyphenyl)(phenyl)methyl)-6,6-difluoro-5-(2-fluoro-5-(1-methyl-1H-pyrazol-3-ylamino)phenyl)-5,7,7-trimethyl-2,5,6,7-tetrahydro-1,4-oxazepin-3-amine (intermediate A13) (171.5 mg, 251 μmol). The title compound was obtained as white foam (38 mg, 37.4%). MS (ISP): m/z=382 [M+H]$^+$.

Example 19

(R)-6,6-Difluoro-5-[2-fluoro-5-(4-fluoro-phenylamino)-phenyl]-5,7,7-trimethyl-2,5,6,7-tetrahydro-[1,4]oxazepin-3-ylamine Prepared in an analogous manner as described for example 8 from (R)-6,6-difluoro-5-(2-fluoro-5-(4-fluorophenylamino)phenyl)-5,7,7-trimethyl-1,4-oxazepane-3-thione (intermediate A20G) (100 mg, 242 μmol). The title compound was obtained as a light yellow gum (36 mg, 37.6%). MS (ISP): m/z=396.2 [M+H]$^+$.

Example 20

(S)-7-[5-((R)-3-Amino-6,6-difluoro-5,7,7-trimethyl-2,5,6,7-tetrahydro-[1,4]oxazepin-5-yl)-2,4-difluoro-phenylamino]-6,7-dihydro-5H-[1]pyrindine-3-carbonitrile Prepared in an analogous manner as described for example 8 from (S)-7-(5-((R)-6,6-difluoro-5,7,7-trimethyl-3-thioxo-1,4-oxazepan-5-yl)-2,4-difluorophenylamino)-6,7-dihydro-5H-cyclopenta[b]pyridine-3-carbonitrile (intermediate A20Hb) (47 mg, 98.2 μmol). The title compound was obtained as a light brown foam (12 mg, 26.5%). MS (ISP): m/z=462.2 [M+H]$^+$.

Example 21

(R)-7-[5-((R)-3-Amino-6,6-difluoro-5,7,7-trimethyl-2,5,6,7-tetrahydro-[1,4]oxazepin-5-yl)-2,4-difluoro-phenylamino]-6,7-dihydro-5H-[1]pyrindine-3-carbonitrile Prepared in an analogous manner as described for example 8 from (R)-7-(5-((R)-6,6-difluoro-5,7,7-trimethyl-3-thioxo-1,4-oxazepan-5-yl)-2,4-difluorophenylamino)-6,7-dihydro-5H-cyclopenta[b]pyridine-3-carbonitrile (intermediate A20Ha) (56 mg, 117 μmol). The title compound was obtained as a light brown foam (18 mg, 33.3%). MS (ISP): m/z=462.2 [M+H]$^+$.

Example 22

(R)-5-[5-(6-Chloro-pyridin-3-ylamino)-2-fluoro-phenyl]-6,6-difluoro-5,7,7-trimethyl-2,5,6,7-tetrahydro-[1,4]oxazepin-3-ylamine Prepared in an analogous manner as described for example 8 from (R)-5-(5-(6-chloropyridin-3-ylamino)-2-fluorophenyl)-6,6-difluoro-5,7,7-trimethyl-1,4-oxazepan-3-one (intermediate A20I) (40 mg, 93 μmol). The title compound was obtained as a colorless gum (5.1 mg, 13.3%). MS (ISP): m/z=413.3 [M+H]$^+$ and 415.2 [M+2+H]$^+$.

Example 23

(R)-6,6-Difluoro-5-[2-fluoro-5-(5-fluoro-pyridin-3-ylamino)-phenyl]-5,7,7-trimethyl-2,5,6,7-tetrahydro-[1,4]oxazepin-3-ylamine Prepared in an analogous manner as described for example 8 from (R)-6,6-difluoro-5-(2-fluoro-5-(5-fluoropyridin-3-ylamino)phenyl)-5,7,7-trimethyl-1,4-oxazepane-3-thione (intermediate A20J) (28 mg, 68 μmol). The title compound was obtained as white foam (6.8 mg, 25.3%). MS (ISP): m/z=397.2 [M+H]$^+$.

Example 24

(R)-6,6-Difluoro-5-[2-fluoro-5-(pyridin-3-ylamino)-phenyl]-5,7,7-trimethyl-2,5,6,7-tetrahydro-[1,4]oxazepin-3-ylamine Prepared in an analogous manner as described for example 8 from (R)-6,6-difluoro-5-(2-fluoro-5-(pyridin-3-ylamino)phenyl)-5,7,7-trimethyl-1,4-oxazepane-3-thione (intermediate A20K) (38 mg, 96 μmol). The title compound was obtained as white foam (15.6 mg, 42.9%). MS (ISP): m/z=379.3 [M+H]$^+$.

Example 25

(R)-6,6-Difluoro-5-[2-fluoro-5-(6-methoxy-pyridin-3-ylamino)-phenyl]-5,7,7-trimethyl-2,5,6,7-tetrahydro-[1,4]oxazepin-3-ylamine Prepared in an analogous manner as described for example 8 from (R)-6,6-difluoro-5-(2-fluoro-5-(6-methoxypyridin-3-ylamino)phenyl)-5,7,7-trimethyl-1,4-oxazepane-3-thione (intermediate A20L) (61 mg, 61 μmol). The title compound was obtained as off-white foam (14 mg, 56%). MS (ISP): m/z=409.3 [M+H]$^+$.

Example 26

(R)-6,6-Difluoro-5-[2-fluoro-5-(5-trifluoromethyl-pyridin-3-ylamino)-phenyl]-5,7,7-trimethyl-2,5,6,7-tetrahydro-[1,4]oxazepin-3-ylamine Prepared in an analogous manner as described for example 8 from (R)-6,6-difluoro-5-(2-fluoro-5-(5-(trifluoromethyl)

pyridin-3-ylamino)phenyl)-5,7,7-trimethyl-1,4-oxazepane-3-thione (intermediate A20M) (80 mg, 173 μmol). The title compound was obtained as an off-white solid (21 mg, 27%). MS (ISP): m/z=448.2 [M+H]$^+$.

Example 27

(R)-6,6-Difluoro-5-[2-fluoro-5-(6-methyl-pyridin-3-ylamino)-phenyl]-5,7,7-trimethyl-2,5,6,7-tetrahydro-[1,4]oxazepin-3-ylamine Prepared in an analogous manner as described for example 8 from (R)-6,6-difluoro-5-(2-fluoro-5-(6-methylpyridin-3-ylamino)phenyl)-5,7,7-trimethyl-1,4-oxazepane-3-thione (intermediate A20N) (7.2 mg, 17.6 μmol). The title compound was obtained as colorless gum (3.1 mg, 44.9%). MS (ISP): m/z=393.2 [M+H]$^+$.

Example 28

(R)-6,6-Difluoro-5-{2-fluoro-5-[6-(2,2,2-trifluoro-ethoxy)-pyridin-3-ylamino]-phenyl}-5,7,7-trimethyl-2,5,6,7-tetrahydro-[1,4]oxazepin-3-ylamine a) (R)-6,6-Difluoro-5-{2-fluoro-5-[6-(2,2,2-trifluoro-ethoxy)-pyridin-3-ylamino]-phenyl}-5,7,7-trimethyl-[1,4]oxazepan-3-one In an analogous manner as described for the preparation of the intermediates A9A or A13A, the palladium-catalyzed coupling of (R)-5-(5-bromo-2-fluorophenyl)-6,6-difluoro-5,7,7-trimethyl-[1,4]oxazepan-3-one (intermediate A16B) (200 mg, 546 μmol) with 6-(2,2,2-trifluoro-ethoxy)-pyridin-3-ylamine (CAS 72617-82-4) (210 mg, 1.09 mmol) yielded the title compound (179 mg, 68.6%) as a light brown solid. MS (ISP): m/z=478.1 [M+H]$^+$.

b) (R)-6,6-Difluoro-5-{2-fluoro-5-[6-(2,2,2-trifluoro-ethoxy)-pyridin-3-ylamino]-phenyl}-5,7,7-trimethyl-[1,4]oxazepan-3-thione In an analogous manner as described for the preparation of intermediate A20A, the treatment of (R)-6,6-difluoro-5-{2-fluoro-5-[6-(2,2,2-trifluoro-ethoxy)-pyridin-3-ylamino]-phenyl}-5,7,7-trimethyl-[1,4]oxazepan-3-one (159 mg, 333 μmol) with Lawesson's reagent (135 mg, 333 μmol) yielded the title compound (139 mg, 84.6%) as a white solid. MS (ISP): m/z=494.1 [M+H]$^+$.

c) (R)-6,6-Difluoro-5-{2-fluoro-5-[6-(2,2,2-trifluoro-ethoxy)-pyridin-3-ylamino]-phenyl}-5,7,7-trimethyl-2,5,6,7-tetrahydro-[1,4]oxazepin-3-ylamine In an analogous manner as described for example 8, the treatment of (R)-6,6-difluoro-5-{2-fluoro-5-[6-(2,2,2-trifluoro-ethoxy)-pyridin-3-ylamino]-phenyl}-5,7,7-trimethyl-[1,4]oxazepan-3-thione (106 mg, 215 μmol) with 7 M ammonia in methanol (1.84 ml, 12.9 mmol) and tert-butyl hydroperoxide (70% in water; 178 μL, 1.29 mmol) at 23° C. for 16 hours yielded the title compound (69 mg, 67.4%) as a light yellow foam. MS (ISP): m/z=477.2 [M+H]$^+$.

The invention claimed is:
1. A compound of formula I,

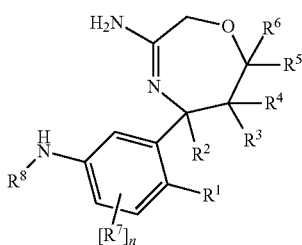

wherein
$R^1$ is selected from the group consisting of
  hydrogen,
  halogen, and
  $C_{1-6}$-alkyl;
$R^2$ is selected from the group consisting of
  hydrogen,
  $C_{1-6}$-alkyl, and
  halogen-$C_{1-6}$-alkyl;
$R^3$ is selected from the group consisting of
  halogen,
  hydrogen, and
  $C_{1-6}$-alkyl;
$R^4$ is selected from the group consisting of
  hydrogen and
  halogen;
$R^5$ is selected from the group consisting of
  hydrogen and
  $C_{1-6}$-alkyl;
$R^6$ is selected from the group consisting of
  hydrogen and
  $C_{1-6}$-alkyl;
$R^7$ is selected from the group consisting of
  halogen and
  $C_{1-6}$-alkyl;
n is 0 or 1; and
$R^8$ is selected from the group consisting of
  heteroaryl,
  heteroaryl, substituted by 1-4 substituents individually selected from the group consisting of cyano, cyano-$C_{1-6}$-alkyl, halogen, halogen-$C_{1-6}$-alkyl, halogen-$C_{1-6}$-alkoxy, $C_{1-6}$-alkoxy and $C_{1-6}$-alkyl,
  heteroaryl-$CH_2$—,
  heteroaryl-$CH_2$—, substituted by 1-4 substituents individually selected from the group consisting of cyano, cyano-$C_{1-6}$-alkyl, halogen, halogen-$C_{1-6}$-alkyl, halogen-$C_{1-6}$-alkoxy, $C_{1-6}$-alkoxy and $C_{1-6}$-alkyl,
  aryl,
  aryl, substituted by 1-4 substituents individually selected from the group consisting of cyano, cyano-$C_{1-6}$-alkyl, halogen, halogen-$C_{1-6}$-alkyl, halogen-$C_{1-6}$-alkoxy, $C_{1-6}$-alkoxy and $C_{1-6}$-alkyl,
  heterocyclyl, and
  heterocyclyl, substituted by 1-4 substituents individually selected from the group consisting of cyano, cyano-$C_{1-6}$-alkyl, halogen, halogen-$C_{1-6}$-alkyl, halogen-$C_{1-6}$-alkoxy, $C_{1-6}$-alkoxy and $C_{1-6}$-alkyl; or a pharmaceutically acceptable salt thereof.

2. The compound of claim 1, having formula Ia

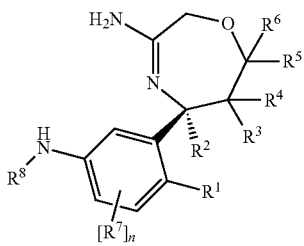

wherein
R¹ is selected from the group consisting of
 hydrogen,
 halogen, and
 $C_{1-6}$-alkyl;
R² is selected from the group consisting of
 hydrogen,
 $C_{1-6}$-alkyl, and
 halogen-$C_{1-6}$-alkyl;
R³ is selected from the group consisting of
 halogen,
 hydrogen, and
 $C_{1-6}$-alkyl;
R⁴ is selected from the group consisting of
 hydrogen and
 halogen;
R⁵ is selected from the group consisting of
 hydrogen and
 $C_{1-6}$-alkyl;
R⁶ is selected from the group consisting of
 hydrogen and
 $C_{1-6}$-alkyl;
R⁷ is selected from the group consisting of
 halogen and
 $C_{1-6}$-alkyl;
n is 0 or 1; and
R⁸ is selected from the group consisting of
 heteroaryl,
 heteroaryl, substituted by 1-4 substituents individually selected from the group consisting of cyano, cyano-$C_{1-6}$-alkyl, halogen, halogen-$C_{1-6}$-alkyl, halogen-$C_{1-6}$-alkoxy, $C_{1-6}$-alkoxy and $C_{1-6}$-alkyl,
 heteroaryl-$CH_2$—,
 heteroaryl-$CH_2$—, substituted by 1-4 substituents individually selected from the group consisting of cyano, cyano-$C_{1-6}$-alkyl, halogen, halogen-$C_{1-6}$-alkyl, halogen-$C_{1-6}$-alkoxy, $C_{1-6}$-alkoxy and $C_{1-6}$-alkyl,
 aryl,
 aryl, substituted by 1-4 substituents individually selected from the group consisting of cyano, cyano-$C_{1-6}$-alkyl, halogen, halogen-$C_{1-6}$-alkyl, halogen-$C_{1-6}$-alkoxy, $C_{1-6}$-alkoxy and $C_{1-6}$-alkyl,
 heterocyclyl, and
 heterocyclyl, substituted by 1-4 substituents individually selected from the group consisting of cyano, cyano-$C_{1-6}$-alkyl, halogen, halogen-$C_{1-6}$-alkyl, halogen-$C_{1-6}$-alkoxy, $C_{1-6}$-alkoxy and $C_{1-6}$-alkyl;
or a pharmaceutically acceptable salt thereof.
3. The compound of claim 1, wherein R¹ is halogen.
4. The compound of claim 3, wherein R¹ is F.
5. The compound of claim 1, wherein R² is $C_{1-6}$-alkyl.
6. The compound of claim 5, wherein R² is Me.

7. The compound of claim 1, wherein R³ is halogen.
8. The compound of claim 7, wherein R³ is F.
9. The compound of claim 1, wherein R⁴ is halogen.
10. The compound of claim 9, wherein R⁴ is F.
11. The compound of claim 1, wherein R⁴ is hydrogen.
12. The compound of claim 1, wherein R⁵ is $C_{1-6}$-alkyl.
13. The compound of claim 12, wherein R⁵ is Me.
14. The compound of claim 1, wherein R⁵ is hydrogen.
15. The compound of claim 1, wherein R⁶ is $C_{1-6}$-alkyl.
16. The compound of claim 15, wherein R⁶ is Me.
17. The compound of claim 1, wherein R⁶ is hydrogen.
18. The compound of claim 1, wherein n is 0.
19. The compound of claim 1, wherein R⁸ is selected from the group consisting of
 heteroaryl, substituted by 1-2 substituents individually selected from the group consisting of cyano, halogen, $C_{1-6}$-alkoxy and $C_{1-6}$-alkyl;
 heteroaryl-$CH_2$—, substituted by 1-2 substituents individually selected from the group consisting of halogen and halogen-$C_{1-6}$-alkyl;
 aryl, substituted by 1-2 substituents individually selected from the group consisting of cyano, and halogen, and
 heterocyclyl.
20. The compound of claim 19, wherein R⁸ is selected from the group consisting of heteroaryl substituted by halogen or $C_{1-6}$-alkyl and aryl substituted by halogen.
21. The compound of claim 19, wherein R⁸ is selected from the group consisting of 3-chloro-6,7-dihydro-5H-[1]pyrindin-7-yl, 1-methyl-1H-pyrazol-3-yl and 4-fluoro-phenyl.
22. The compound of claim 1, selected from the group consisting of
 [3-((5R,6R)-3-Amino-6-fluoro-5-methyl-2,5,6,7-tetrahydro-[1,4]oxazepin-5-yl)-4-fluoro-phenyl]-(3-chloro-6,7-dihydro-5H-[1]pyrindin-7-yl)-amine,
 (5R,6R)-5-{5-[(4-Chloro-1-difluoromethyl-1H-pyrazol-3-ylmethyl)-amino]-2-fluoro-phenyl}-6-fluoro-5-methyl-2,5,6,7-tetrahydro-[1,4]oxazepin-3-ylamine,
 (5R,6R)-6-Fluoro-5-[2-fluoro-5-(tetrahydro-furan-3-ylamino)-phenyl]-5-methyl-2,5,6,7-tetrahydro-[1,4]oxazepin-3-ylamine,
 (5R,6R)-6-Fluoro-5-[2-fluoro-5-(tetrahydro-pyran-3-ylamino)-phenyl]-5-methyl-2,5,6,7-tetrahydro-[1,4]oxazepin-3-ylamine,
 (5R,6R)-6-Fluoro-5-[2-fluoro-5-(tetrahydro-pyran-4-ylamino)-phenyl]-5-methyl-2,5,6,7-tetrahydro-[1,4]oxazepin-3-ylamine,
 (R)-5-[5-(6-Chloro-2,3-dihydro-benzofuran-3-ylamino)-2-fluoro-phenyl]-6,6-difluoro-5,7,7-trimethyl-2,5,6,7-tetrahydro-[1,4]oxazepin-3-ylamine,
 (R)-5-[5-(6-Chloro-pyridin-3-ylamino)-2-fluoro-phenyl]-6,6-difluoro-5,7,7-trimethyl-2,5,6,7-tetrahydro-[1,4]oxazepin-3-ylamine,
 (R)-5-{5-[(4-Chloro-1-difluoromethyl-1H-pyrazol-3-ylmethyl)-amino]-2-fluoro-phenyl}-6,6-difluoro-5-methyl-2,5,6,7-tetrahydro-[1,4]oxazepin-3-ylamine, and
 (R)-5-{5-[(4-Chloro-1-difluoromethyl-1H-pyrazol-3-ylmethyl)-amino]-2-fluoro-phenyl}-5-ethyl-6,6-difluoro-2,5,6,7-tetrahydro-[1,4]oxazepin-3-ylamine,
or a pharmaceutical acceptable salt thereof.
23. The compound of claim 1, selected from the group consisting of
 (R)-6,6-Difluoro-5-[2-fluoro-5-(1-methyl-1H-pyrazol-3-ylamino)-phenyl]-5,7,7-trimethyl-2,5,6,7-tetrahydro-[1,4]oxazepin-3-ylamine,
 (R)-6,6-Difluoro-5-[2-fluoro-5-(4-fluoro-phenylamino)-phenyl]-5,7,7-trimethyl-2,5,6,7-tetrahydro-[1,4]oxazepin-3-ylamine, (R)-6,6-Difluoro-5-[2-fluoro-5-(5-fluoro-pyridin-3-ylamino)-phenyl]-5,7,7-trimethyl-2,5,6,7-tetrahydro-[1,4]oxazepin-3-ylamine,
(R)-6,6-Difluoro-5-[2-fluoro-5-(5-trifluoromethyl-pyridin-3-ylamino)-phenyl]-5,7,7-trimethyl-2,5,6,7-tetrahydro-[1,4]oxazepin-3-ylamine,
(R)-6,6-Difluoro-5-[2-fluoro-5-(6-methoxy-pyridin-3-ylamino)-phenyl]-5,7,7-trimethyl-2,5,6,7-tetrahydro-[1,4]oxazepin-3-ylamine,
(R)-6,6-Difluoro-5-[2-fluoro-5-(6-methyl-pyridin-3-ylamino)-phenyl]-5,7,7-trimethyl-2,5,6,7-tetrahydro-[1,4]oxazepin-3-ylamine,
(R)-6,6-Difluoro-5-[2-fluoro-5-(pyridin-3-ylamino)-phenyl]-5,7,7-trimethyl-2,5,6,7-tetrahydro-[1,4]oxazepin-3-ylamine,
(R)-7-[3-((R)-3-Amino-6,6-difluoro-5,7,7-trimethyl-2,5,6,7-tetrahydro-[1,4]oxazepin-5-yl)-4-fluoro-phenylamino]-6,7-dihydro-5H-[1]pyrindine-3-carbonitrile, and
(R)-7-[5-((R)-3-Amino-6,6-difluoro-5,7,7-trimethyl-2,5,6,7-tetrahydro-[1,4]oxazepin-5-yl)-2,4-difluoro-phenylamino]-6,7-dihydro-5H-[1]pyrindine-3-carbonitrile,
or a pharmaceutical acceptable salt thereof.

24. The compound of claim 1, selected from the group consisting of
(S)-7-[3-((R)-3-Amino-6,6-difluoro-5,7,7-trimethyl-2,5,6,7-tetrahydro-[1,4]oxazepin-5-yl)-4-fluoro-phenylamino]-6,7-dihydro-5H-[1]pyrindine-3-carbonitrile,
[3-((R)-3-Amino-6,6-difluoro-5,7,7-trimethyl-2,5,6,7-tetrahydro-[1,4]oxazepin-5-yl)-4-fluoro-phenyl]-(3-chloro-6,7-dihydro-5H-[1]pyrindin-7-yl)-amine,
[3-((R)-3-Amino-6,6-difluoro-5,7,7-trimethyl-2,5,6,7-tetrahydro-[1,4]oxazepin-5-yl)-4-fluoro-phenyl]-(6-chloro-2,3-dihydro-furo[3,2-b]pyridin-3-yl)-amine,
[3-((R)-3-Amino-6,6-difluoro-5-methyl-2,5,6,7-tetrahydro-[1,4]oxazepin-5-yl)-4-fluoro-phenyl]-((S)-3-chloro-6,7-dihydro-5H-[1]pyrindin-7-yl)-amine,
[3-((R)-3-Amino-6,6-difluoro-5-methyl-2,5,6,7-tetrahydro-[1,4]oxazepin-5-yl)-4-fluoro-phenyl]-((R)-3-chloro-6,7-dihydro-5H-[1]pyrindin-7-yl)-amine,
4-[3-((R)-3-Amino-6,6-difluoro-5-methyl-2,5,6,7-tetrahydro-[1,4]oxazepin-5-yl)-4-fluoro-phenylamino]-benzonitrile,
8-[3-((R)-3-Amino-6,6-difluoro-5,7,7-trimethyl-2,5,6,7-tetrahydro-[1,4]oxazepin-5-yl)-4-fluoro-phenylamino]-5,6,7,8-tetrahydro-quinoline-3-carbonitrile,
(S)-7-[5-((R)-3-Amino-6,6-difluoro-5,7,7-trimethyl-2,5,6,7-tetrahydro-[1,4]oxazepin-5-yl)-2,4-difluoro-phenylamino]-6,7-dihydro-5H-[1]pyrindine-3-carbonitrile, and
(R)-6,6-Difluoro-5-{2-fluoro-5-[6-(2,2,2-trifluoro-ethoxy)-pyridin-3-ylamino]-phenyl}-5,7,7-trimethyl-2,5,6,7-tetrahydro-[1,4]oxazepin-3-ylamine,
or a pharmaceutical acceptable salt thereof.

25. The compound of claim 1, selected from the group consisting of
[3-((5R,6R)-3-Amino-6-fluoro-5-methyl-2,5,6,7-tetrahydro-[1,4]oxazepin-5-yl)-4-fluoro-phenyl]-(3-chloro-6,7-dihydro-5H-[1]pyrindin-7-yl)-amine,
(5R,6R)-5-{5-[(4-Chloro-1-difluoromethyl-1H-pyrazol-3-ylmethyl)-amino]-2-fluoro-phenyl}-6-fluoro-5-methyl-2,5,6,7-tetrahydro-[1,4]oxazepin-3-ylamine,
(5R,6R)-6-Fluoro-5-[2-fluoro-5-(tetrahydro-furan-3-ylamino)-phenyl]-5-methyl-2,5,6,7-tetrahydro-[1,4]oxazepin-3-ylamine,
(5R,6R)-6-Fluoro-5-[2-fluoro-5-(tetrahydro-pyran-3-ylamino)-phenyl]-5-methyl-2,5,6,7-tetrahydro-[1,4]oxazepin-3-ylamine,
(5R,6R)-6-Fluoro-5-[2-fluoro-5-(tetrahydro-pyran-4-ylamino)-phenyl]-5-methyl-2,5,6,7-tetrahydro-[1,4]oxazepin-3-ylamine,
(R)-5-[5-(6-Chloro-2,3-dihydro-benzofuran-3-ylamino)-2-fluoro-phenyl]-6,6-difluoro-5,7,7-trimethyl-2,5,6,7-tetrahydro-[1,4]oxazepin-3-ylamine,
(R)-5-[5-(6-Chloro-pyridin-3-ylamino)-2-fluoro-phenyl]-6,6-difluoro-5,7,7-trimethyl-2,5,6,7-tetrahydro-[1,4]oxazepin-3-ylamine,
(R)-5-{5-[(4-Chloro-1-difluoromethyl-1H-pyrazol-3-ylmethyl)-amino]-2-fluoro-phenyl}-6,6-difluoro-5-methyl-2,5,6,7-tetrahydro-[1,4]oxazepin-3-ylamine,
(R)-5-{5-[(4-Chloro-1-difluoromethyl-1H-pyrazol-3-ylmethyl)-amino]-2-fluoro-phenyl}-5-ethyl-6,6-difluoro-2,5,6,7-tetrahydro-[1,4]oxazepin-3-ylamine,
(R)-6,6-Difluoro-5-[2-fluoro-5-(1-methyl-1H-pyrazol-3-ylamino)-phenyl]-5,7,7-trimethyl-2,5,6,7-tetrahydro-[1,4]oxazepin-3-ylamine,
(R)-6,6-Difluoro-5-[2-fluoro-5-(4-fluoro-phenylamino)-phenyl]-5,7,7-trimethyl-2,5,6,7-tetrahydro-[1,4]oxazepin-3-ylamine,
(R)-6,6-Difluoro-5-[2-fluoro-5-(5-fluoro-pyridin-3-ylamino)-phenyl]-5,7,7-trimethyl-2,5,6,7-tetrahydro-[1,4]oxazepin-3-ylamine, and
(R)-6,6-Difluoro-5-[2-fluoro-5-(5-trifluoromethyl-pyridin-3-ylamino)-phenyl]-5,7,7-trimethyl-2,5,6,7-tetrahydro-[1,4]oxazepin-3-ylamine,
or a pharmaceutical acceptable salt thereof.

26. The compound of claim 1, selected from the group consisting of
(R)-6,6-Difluoro-5-[2-fluoro-5-(6-methoxy-pyridin-3-ylamino)-phenyl]-5,7,7-trimethyl-2,5,6,7-tetrahydro-[1,4]oxazepin-3-ylamine,
(R)-6,6-Difluoro-5-[2-fluoro-5-(6-methyl-pyridin-3-ylamino)-phenyl]-5,7,7-trimethyl-2,5,6,7-tetrahydro-[1,4]oxazepin-3-ylamine,
(R)-6,6-Difluoro-5-[2-fluoro-5-(pyridin-3-ylamino)-phenyl]-5,7,7-trimethyl-2,5,6,7-tetrahydro-[1,4]oxazepin-3-ylamine,
(R)-7-[3-((R)-3-Amino-6,6-difluoro-5,7,7-trimethyl-2,5,6,7-tetrahydro-[1,4]oxazepin-5-yl)-4-fluoro-phenylamino]-6,7-dihydro-5H-[1]pyrindine-3-carbonitrile,
(R)-7-[5-((R)-3-Amino-6,6-difluoro-5,7,7-trimethyl-2,5,6,7-tetrahydro-[1,4]oxazepin-5-yl)-2,4-difluoro-phenylamino]-6,7-dihydro-5H-[1]pyrindine-3-carbonitrile,
(S)-7-[3-((R)-3-Amino-6,6-difluoro-5,7,7-trimethyl-2,5,6,7-tetrahydro-[1,4]oxazepin-5-yl)-4-fluoro-phenylamino]-6,7-dihydro-5H-[1]pyrindine-3-carbonitrile,
[3-((R)-3-Amino-6,6-difluoro-5,7,7-trimethyl-2,5,6,7-tetrahydro-[1,4]oxazepin-5-yl)-4-fluoro-phenyl]-(3-chloro-6,7-dihydro-5H-[1]pyrindin-7-yl)-amine,
[3-((R)-3-Amino-6,6-difluoro-5,7,7-trimethyl-2,5,6,7-tetrahydro-[1,4]oxazepin-5-yl)-4-fluoro-phenyl]-(6-chloro-2,3-dihydro-furo[3,2-b]pyridin-3-yl)-amine,
[3-((R)-3-Amino-6,6-difluoro-5-methyl-2,5,6,7-tetrahydro-[1,4]oxazepin-5-yl)-4-fluoro-phenyl]-((S)-3-chloro-6,7-dihydro-5H-[1]pyrindin-7-yl)-amine,
[3-((R)-3-Amino-6,6-difluoro-5-methyl-2,5,6,7-tetrahydro-[1,4]oxazepin-5-yl)-4-fluoro-phenyl]-((R)-3-chloro-6,7-dihydro-5H-[1]pyrindin-7-yl)-amine,
4-[3-((R)-3-Amino-6,6-difluoro-5-methyl-2,5,6,7-tetrahydro-[1,4]oxazepin-5-yl)-4-fluoro-phenylamino]-benzonitrile, 8-[3-((R)-3-Amino-6,6-difluoro-5,7,7-trimethyl-2,5,6,7-tetrahydro-[1,4]oxazepin-5-yl)-4-fluoro-phenylamino]-5,6,7,8-tetrahydro-quinoline-3-carbonitrile, and (S)-7-[5-((R)-3-Amino-6,6-difluoro-5,7,7-trimethyl-2,5,6,7-tetrahydro-[1,4]oxazepin-5-yl)-2,4-difluoro-phenylamino]-6,7-dihydro-5H-[1]pyrindine-3-carbonitrile, or a pharmaceutical acceptable salt thereof.

27. The compound of claim 1, selected from the group consisting of

[3-((5R,6R)-3-Amino-6-fluoro-5-methyl-2,5,6,7-tetrahydro-[1,4]oxazepin-5-yl)-4-fluoro-phenyl]-(3-chloro-6,7-dihydro-5H-[1]pyrindin-7-yl)-amine, (R)-6,6-Difluoro-5-[2-fluoro-5-(1-methyl-1H-pyrazol-3-ylamino)-phenyl]-5,7,7-trimethyl-2,5,6,7-tetrahydro-[1,4]oxazepin-3-ylamine, (R)-6,6-Difluoro-5-[2-fluoro-5-(4-fluoro-phenylamino)-phenyl]-5,7,7-trimethyl-2,5,6,7-tetrahydro-[1,4]oxazepin-3-ylamine, and

[3-((R)-3-Amino-6,6-difluoro-5-methyl-2,5,6,7-tetrahydro-[1,4]oxazepin-5-yl)-4-fluoro-phenyl]-((S)-3-chloro-6,7-dihydro-5H-[1]pyrindin-7-yl)-amine, or a pharmaceutical acceptable salt thereof.

28. A pharmaceutical composition comprising a therapeutically effective amount of a compound of formula I

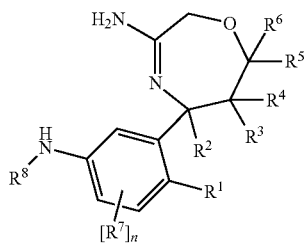

wherein $R^1$ is selected from the group consisting of
hydrogen,
halogen, and
$C_{1-6}$-alkyl;

$R^2$ is selected from the group consisting of
hydrogen,
$C_{1-6}$-alkyl, and
halogen-$C_{1-6}$-alkyl;

$R^3$ is selected from the group consisting of
halogen,
hydrogen, and
$C_{1-6}$-alkyl;

$R^4$ is selected from the group consisting of
hydrogen and
halogen;

$R^5$ is selected from the group consisting of
hydrogen and
$C_{1-6}$-alkyl;

$R^6$ is selected from the group consisting of
hydrogen and
$C_{1-6}$-alkyl;

$R^7$ is selected from the group consisting of
halogen and
$C_{1-6}$-alkyl;

n is 0 or 1; and $R^8$ is selected from the group consisting of
heteroaryl,
heteroaryl, substituted by 1-4 substituents individually selected from the group consisting of cyano, cyano-$C_{1-6}$-alkyl, halogen, halogen-$C_{1-6}$-alkyl, halogen-$C_{1-6}$-alkoxy, $C_{1-6}$-alkoxy and $C_{1-6}$-alkyl,
heteroaryl-$CH_2$—,
heteroaryl-$CH_2$—, substituted by 1-4 substituents individually selected from the group consisting of cyano, cyano-$C_{1-6}$-alkyl, halogen, halogen-$C_{1-6}$-alkyl, halogen-$C_{1-6}$-alkoxy, $C_{1-6}$-alkoxy and $C_{1-6}$-alkyl,
aryl,
aryl, substituted by 1-4 substituents individually selected from the group consisting of cyano, cyano-$C_{1-6}$-alkyl, halogen, halogen-$C_{1-6}$-alkyl, halogen-$C_{1-6}$-alkoxy, $C_{1-6}$-alkoxy and $C_{1-6}$-alkyl,
heterocyclyl, and
heterocyclyl, substituted by 1-4 substituents individually selected from the group consisting of cyano, cyano-$C_{1-6}$-alkyl, halogen, halogen-$C_{1-6}$-alkyl, halogen-$C_{1-6}$-alkoxy, $C_{1-6}$-alkoxy and $C_{1-6}$-alkyl;

or a pharmaceutically acceptable salt thereof and a pharmaceutically acceptable carrier.

* * * * *